US012668585B2

(12) United States Patent
Ramsden et al.

(10) Patent No.: US 12,668,585 B2
(45) Date of Patent: Jun. 30, 2026

(54) SUBSTITUTED PYRIMIDINYL-PYRAZOLES AS CDK2 INHIBITORS

(71) Applicant: BLUEPRINT MEDICINES CORPORATION, Cambridge, MA (US)

(72) Inventors: Philip D. Ramsden, Cambridge, MA (US); Neil Bifulco, Jr., Sudbury, MA (US); Natasja Brooijmans, Boston, MA (US); Emanuele Perola, Cambridge, MA (US); Richard Vargas, Cambridge, MA (US); Steven Mark Wenglowsky, Cambridge, MA (US); Douglas Wilson, Ayer, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 378 days.

(21) Appl. No.: 18/570,274

(22) PCT Filed: Jun. 15, 2022

(86) PCT No.: PCT/US2022/033576
§ 371 (c)(1),
(2) Date: Dec. 14, 2023

(87) PCT Pub. No.: WO2022/266190
PCT Pub. Date: Dec. 22, 2022

(65) Prior Publication Data
US 2024/0287040 A1 Aug. 29, 2024

Related U.S. Application Data

(60) Provisional application No. 63/327,474, filed on Apr. 5, 2022, provisional application No. 63/211,426, filed on Jun. 16, 2021.

(51) Int. Cl.
*C07D 403/04* (2006.01)
*A61P 35/00* (2006.01)
*C07D 405/14* (2006.01)

(52) U.S. Cl.
CPC ............ *C07D 403/04* (2013.01); *A61P 35/00* (2018.01); *C07D 405/14* (2013.01)

(58) Field of Classification Search
None
See application file for complete search history.

(56) References Cited

U.S. PATENT DOCUMENTS

| | | | |
|---|---|---|---|
| 8,058,290 | B2 | 11/2011 | Bjergarde et al. |
| 8,334,291 | B2 | 12/2012 | Schirok et al. |
| 11,932,648 | B2 | 3/2024 | Wilson et al. |
| 11,970,498 | B2 | 4/2024 | Wilson et al. |
| 2009/0197911 | A1 | 8/2009 | Georg et al. |
| 2023/0002376 | A1 | 1/2023 | Hummel et al. |
| 2023/0159535 | A1 | 5/2023 | Wilson et al. |
| 2023/0322791 | A1 | 10/2023 | Wilson et al. |
| 2024/0287040 | A1 | 8/2024 | Ramsden et al. |
| 2024/0383902 | A1 | 11/2024 | Wilson et al. |

FOREIGN PATENT DOCUMENTS

| | | | | |
|---|---|---|---|---|
| CN | 113135896 A | 7/2021 | | |
| CN | 114057733 A | 2/2022 | | |
| CN | 117717565 A | 3/2024 | | |
| WO | WO-2002/018346 A1 | 3/2002 | | |
| WO | WO-2002/022601 A1 | 3/2002 | | |
| WO | WO-2002/022602 A2 | 3/2002 | | |
| WO | WO-2002/022604 A1 | 3/2002 | | |
| WO | WO-2002/022606 A1 | 3/2002 | | |
| WO | WO-2002/022607 A1 | 3/2002 | | |
| WO | WO-2002/050065 A2 | 6/2002 | | |
| WO | WO-2002/050066 A2 | 6/2002 | | |
| WO | WO-0246184 A1 * | 6/2002 | ................ | A61P 5/14 |
| WO | WO-2002/059111 A2 | 8/2002 | | |
| WO | WO-2002/066461 A1 | 8/2002 | | |

(Continued)

OTHER PUBLICATIONS

U.S. Appl. No. 17/850,453 U.S. Pat. No. 11,932,648, CDK2 Inhibitors, filed Jun. 27, 2022, Patented.
U.S. Appl. No. 18/166,178 U.S. Pat. No. 11,970,498, CDK2 Inhibitors, Feb. 8, 2023, Patented.
U.S. Appl. No. 18/605,248 US 2024/0383902, CDK2 Iniiibitors, Mar. 14, 2024, Published.
U.S. Appl. No. 18/710,715, CDK2 Inhibitors and Methods of Making and Using Same, May 16, 2024, Pending.
Brown et al. "BLU-222, an investigational, potent, and selective CDK2 inhibitor, demonstrated robust antitumor activity in CCNE1-amplified ovarian cancer models," Poster No. 2306 presented at AACR Annual Meeting Apr. 8-13, 2022.
Brown et al. "CDK2 inhibition with BLU-222 in combination with ribociclib demonstrates robust antitumor activity in pre-clinical models of CDK4/6 inhibitor-naive and -resistant HR+/HER2- breast cancer," Poster P6-10-07, San Antonio Breast Cancer Symposium—Dec. 6-10, 2022.

(Continued)

*Primary Examiner* — Sarah Pihonak
*Assistant Examiner* — Donna M Nestor
(74) *Attorney, Agent, or Firm* — Goodwin Procter LLP

(57) ABSTRACT

The present disclosure provides a compound represented by structural formula (I): (I), or a pharmaceutically acceptable salt thereof useful for treating a cancer.

(I)

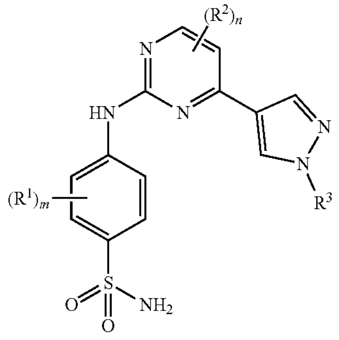

20 Claims, No Drawings

(56) References Cited

FOREIGN PATENT DOCUMENTS

| | | | |
|---|---|---|---|
| WO | WO-2002/068415 | A1 | 9/2002 |
| WO | WO-2004/037814 | A1 | 5/2004 |
| WO | WO-2005/068452 | A1 | 7/2005 |
| WO | WO-2006/087538 | A1 | 8/2006 |
| WO | WO-2007/017577 | A1 | 2/2007 |
| WO | WO-2007/024680 | A1 | 3/2007 |
| WO | WO-2008/117050 | A1 | 10/2008 |
| WO | WO-2008/129255 | A1 | 10/2008 |
| WO | WO-2010/078900 | A2 | 7/2010 |
| WO | WO-2011/055911 | A1 | 5/2011 |
| WO | WO-2011/079804 | A1 | 7/2011 |
| WO | WO-2012/064548 | A1 | 5/2012 |
| WO | WO-2012/077932 | A2 | 6/2012 |
| WO | WO-2013/026021 | A2 | 2/2013 |
| WO | WO-2014/181137 | A1 | 11/2014 |
| WO | WO-2014/181287 | A1 | 11/2014 |
| WO | WO-2015/017502 | A1 | 2/2015 |
| WO | WO-2016/057322 | A1 | 4/2016 |
| WO | WO-2016/193939 | A1 | 12/2016 |
| WO | WO-2018/106667 | A1 | 6/2018 |
| WO | WO-2019/183364 | A1 | 9/2019 |
| WO | WO-2019/220147 | A1 | 11/2019 |
| WO | WO-2020/108516 | A1 | 6/2020 |
| WO | WO-2020/108613 | A1 | 6/2020 |
| WO | WO-2020/157652 | A2 | 8/2020 |
| WO | WO-2020/205560 | A1 | 10/2020 |
| WO | WO-2020/264420 | A1 | 12/2020 |
| WO | WO-2021/072232 | A1 | 4/2021 |
| WO | WO-2021/104461 | A1 | 6/2021 |
| WO | WO-2022/061155 | A1 | 3/2022 |
| WO | WO-2022/174031 | A1 | 8/2022 |
| WO | WO-2022/184130 | A1 | 9/2022 |
| WO | WO-2022/221194 | A1 | 10/2022 |
| WO | WO-2022/245776 | A1 | 11/2022 |
| WO | WO-2022/266190 | A1 | 12/2022 |
| WO | WO-2023/278326 | A1 | 1/2023 |
| WO | WO-2023/092088 | A1 | 5/2023 |
| WO | WO-2023/092107 | A1 | 5/2023 |
| WO | WO-2024/148083 | A1 | 7/2024 |
| WO | WO-2024/148087 | A1 | 7/2024 |
| WO | WO-2024/148089 | A1 | 7/2024 |
| WO | WO-2024/148091 | A1 | 7/2024 |
| WO | WO-2024/168298 | A1 | 8/2024 |
| WO | WO-2024/216154 | A1 | 10/2024 |

OTHER PUBLICATIONS

Brown et al., "Abstract 2306: BLU-222, an investigational, potent, and selective CDK2 inhibitor, demonstrated robust antitumor activity in CCNE1-amplified ovarian cancer models," Cancer Res, 2022, 82 (12_Supplement): 2306 (3 pages).

Brown et al., "Abstract P6-10-07: CDK2 inhibition with BLU-222 in combination with ribociclib demonstrates robust antitumor activity in pre-clinical models of CDK4/6 inhibitor-naïve and -resistant HR+/HER2− breast cancer," Cancer Res, 2023, 83 (5_Supplement): P6-10-07 (3 pages).

Brown et al., "CDK2 regulates collapsed replication fork repair in CCNE1-amplified ovarian cancer cells via homologous recombination," NAR Cancer, 2023, 5(3), pp. 1-16.

CAS Registry No. 439213-71-5, STN entry date: Jul. 18, 2002; chemical name: 1H-Pyrazolo[3,4-b]pyrazin-6-amine, 5-(4-chlorophenyl)-3-methyl-1-(phenylmethyl)−.

CAS Registry No. 439214-73-0, STN entry date: Jul. 18, 2002; chemical name: 1H-Pyrazolo[3,4-b]pyrazin-6-amine, 3-methyl-5-phenyl-1-(phenylmethyl)−.

Choi et al. "Development of a selective CDK2-E Inhibitor in CCNE-aberrant cancers," Poster 1279 presented at AACR Apr. 9-14, 2021.

Choi et al., "Abstract 1279: Development of a selective CDK2-E inhibitor in CCNE driven cancers," Cancer Res, 2021, 81 (13_Supplement) (4 pages).

Clinical Trials—NCT05252416, entitled "(VELA) Study of BLU-222 in Advanced Solid Tumors," ClinicalTrials.gov, Aug. 23, 2023 (11 pages).

Etemadmoghadam et al., "Synthetic lethality between CCNE1 amplification and loss of BRCA1," PNAS, 2013, 110(48), pp. 19489-19494.

Freeman-Cook et al., "Recent Advances in the Discovery of Cyclin-Dependent Kinase 2 (CDK2) Selective Inhibitors," Medicinal Chemistry Review, 2023, 58, 283-311.

Honda et al., "The structure of cyclin E1/CDK2: implications for CDK2 activation and CDK2-independent roles," EMBO J, 2005, 24(3), pp. 452-463.

Hu et al., "Specific CP110 Phosphorylation Sites Mediate Anaphase Catastrophe after CDK2 Inhibition: Evidence for Cooperation with USP33 Knockdown," Mol. Cancer Ther., 2015, 14(11), pp. 2576-2585.

International Search Report and Written Opinion mailed Sep. 14, 2022, in International Patent Application No. PCT/US2022/035122, filed Jun. 27, 2022, by Blueprint Medicines Corp.

International Search Report and Written Opinion mailed Sep. 9, 2022, in International Patent Application No. PCT/US2022/033576, filed Jun. 15, 2022, by Blueprint Medicines Corp.

Le Brazidec et al: "Synthesis, SAR and biological evaluation of 1,6-disubstituted-1-pyrazolo[3,4-]pyrimidines as dual inhibitors of Aurora kinases and CDK1," Bioorganic & Medicinal Chemistry Letters, 2019, 22(5), pp. 2070-2074.

Mascarenhas et al. (2008) "An efficient tool for identifying inhibitors based on 3D-QSAR and docking using feature-shape pharmacophore of biologically active conformation—A case study with CDK2/CyclinA," European Journal of Medicinal Chemistry, 43(12) 2008.

Molenaar et al., "Inactivation of CDK2 is synthetically lethal to MYCN over-expressing cancer cells," PNAS USA, 2009, 106(31), pp. 12968-12973.

Noske et al., "Detection of CCNE1/URI (19q12) amplification by in situ hybridisation is common in high grade and type II endometrial cancer," Oncotarget, 2016, 8, pp. 14794-14805.

Ohtsubo et al., "Human cyclin E, a nuclear protein essential for the G1-to-S phase transition," Mol. Cell Biol., 1995, 15(5), pp. 2612-2624.

Ooi et al., "Gene amplification of CCNE1, CCND1, and CDK6 in gastric cancers detected by multiplex ligation-dependent probe amplification and fluorescence in situ hybridization," Human Pathology, 2017, 61, pp. 58-67.

Patel et al., "BLU-222, an oral, potent and selective CDK2 inhibitor, in patients with advanced solid tumors: phase 1 monotherapy dose escalation," Poster 293, ASCO Annual Meeting—Jun. 2-6, 2023 (1 page).

Patel et al., "BLU-222, an oral, potent, and selective CDK2 inhibitor, in patients with advance solid tumors: Phase 1 monotherapy dose escalation," ASCO Annual Meeting, 2023, 41 (16_Suppl): 3095 (1 page).

Patel et al., "VELA: A first-in-human phase 1/2 study of BLU-222, a potent, selective cyclin-dependent kinase (CDK) 2 inhibitor in patients with cyclin E1 gene (CCNE1)-amplified or CDK4/6 inhibitor-resistant advanced solid tumors," Cancer Res, 2023, 83 (5_Supplement): OT3-23-1.

Said et al., "A patent review of anticancer CDK2 inhibitors (2017-present)," Expert Opinion on Therapeutic Patents, 2022, 32(8), 885-898.

Scaltriti et al., "Cyclin E amplification/overexpression is a mechanism of trastuzumab resistance in HER2+ breast cancer patients," PNAS, 2011, 108(9), pp. 3761-3766.

Schenone et al: "Biologically Driven Synthesis of Pyrazolo[3,4-d]pyrimidines as Protein Kinase Inhibitors: An Old Scaffold as a New Tool for Medicinal Chemistry and Chemical Biology Studies," Chemical Review, 2014.

Tadesse et al., "Cyclin-Dependent Kinase 2 Inhibitors in Cancer Therapy: An Update," Journal of Medicinal Chemistry, 2019, 62(9), 4233-4251.

Tadesse et al., "Targeting CDK2 in cancer: challenges and opportunities for therapy," Drug Discovery Today, 2020, 25(2), pp. 406-413.

(56) References Cited

OTHER PUBLICATIONS

Takada et al., "FBW7 Loss Promotes Chromosomal Instability and Tumorigenesis via Cyclin E1/CDK2-Mediated Phosphorylation of CENP-A," Cancer Res., 2017, 77(18), pp. 4881-4893.
Yap et al., "491TiP: A first-in-human phase I/II study of BLU-222, a potent, selective CDK2 inhibitor in patients with CCNE1-amplified or CDK4/6 inhibitor-resistant advance solid tumors," ESMO, 2022, 33, Supplement 7, S765 (1 page).
Yap et al., "VELA: A first-in-human phase 1/2 study of BLU-222, a potent, selective cyclin-dependent kinase (CDK) 2 inhibitor in patients with cyclin E1 gene (CCNE1)-amplified or CDK4/6 inhibitor (CDK4/6i)-resistant advanced solid tumors (1275)," Gynecologic Oncology, 2023, 176, S173 (1 page).
Yap et al., "A first-in-human phase 1/2 study of BLU-222, a potent, selective CDK2 inhibitor in patients with CCNE1-amplified or CDK4/6 inhibitor-resistant advanced solid tumors," Poster 491TiP, ESMOCongress—Sep. 9-13, 2022 (1 page).
Zhang et al: "CDK inhibitors in cancer therapy, an overview of recent development," American Journal of Cancer Research, 2021, pp. 1913-1935.

* cited by examiner

SUBSTITUTED PYRIMIDINYL-PYRAZOLES AS CDK2 INHIBITORS

CROSS-REFERENCE TO RELATED APPLICATIONS

This application is a U.S. National Stage Application of International Patent Application No. PCT/US2022/033576, filed on Jun. 15, 2022, which claims the benefit of and priority to U.S. Provisional Patent Application No. 63/211,426, filed on Jun. 16, 2021, and U.S. Provisional Patent Application No. 63/327,474, filed on Apr. 5, 2022, the disclosure of each of which is hereby incorporated by reference in its entirety for all purposes.

BACKGROUND

Cyclin-Dependent Kinase (CDK) are serine/threonine protein kinases that have a central role in cell cycle progression. CDK levels remain relatively constant throughout the cell cycle, and it is the selective activation of specific CDKs allows for the proper ordering of the steps in cell cycle progression. Activation of CDKs requires heterodimerization with regulatory subunits known as cyclins. Cell cycle deregulation is a common feature of human cancer.

Cyclin-dependent kinase 2 (Cdk2) participates in a range of biological activities. CDK2 is a key cell cycle regulator, active from the late $G_1$-phase and throughout the S-phase. CDK2 is involved in DNA damage response (DDR) through the homologous recombination (HR) pathway. CDK2 also regulates aspects of apoptotic pathways. Cyclin E1 (CCNE1), cyclin E2 (CCNE2), cyclin A1 (CCNA1), and cyclin A2 (CCNA2), along with p21Cip1/Waf1, p27Kip1 and p57Kip2 (the cyclin dependent kinase inhibitors of the cyclin-CDK2 complex) are the main regulators of CDK2 activity. In cancer, dysregulation of the binding of CDK2 by cyclin E1, E2, A1, or A2 or the activity of the cyclin-dependent kinase inhibitor proteins may occur. (See S. Tadesse et al., Drug Discovery Today, Volume 25, Number 2 Feb. 2020)

The dysregulation of CDK2 can occur through several mechanisms. Amplification or overexpression of CCNE1 has been identified occurring in ovarian and breast cancer (See Scaltriti, M. et al., Proc. Natl Acad. Sci. USA 108, 3761-3766 (2011) and Etemadmoghadam, D. et al. Proc. Natl Acad. Sci. USA 110, 19489-19494 (2013). Poor outcomes in gastric, endometrial, and other cancers have been associated with overexpression or amplification of CCNE1 (See Ooi et al. Hum Pathol. (2017) 61:58-67, and Noske et al, Oncotarget (2017) 8: 14794-14805).

While these findings indicate CDK2 is a potential target for cancers with deregulated CDK2 activity, no agents targeting CDK2 have been approved to date. Therefore, there is a need to develop new CDK2 inhibitors.

SUMMARY

The applicant has discovered novel compounds which are effective inhibitors of CDK2 (see Synthetic Examples 1-46). In particular, it has been demonstrated that the compounds of the present disclosure effectively inhibit CDK2. Compounds of the disclosure (also referred to herein as the "disclosed compounds") or pharmaceutically acceptable salts thereof effectively inhibit CDK2. (see Biological Example 1) and can be used treat various cancers. Importantly, the disclosed compounds are selective CDK2 inhibitors, i.e., the disclosed compounds have no or low activity against CDK1. Advantages associated with such selectivity may include facilitating efficacious dosing and reducing CDK1-mediated on-target toxicities. Some of the disclosed compounds also have the advantage of having high microsomal stability. Compounds of the disclosure also may have favorable toxicity profiles related to other non-kinase targets.

In one aspect, the present disclosure provides a compound represented by the following structural Formula (I):

(I)

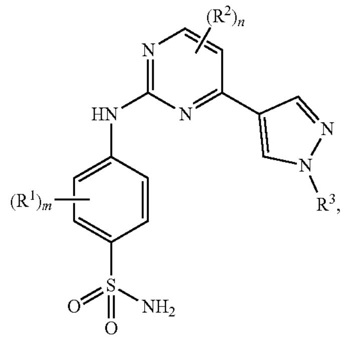

or a pharmaceutically acceptable salt thereof, the definition of each variable is provided below.

In another aspect, the present disclosure provides a pharmaceutical composition comprising a pharmaceutically acceptable carrier or diluent and one or more of the compounds disclosed herein, or a pharmaceutically acceptable salt thereof (a "pharmaceutical composition of the disclosure").

The present disclosure provides a method of treating a subject with cancer, comprising administering to the subject an effective amount of a compound of the disclosure (e.g., a compound of Formula (I)) or a pharmaceutically acceptable salt thereof or a pharmaceutical composition of the disclosure. In one embodiment, the cancer is uterine cancer (including uterine carcinosarcoma, uterine corpus endometrial carcinoma), endometrial cancer, breast cancer (including breast invasive carcinoma, TNBC (triple negative breast cancer), ER (estrogen receptor)+HER2 (human epidermal growth factor 2)− breast cancer, and HER2+ breast cancer), ovarian cancer (e.g. ovarian serous cystandenocarcinoma), stomach cancer (including stomach adenocarcinoma), gastric cancer (including gastrointestinal stromal tumor), colorectal cancer, pancreatic cancer, kidney cancer, head and neck cancer, liver cancer, prostate cancer, skin cancer, leukemia (including AML (acute myeloid leukemia)), lymphoma (including B-cell lymphoma), sarcoma, esophageal cancer (including esophageal carcinoma), bladder cancer (including bladder urothelial carcinoma), lung cancer (including lung squamous carcinoma and non-small cell lung cancer, e.g., EGFRm (epidermal growth factor receptor mutant)+non-small cell lung cancer), cholangiocarcinoma, adrenocortical carcinoma, or mesothelioma.

In one embodiment, the cancer to be treated has CCNE1 amplification or overexpression.

The treatment method disclosed herein further comprises administering to the subject an effective amount of palbociclib (e.g., Ibrance®), ribociclib, abemaciclib, tamoxifen, letrozole, olaparib (e.g., Lynparza®), niraparib, carboplatin, cisplatin, paclitaxel, gemcitabine, megestrol acetate, medroxyprogesterone acetate, capecitabine (e.g., Xeloda®), regorafenib (e.g., Stivarga®), afatinib (e.g., Gilotrif®), osimertinib (e.g., Tagrisso®), gefitinib (e.g., Iressa®), erlotinib (e.g., Tarceva®), ramucirumab (e.g., Cyramza®), an EGFR inhibitor, pralsetinib, ABT-263 (navitoclax), MK-1775 (adavosertib), BAY-1895344, berzosertib, ceralasertib, SRA-737, LY2603618 (rabusertib), or trastuzumab (e.g., Herceptin®), or combinations thereof. The EGFR inhibitor may be selected from afatinib, osimertinib, lapatinib, erlotinib, dacomitinib, poziotinib, neratinib, gefitinib JBJ-04-125-02, alflutinib (AST 2818), aumolertinib (formerly almonertinib) (HS10296), BBT-176, BI-4020, BPI-361175, BPI-D0316, CH7233163, gilitertinib, icotinib. JND-3229, lazertinib, nazartinib (EGF 816), avitinib, PCC-0208027, rezivertinib (BPI-7711), TQB3804, zorifertinib (AZ-3759), or DZD9008; an EGFR antibody such as cetuximab, panitumumab, necitumumab, HLX07, JMT101; or a bispecific EGFR and MET antibody (e.g., amivantamab ((JNJ-61186372, JNJ-372)).

The present disclosure also provides a method of inhibiting CDK2 in a subject in need thereof, comprising administering to the subject an effective amount of a compound of the disclosure (e.g., a compound of Formula (I)) or a pharmaceutically acceptable salt thereof or a pharmaceutical composition of the disclosure.

The present disclosure also provides the use of an effective amount of a compound of the disclosure (e.g., a compound of Formula (I)), or a pharmaceutically acceptable salt thereof, or a pharmaceutical composition of the disclosure, for the preparation of a medicament for the treatment of cancers.

In another aspect, provided herein a compound of Formula (I), or a pharmaceutically acceptable salt thereof, or a pharmaceutical composition of the disclosure for use in treating cancers.

In one aspect, the present disclosure provides a method of treating a subject having, or at risk of developing, a disease or disorder associated with CDK2, comprising administering to the subject a therapeutically effective amount of a compound disclosed herein, or a pharmaceutically acceptable salt thereof, or a pharmaceutical composition disclosed herein, wherein the subject has an amplification of the CCNE1 gene and/or have an expression level of CCNE1 higher than a control expression level of CCNE1. In some embodiments, the disease or disorder associated with CDK2 is cancer.

Also provided herein is a method of treating a patient having an amplified expression level of CCNE1 and suffering from, or at risk of developing, a solid tumor cancer, comprising administering to the patient a therapeutically effective amount of a compound disclosed herein, or a pharmaceutically acceptable salt thereof, or a pharmaceutical composition disclosed herein.

The contemplated solid tumor cancer may be at least one of: uterine cancer (including uterine carcinosarcoma, uterine corpus endometrial carcinoma), endometrial cancer, breast cancer (including breast invasive carcinoma, TNBC (triple negative breast cancer), ER (estrogen receptor)+HER2 (human epidermal growth factor 2)− breast cancer, and HER2+ breast cancer), ovarian cancer (e.g. ovarian serous cystandenocarcinoma), stomach cancer (including stomach adenocarcinoma), gastric cancer (including gastrointestinal stromal tumor), colorectal cancer, pancreatic cancer, kidney cancer, head and neck cancer, liver cancer, prostate cancer, skin cancer, lymphoma (including B-cell lymphoma), sarcoma, esophageal cancer (including esophageal carcinoma), bladder cancer (including bladder urothelial carcinoma), lung cancer (including lung squamous carcinoma and non-small cell lung cancer, e.g., EGFRm (epidermal growth factor receptor mutant)+non-small cell lung cancer), cholangiocarcinoma, adrenocortical carcinoma, or mesothelioma.

DETAILED DESCRIPTION

Definitions

The term "halo" as used herein means halogen and includes chloro, fluoro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-4 carbon atoms, i.e. $(C_1\text{-}C_4)$alkyl. As used herein, a "$(C_1\text{-}C_4)$alkyl" group means a radical having from 1 to 4 carbon atoms in a linear or branched arrangement. Examples include methyl, ethyl, n-propyl, iso-propyl, and the like.

The term "alkoxy" means an alkyl radical attached through an oxygen linking atom, represented by —O-alkyl. For example, "$(C_1\text{-}C_4)$alkoxy" includes methoxy, ethoxy, propoxy, and butoxy.

The term "cycloalkyl" refers to a monocyclic saturated hydrocarbon ring system. Unless otherwise specified, cycloalkyl has from 3-6 carbon atoms. For example, a $C_3\text{-}C_6$ cycloalkyl includes cyclopropyl, cyclobutyl, cyclopentyl and cyclohexyl. Unless otherwise described, a "cycloalkyl" has from three to six carbon atoms.

The term "heterocyclyl" or "heterocyclic" refers to a radical of a 3- to 6-membered non-aromatic ring system having ring carbon atoms and 1 to 2 ring heteroatoms, wherein each heteroatom is independently selected from nitrogen, quaternary nitrogen, oxidized nitrogen (e.g., NO), oxygen, and sulfur, including sulfoxide and sulfone ("4-12 membered heterocyclyl. In heterocyclyl groups that contain one or more nitrogen atoms, the point of attachment can be a carbon or nitrogen atom, as valency permits. Exemplary heterocyclyl groups include azetidinyl, oxetanyl, thietanyl, tetrahydrofuranyl, pyrrolidinyl, piperidinyl, tetrahydropyranyl, piperazinyl, morpholinyl, azepanyl, oxepanyl, thiepanyl, tetrahydropyridinyl, and the like.

Compounds of the Present Disclosure

Disclosed herein are embodiments of compounds having a general structure of Formula (I). The present invention provides a compound of the present invention or a pharmaceutically acceptable salt thereof for use in the treatment of cancer. These compounds are selective inhibitors of CDK2.

In a first embodiment, the present disclosure provides a compound represented by the following structural formula (I):

(I)

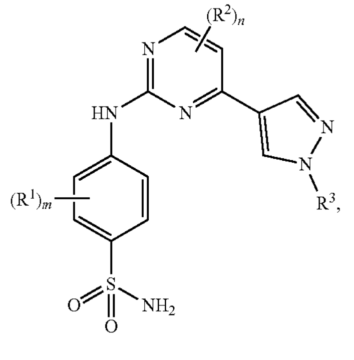

or a pharmaceutically acceptable salt thereof, wherein each $R^1$ is independently selected from the group consisting of halo, OH, CN, $C_1$-$C_4$ alkyl, and $C_1$-$C_4$ alkoxy, wherein the $C_1$-$C_4$ alkyl and $C_1$-$C_4$alkoxy are each optionally substituted with 1 to 3 halo;

each $R^2$ is independently selected from the group consisting of halo, OH, CN, $C_1$-$C_4$ alkyl, and $C_1$-$C_4$ alkoxy, wherein the $C_1$-$C_4$ alkyl and $C_1$-$C_4$alkoxy are each optionally substituted with 1 to 3 halo;

$R^3$ is $C_1$-$C_6$ alkyl optionally substituted with 1 or 2 groups each independently selected from the group consisting of halo, OH, $C_3$-$C_6$cycloalkyl, and 3 to 6-membered heterocyclyl, wherein the $C_3$-$C_6$ cycloalkyl is optionally substituted with OH, wherein the 3 to 6-membered heterocyclyl has 1 to 4 ring heteroatoms each independently selected from the group consisting of 0. S and NR and then is optionally substituted on a ring carbon with OH; or $R^3$ is $C_3$-$C_6$cycloalkyl or 3 to 6-membered heterocyclyl, wherein the $C_3$-$C_6$cycloalkyl is optionally substituted with OH or —$CH_2OH$, wherein the 3 to 6-membered heterocyclyl has 1 to 4 ring heteroatoms each independently selected from the group consisting of O, S and $NR^a$ and then is optionally substituted on a ring carbon with OH or —$CH_2OH$;

each $R^a$ is independently H or $C_1$-$C_6$alkyl;

m is selected from the group consisting of 0, 1, 2, 3, and 4, and n is selected from the group consisting of 0, 1, and 2.

In some embodiments, the compound is of Formula IIA, Formula IIB, Formula IIC, or Formula IID (IIA)

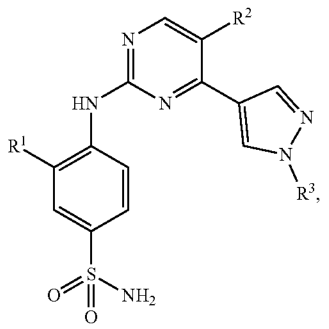

(IIB)

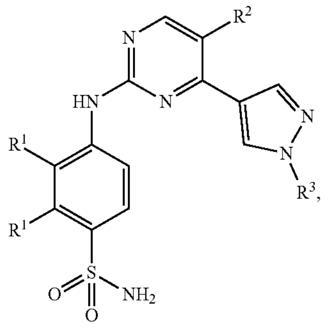

-continued (IIC)

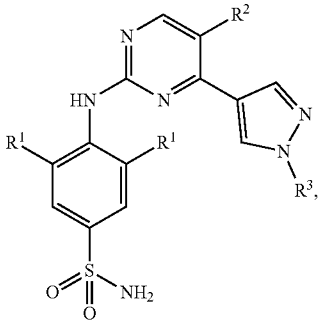

or (IID)

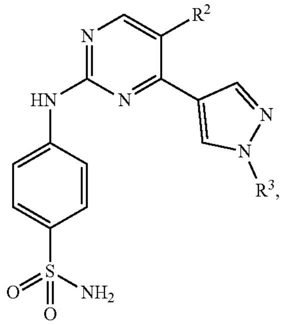

or a pharmaceutically acceptable salt thereof.

In some embodiments, each $R^1$ is independently selected from the group consisting of halo, methyl, and methoxy. For example, $R^1$ is halo, e.g., F, Cl, Br.

In certain embodiments, each $R^2$ is independently selected from the group consisting of halo, CN, methyl, and ethyl, wherein the methyl and ethyl are each optionally substituted with 1 to 3 halo. For example, $R^2$ is methyl optionally substituted with 1 to 3 halo, e.g., methyl, $CF_3$, $CF_2$. For example, $R^2$ may be CN. In some embodiments, $R^2$ may be halo, e.g., F, Cl, Br.

In other embodiments, $R^3$ is $C_1$-$C_5$ alkyl optionally substituted with 1 or 2 groups each independently selected from the group consisting of halo, OH, cyclopropyl and oxetanyl, wherein the cyclopropyl and oxetanyl are each optionally substituted with OH.

In some embodiments, $R^3$ is $C_1$-$C_5$ alkyl substituted with OH.

In certain embodiments, $R^3$ is cyclopropyl or oxetanyl, wherein the cyclopropyl and oxetanyl are each optionally substituted with OH or $CH_2OH$ (on a ring carbon if $R^3$ is oxetanyl).

In certain embodiments, R3 is tetrahydropyran.

In other embodiments, each $R^1$ is methyl, each $R^2$ is independently selected from the group consisting of halo, methyl, and $CF_3$, and $R^3$ is $C_1$-$C_6$ alkyl substituted with OH.

In some embodiments, each $R^1$ is halo, each $R^2$ is independently selected from the group consisting of halo, CN, methyl, ethyl, and $CF_3$, and $R^3$ is $C_1$-$C_6$ alkyl substituted with OH, or $R^3$ is oxetanyl or cyclopropyl, wherein the oxetanyl and cyclopropyl are each optionally substituted with $CH_2OH$ (on a ring carbon if $R^3$ is oxetanyl).

In other embodiments, each $R^1$ is methoxy, each $R^2$ is independently selected from the group consisting of halo, methyl, and $CF_3$, and $R^3$ is $C_1$-$C_6$ alkyl substituted with OH.

In certain embodiments, m may be 0. In some embodiments, m may be 1. In other embodiments, m may be 2. In certain embodiments, n may be 0. In some embodiments, n may be 1. In other embodiments, n may be 2.

In one embodiment, a compound of the present disclosure is any one of the compounds disclosed in the examples and Table 1, or a pharmaceutically acceptable salt thereof.

The term "pharmaceutically-acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in *J. Pharm. Sci.,* 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric, hydrobromic, phosphoric, metaphosphoric, nitric, and sulfuric acids) and of organic acids (such as acetic, benzenesulfonic, benzoic, ethanesulfonic, methanesulfonic, and succinic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

Compounds having one or more chiral centers can exist in various stereoisomeric forms, i.e., each chiral center can have an R or S configuration, or can be a mixture of both. Stereoisomers are compounds that differ only in their spatial arrangement. Stereoisomers include all diastereomeric and enantiomeric forms of a compound. Enantiomers are stereoisomers that are mirror images of each other. Diastereomers are stereoisomers having two or more chiral centers that are not identical and are not mirror images of each other.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the enrichment of the indicated configuration relative to the opposite configuration is greater than 50%, 60%, 70%, 80%, 90%, 99% or 99.9% (except when the designation "rac" or "racemate accompanies the structure or name, as explained in the following two paragraphs). "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When the stereochemical configuration at a chiral center in a compound is depicted by chemical name (e.g., where the configuration is indicated in the name by "R" or "S") or structure (e.g., the configuration is indicated by "wedge" bonds) and the designation "rac" or "racemate" accompanies the structure or is designated in the chemical name, a racemic mixture is intended.

When two stereoisomers are depicted by their chemical names or structures, and the chemical names or structures are connected by an "and", a mixture of the two stereoisomers is intended.

When two stereoisomers are depicted by their chemical names or structures, and the names or structures are connected by an "or", one or the other of the two stereoisomers is intended, but not both.

When a disclosed compound having a chiral center is depicted by a structure without showing a configuration at that chiral center, the structure is meant to encompass the compound with the S configuration at that chiral center, the compound with the R configuration at that chiral center, or the compound with a mixture of the R and S configuration at that chiral center. When a disclosed compound having a chiral center is depicted by its chemical name without indicating a configuration at that chiral center with "S" or "R", the name is meant to encompass the compound with the S configuration at that chiral center, the compound with the R configuration at that chiral center or the compound with a mixture of the R and S configuration at that chiral center.

A racemic mixture means a mixture of 50% of one enantiomer and 50% of its corresponding enantiomer. The present teachings encompass all enantiomerically-pure, enantiomerically-enriched, diastereomerically pure, diastereomerically enriched, and racemic mixtures, and diastereomeric mixtures of the compounds disclosed herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

"Peak 1" in the Experimental section refers to an intended reaction product compound obtained from a chromatography separation/purification that elutes earlier than a second intended reaction product compound from the same preceding reaction. The second intended product compound is referred to as "peak 2".

When a disclosed compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that, unless otherwise indicated, one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

In the compounds of the disclosure, any position specifically designated as "D" or "deuterium" is understood to have deuterium enrichment at 50, 80, 90, 95, 98 or 99%. "Deuterium enrichment" is a mole percent and is determined by dividing the number of compounds with deuterium at the indicated position by the total number of all of the compounds. When a position is designated as "H" or "hydrogen", the position has hydrogen at its natural abundance. When a position is silent as to whether hydrogen or deuterium is present, the position has hydrogen at its natural abundance. One specific alternative embodiment is directed to a compound of the disclosure having deuterium enrichment of at least 5, 10, 25, 50, 80, 90, 95, 98 or 99% at one or more positions not specifically designated as "D" or "deuterium".

As used herein, many moieties (e.g., alkyl, alkoxy, cycloalkyl or heterocyclyl) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. Where if more than one substituent is present, then each substituent may be independently selected. Such means for substitution are well-known in the art and/or taught by the instant disclosure. The optional substituents can be any substituents that are suitable to attach to the moiety.

Compounds of the disclosure are CDK2 inhibitors. As used herein, the term "selective CDK2 inhibitor" means a compound which selectively inhibits CDK2 over other CDKs and the kinome. Said another way, a selective CDK2 inhibitor has no or low activity against other CDKs and the kinome. A selective CDK2 inhibitor's inhibitory activity against CDK2 is more potent in terms of $IC_{50}$ value (i.e., the $IC_{50}$ value is subnanomolar) when compared with its inhibitory activity against other CDKs and many other kinases. Potency can be measured using known biochemical assays.

In some embodiments, the compounds of the disclosure are selective against CDK2 versus CDK1. In some such embodiments, compounds show at least 10-fold selectivity for CDK2 versus CDK1. In other embodiments, compounds show at least 20-fold selectivity for CDK2 versus CDK1. In specific embodiments, compounds show at least 30-fold selectivity for CDK2 versus CDK1 In certain embodiments, compounds show at least 40-fold selectivity for CDK2 versus CDK1. In other embodiments, compounds show at least 50-fold selectivity for CDK2 versus CDK1 For example, compounds show at least 100-fold selectivity for CDK2 versus CDK1. In some embodiments, the compounds of the invention are selective against CDK2 versus CDK4 and/or CDK6. In some such embodiments, compounds show at least 10-fold selectivity for CDK2 versus CDK4 and/or CDK6. In other embodiments, compounds show at least 20-fold selectivity for CDK2 versus CDK4 and/or CDK6. In specific embodiments, compounds show at least 30-fold selectivity for CDK2 versus CDK4 and/or CDK6.

Some compounds of the disclosure have the advantage of good metabolic stability. One indicator of good metabolic stability is high microsomal stability. Hepatic metabolism is a predominant route of elimination for small molecule drugs. The clearance of compounds by hepatic metabolism can be assessed in vitro using human liver microsomes (HLMs) or human hepatocytes. Compounds are incubated with HLMs plus appropriate co-factors or human hepatocytes and compound depletion is measured to determine an in vitro intrinsic clearance (Clint). The Clint is scaled to total body clearance (CL), and a hepatic extraction ratio (ER) is determined by dividing CL to standard human hepatic blood flow. Compounds that have a low hepatic extraction ratio are considered to have good metabolic stability. In some embodiments, a compound of the disclosure has a calculated ER of <0.3, <0.4, <0.5, <0.6.

Pharmaceutical Compositions

Pharmaceutical compositions of the disclosure (also referred to herein as the "disclosed pharmaceutical compositions") comprise one or more pharmaceutically acceptable carrier(s) or diluent(s) and a compound of the disclosure (e.g., a compound of Formula (I)), or a pharmaceutically acceptable salt thereof.

"Pharmaceutically acceptable carrier" and "pharmaceutically acceptable diluent" refer to a substance that aids the formulation and/or administration of an active agent to and/or absorption by a subject and can be included in the pharmaceutical compositions of the disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, hydroxymethylcellulose, fatty acid esters, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds or pharmaceutically acceptable salts thereof.

The pharmaceutical compositions of the disclosure optionally include one or more pharmaceutically acceptable carriers and/or diluents therefor, such as lactose, starch, cellulose and dextrose. Other excipients, such as flavoring agents, sweeteners, and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

The compounds disclosed herein inhibit CDK2 and therefore are useful for treating diseases for which CDK2 is dysregulated, such as cancer. The present disclosure provides a method of inhibiting CDK2 in a subject in need thereof, comprising administering to the subject an effective amount of a compound disclosed herein, a pharmaceutically acceptable salt thereof or a pharmaceutical composition disclosed herein.

In some embodiments, the disclosure provides a method of treating a disease or disorder associated with CDK2 in a patient, comprising administering to the patient a therapeutically effective amount of a compound of Formula (I) or any of the formulas as described herein, or a pharmaceutically acceptable salt thereof. In some embodiments, the disease or disorder associated with CDK2 is associated with an amplification of the cyclin E1 (CCNE1) gene and/or overexpression of CCNE1. In some embodiments, the disease or disorder is cancer.

Subjects "in need of inhibiting CDK2" are those having a disease for which a beneficial therapeutic effect can be achieved by inhibiting CDK2, e.g., a slowing in disease progression, alleviation of one or more symptoms associated with the disease or increasing the longevity of the subject in view of the disease.

In some embodiments, the disclosure provides a method of treating a disease/condition/or cancer associated with or modulated by CDK2, wherein the inhibition of CDK2 is of therapeutic benefit, including but not limited to the treatment of cancer in a subject in need thereof. The method comprises administering to the subject an effective amount of a compound disclosed herein, a pharmaceutically acceptable salt thereof, or pharmaceutical composition disclosed herein.

In another embodiment, the disclosure provides a method of treating a subject with cancer, comprising administering to the subject an effective amount of a compound disclosed herein, a pharmaceutically acceptable salt thereof, or a pharmaceutical composition disclosed herein. In another embodiment, the cancer is characterized by amplification or overexpression of CCNE1 or CCNE2.

Accordingly, in some embodiments of the methods, the subject or patient has been previously determined to have an amplification of the cyclin E1 (CCNE1) gene and/or an expression level of CCNE1 in a biological sample obtained from the subject or patient that is higher than a control expression level of CCNE1.

In another embodiment, the disclosure provides a method for inhibiting growth of tumor (e.g., cancer) cells in vitro. The method includes contacting the tumor (e.g. cancer) cells in vitro with a compound of Formula (I) or a pharmaceutically acceptable salt thereof. In another embodiment, the present disclosure provides a method for inhibiting growth of tumor (e.g., cancer) cells with CCNE1 amplification and overexpression in a subject or a patient. The method includes administering to the subject or patient in need thereof a therapeutically effective amount of a compound of Formula (I), or a pharmaceutically acceptable salt thereof.

In another embodiment, the disclosure provides a method of treating a subject with cancer, comprising administering to the subject an effective amount of a compound disclosed herein, a pharmaceutically acceptable salt thereof, or a pharmaceutical composition disclosed herein in conjunction with other agents or standard cancer treatments, as described below.

As used herein "cancer" refers to any malignant and/or invasive growth or tumor caused by abnormal cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one. In some such embodiments, the cancer is characterized by amplification or overexpression of CCNE1 and/or CCNE2.

Cancers to be treated according to the disclosed methods include breast cancer, ovarian cancer, bladder cancer, uterine cancer (e.g., uterine carcinosarcoma), prostate cancer, lung cancer (including NSCLC, SCLC, squamous cell carcinoma or adenocarcinoma), esophageal cancer, head and neck cancer, colorectal cancer (e.g., colon cancer), kidney cancer (including RCC), liver cancer (including HCC), pancreatic cancer, stomach (i.e., gastric) cancer, urothelial cancer, brain cancers, mesothelioma, skin cancer (e.g., melanoma), sarcoma, or thyroid cancer, including metastasis (in particular brain metastasis) of all cancers listed. In some embodiments, the cancer is characterized by at overexpression or amplification of CCNE1 and/or CCNE2 described herein. In some embodiments of the methods provided herein, the subject is identified as having a cancer characterized by amplification or overexpression of CCNE1 and/or CCNE2.

In further embodiments of the methods provided herein, the cancer is breast cancer, ovarian cancer, bladder cancer, uterine cancer, prostate cancer, lung cancer, esophageal cancer, liver cancer, pancreatic cancer or stomach cancer. In some such embodiments, the cancer is characterized by amplification or overexpression of CCNE1 and/or CCNE2.

In some embodiments, the disease or disorder associated with CDK2 is an adenocarcinoma, carcinoma, or cystadenocarcinoma.

In other embodiments, the cancer is breast cancer, including, e.g., ER-positive/HR-positive, HER2-negative breast cancer, ER-positive/HR-positive. HER2-positive breast cancer; triple negative breast cancer (TNBC); or inflammatory breast cancer. In some embodiments, the breast cancer is chemotherapy or radiotherapy resistant breast cancer, endocrine resistant breast cancer, trastuzumab resistant breast cancer, or breast cancer demonstrating primary or acquired resistance to CDK4/CDK6 inhibition. In some embodiments, the breast cancer is advanced or metastatic breast cancer. In some embodiments of each of the foregoing, the breast cancer is characterized by amplification or overexpression of CCNE1 and/or CCNE2.

In some embodiments, the cancer is ovarian cancer. In some such embodiments, the cancer is ovarian cancer characterized by amplification or overexpression of CCNE1 and/or CCNE2. In some such embodiments, the cancer is (a) ovarian cancer; (b) characterized by amplification or overexpression of cyclin E1 (CCNE1) or cyclin E2 (CCNE2); or (c) both (a) and (b). In some embodiments, the cancer is ovarian cancer.

In some embodiments, the compound of the disclosure is administered as first line therapy. In other embodiments, the compound of the disclosure is administered as second (or later) line therapy. In some embodiments, the compound of the disclosure is administered as second (or later) line therapy following treatment with an endocrine therapeutic agent and/or a CDK4/CDK6 inhibitor In some embodiments, the compound of the disclosure is administered as second (or later) line therapy following treatment with an endocrine therapeutic agent, e.g., an aromatase inhibitor, a SERM or a SERD. In some embodiments, the compound of the disclosure is administered as second (or later) line therapy following treatment with a CDK4/CDK6 inhibitor. In some embodiments, the compound of the disclosure is adminstered as second (or later) line therapy following treatment with one or more chemotherapy regimens, e.g., including taxanes or platinum agents. In some embodiments, the compound of the disclosure is administered as second (or later) line therapy following treatment with HER2 targeted agents, e.g., trastuzumab.

In some embodiments, the disease or disorder associated with CDK2 is N-mye amplified neuroblastoma cells (see Molenaar, et al., Proc Natl Acad Sci USA 106(31): 12968-12973) K-Ras mutant lung cancers (see Hu, S., et al., Mol Cancer Ther. 2015. 14(11): 2576-85, and cancers with FBW7 mutation and CCNE1 overexpression (see Takada, et al., Cancer Res, 2017.77(18): 4881-4893).

In some embodiments, the compounds of the present disclosure can be used to treat sickle cell disease and sickle cell anemia.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma. Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers.

In some embodiments, cancers treatable with compounds of the present disclosure include melanoma (e.g., metastatic malignant melanoma. BRAF and HSP90 inhibition-resistant melanoma), renal cancer (e.g., clear cell carcinoma), prostate cancer (e.g., hormone refractory prostate adenocarcinoma), breast cancer, colon cancer, lung cancer (e.g., non-small cell lung cancer and small cell lung cancer), squamous cell head and neck cancer, urothelial cancer (e.g., bladder) and cancers with high microsatellite instability (MSIhigh). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma. Non-Hodgkin lymphoma (including follicular lymphoma, including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer. Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular). Hodgkin lymphoma, myeloproliferative diseases (e.g., primary myelofibrosis (PNIF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma. Ewing's sarcoma, osteosarcoma, rhabdomyosarcoma, angiosarcoma, fibrosarcoma, liposarcoma, myxoma, rhabdomyoma, rhabdosarcoma, fibroma, lipoma, hamartoma, and teratoma.

Exemplary lung cancers include non-small cell lung cancer (NSCLC), small cell lung cancer (SCLC), bronchogenic carcinoma, squamous cell, undifferentiated small cell, undifferentiated large cell, adenocarcinoma, alveolar (bronchiolar) carcinoma, bronchial adenoma, chondromatous hamartoma, and mesothelioma. Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma. Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma. Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors. Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, Merkel cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Combinations

Compounds of the disclosure may be administered as single agents or may be administered in combination with other anti-cancer therapeutic agents, in particular standard of care agents appropriate for the particular cancer.

The term "additional anticancer therapeutic agent" as used herein means any one or more therapeutic agent, other than a compound of the disclosure, that is or can be used in the treatment of cancer. In some embodiments, such additional anticancer therapeutic agents include compounds derived from the following classes: mitotic inhibitors, alkylating agents, antimetabolites, antitumor antibiotics, anti-angiogenesis agents, topoisomerase I and II inhibitors, plant alkaloids, hormonal agents and antagonists, growth factor inhibitors, radiation, signal transduction inhibitors, such as inhibitors of protein tyrosine kinases and/or serine/threonine kinases, cell cycle inhibitors, biological response modifiers, enzyme inhibitors, antisense oligonucleotides or oligonucleotide derivatives, cytotoxics, immuno-oncology agents, and the like.

In some embodiments, the additional anticancer agent is an endocrine agent, such as an aromatase inhibitor, a SERD or a SERM.

In other embodiments, a compound of the disclosure may be administered in combination with a standard of care agent. In some embodiments, a compound of the disclosure may be administered in combination with endocrine therapy, e.g., agents such as letrozole, fulvestrant, tamoxifen, exemestane, or anastrozole. In some embodiments, a compound of the disclosure may be administered in combination with a chemotherapeutic agent, e.g., docetaxel, paclitaxel, cisplatin, carboplatin, capecitabine, gemcitabine or vinorelbine. In other embodiments, a compound of the invention may be administered in combination with an anti-HER2 agent, e.g., trastuzumab or pertuzumab.

In some embodiments, the additional anticancer agent is an anti-angiogenesis agent, including for example VEGF inhibitors, VEGFR inhibitors, TIE-2 inhibitors, PDGFR inhibitors, angiopoetin inhibitors, PKCb inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors. Preferred anti-angiogenesis agents include sunitinib (Sutent™), bevacizumab (Avastin™), axitinib (AG 13736), SU 14813 (Pfizer), and AG 13958 (Pfizer). Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer). Other anti-angiogenesis agents include enzastaurin (LY 317615), midostaurin (CGP 41251), perifosine (KRX 0401), teprenone (Selbex™) and UCN 01 (Kyowa Hakko). Other examples of anti-angiogenesis agents include celecoxib (Celebrex™), parecoxib (Dynastat™), deracoxib (SC 59046), lumiracoxib (Preiger™), valdecoxib (Bextra™), rofecoxib (Vioxx™), iguratimod (Careram™), IP 751 (Invedus), SC-58125 (Pharmacia) and etoricoxib (Arcoxia™). Yet further anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™). Yet further anti-angiogenesis agents include ABT 510 (Abbott), apratastat (TMI 005), AZD 8955 (AstraZeneca), incyclinide (Metastat™), and PCK 3145 (Proxyon).

Yet further anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In other embodiments, the additional anti-cancer agent is a so-called signal transduction inhibitor (e.g., inhibiting how regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors, EGF inhibitor, ErbB-1 (EGFR). ErbB-2, pan erb, IGF1R inhibitors, MEK, c-Kit inhibitors. FLT-3 inhibitors, K-Ras inhibitors, PI3 kinase inhibitors, JAK inhibitors, STAT inhibitors, Raf kinase inhibitors, Akt inhibitors, mTOR inhibitor. P70S6 kinase inhibitors, inhibitors of the WNT pathway and so called multi-targeted kinase inhibitors. Additional examples of signal transduction inhibitors which may be used in conjunction with a compound of the invention and pharmaceutical compositions described herein include BMS 214662 (Bristol-Myers Squibb), lonafamib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38). Other examples of signal transduction inhibitors include gefitinib (Iressa™), cetuximab (Erbitux™), erlotinib (Tarceva™), trastuzumab (Herceptin™), sunitinib (Sutent™), imatinib (Gleevec™), crizotinib (Pfizer), lorlatinib (Pfizer), dacomitinib (Pfizer), bosutinib (Pfizer), gedatolisib (Pfizer), canertinib (CI 1033), pertuzumab (Omnitarg™), lapatinib (Tycerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (1DM 1), mubritinib (TAK-165), CP-724,714 (Pfizer), panitumumab (Vectibix™), ARRY 142886 (Array Biopharm), everolimus (Certican™), zotarolimus (Endeavor™), temsirolimus (Torisel™), AP 23573 (ARIAD), and VX 680 (Vertex), XL 647 (Exelixis), sorafenib (Nexavar™), LE-AON (Georgetown University), and GI-4000 (Globelmmune). Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (Onc Bio), BMS 387032 (Bristol-Myers Squibb), palbociclib (Pfizer), and AG 024322 (Pfizer).

In other embodiments, the additional anti-cancer agent is a so called classical antineoplastic agent. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, DNA methyltransferase inhibitors, silencing agents or gene activating agents, ribonucleases, proteosomics, Topoisomerase I inhibitors, Camptothecin derivatives, Topoisomerase II inhibitors, alkylating agents, antimetabolites, poly(ADP-ribose) polymerase-1 (PARP-1) inhibitor (such as, e.g., talazoparib, olapariv, rucaparib, niraparib, iniparib, veliparib), microtubulin inhibitors, antibiotics, plant derived spindle inhibitors, platinum-coordinated compounds, gene therapeutic agents, antisense oligonucleotides, vascular targeting agents (VTAs), and statins. Examples of classical antineoplastic agents used in combination therapy with a compound of the invention, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi), Selective Estrogen-Receptor Downregulators (SERD's; such as fulvestrant), exemestane (Aromasin), anastrozole (Arimidex), atamestane, fadrozole, letrozole (Femara), formestane; gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), cyproterone, flutamide (Eulexin), megestrol, nilutamide (Nilandron), and osaterone, dutasteride, epristeride, finasteride. Serenoa repens, PHIL 00801, abarelix, goserelin, leuprorelin, triptorelin, bicalutamide, antiandrogen agents, such as enzalutamide, abiraterone acetate, bicalutamide (Casodex); and combinations thereof. Other examples of classical antineoplastic agents used in combination with a compound of the invention include but are not limited to suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan. SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, altretamine, AP-5280, apaziquone, brostallicin, bendamustine, busulfan, carboquone, carmustine, chlorambucil, dacarbazine, estramustine, fotemustine, glufosfamide, ifosfamide. KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

In still other embodiments, the additional anti-cancer agent is a so called dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda™), cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paciltaxel conjugate), cisplatin, carboplatin, Nedaplatin, oxaliplatin (Eloxatin), Satraplatin, Camptosar, capecitabine (Xeloda), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™—radiation therapy), bexarotene (Targretin™), Tesmilifene (DPPE—enhances efficacy of cytotoxics), Theratope™ (Biomira), Tretinoin (Vesanoid™), tirapazamine (Trizaone™), motexafin gadolinium (Xcytrin™) Cotara™ (mAb), and NBI-3001 (Protox Therapeutics), polyglutamate-paclitaxel (Xyotax™) and combinations thereof. Further examples of classical antineoplastic agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Provastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

In other embodiments, the additional anti-cancer agent is an epigenetic modulator, for example an inhibitor or EZH2, SMARCA4, PBRM1, ARID1A, ARID2, ARID1B, DNMT3A, TET2, MLL1/2/3, NSD1/2, SETD2, BRD4, DOT1L, HKMTsanti, PRMT1-9, LSD1, UTX. IDH1/2 or BCL6.

In further embodiments, the additional anti-cancer agent is an immunomodulatory agent, such as an inhibitor of CTLA-4, PD-1 or PD-L 1 (e.g., pembrolizumab, nivolumab or avelumab), LAG-3, TIM-3, TIGIT, 4-1BB, OX40, GITR, CD40, or a CAR-T-cell therapy.

In some embodiments, the additional anticancer agent is an EGFR inhibitor such as afatinib, osimertinib, lapatinib, erlotinib, dacomitinib, poziotinib, neratinib or gefitinib or an EGFR antibody such as cetuximab, panitumumab, or necitumumab.

Alternatively, a compound of the disclosure, a pharmaceutically acceptable salt thereof or a pharmaceutical composition disclosed herein can be administered in combination with other anti-cancer agents that are not EGFR inhibitors e.g., in combination with MEK, including mutant MEK inhibitors (trametinib, cobimtetinib, binimetinib, selumetinib, refametinib); c-MET, including mutant c-Met inhibitors (savolitinib, cabozantinib, foretinib) and MET antibodies (emibetuzumab); mitotic kinase inhibitors (CDK4/6 inhibitors such as palbociclib, ribociclib, abemacicilb); anti-angiogenic agents e.g., bevacizumab, nintedanib; apoptosis inducers such as Bcl-2 inhibitors e.g, venetoclax, obatoclax, navitoclax and Mcl-1 inhibitors e.g., AZD-5991, AMG-176, S-64315; and mTOR inhibitors e.g, rapamycin, temsirolimus, everolimus, ridoforolimus.

A compound of the disclosure, a pharmaceutically acceptable salt thereof or a pharmaceutical composition disclosed herein can also be administered in combination with an effective amount of a second agent selected from the group consisting of palbociclib (e.g., Ibrance®), ribociclib, abemaciclib, tamoxifen, letrozole, olaparib (e.g., Lynparza®), niraparib, carboplatin, cisplatin, paclitaxel, gemcitabine, megestrol acetate, medroxyprogesterone acetate, capecitabine (e.g., Xeloda®), regorafenib (e.g., Stivarga®), afatinib (e.g., Gilotrif®), osimertinib (e.g., Tagrisso®), gefitinib (e.g., Iressa®), erlotinib (e.g., Tarceva®), ramucirumab (e.g., Cyramza®), an EGFR inhibitor, pralsetinib, ABT-263 (navitoclax), MK-1775 (adavosertib), BAY-1895344, berzosertib, ceralasertib, SRA-737, LY2603618 (rabusertib), and trastuzumab (e.g., Herceptin®), or combinations thereof. The EGFR inhibitor may be selected from afatinib, osimertinib, lapatinib, erlotinib, dacomitinib, poziotinib, neratinib, gefitinib JBJ-04-125-02, alflutinib (AST 2818), aumolertinib (formerly almonertinib) (HS10296), BBT-176, BI-4020, BPI-361175, BPI-D0316, CH7233163, gilitertinib, icotinib, JND-3229, lazertinib, nazartinib (EGF 816), avitinib, PCC-0208027, rezivertinib (BPI-7711), TQB3804, zorifertinib (AZ-3759), or DZD9008; an EGFR antibody such as cetuximab, panitumumab, necitumumab, HLX07, JMT101; or a bispecific EGFR and MET antibody (e.g., amivantamab ((JNJ-61186372, JNJ-372)).

Biomarkers and Pharmacodynamics Markers

The disclosure further provides predictive markers (e.g., biomarkers and pharmacodynamic markers, e.g., gene copy number, gene sequence, expression levels, or phosphorylation levels) to identify those human subjects having, suspected of having, or at risk of developing a disease or disorder associated with CDK2 for whom administering a CDK2 inhibitor ("a CDK2 inhibitor" as used herein refers to a compound of the disclosure, or a pharmaceutically acceptable salt thereof) is likely to be effective.

CCNE1

In one embodiment, the biomarker is CCNE1. In particular an amplification of the cyclin E1 (CCNE1) gene and/or an expression level of CCNE1 in a biological sample would indicate that the patient or subject could benefit from administration of a compound of Formula (I) or a pharmaceutically acceptable salt thereof.

CCNE1 is a cell cycle factor essential for the control of the cell cycle at the G1/S transition (Ohtsubo et al., 1995, Mol. Cell. Biol. 15:2612-2624). CCNE1 acts as a regulatory subunit of CDK2, interacting with CDK2 to form a serine/threonine kinase holoenzyme complex. The CCNE1 subunit of this holoenzyme complex provides the substrate specificity of the complex (Honda et al., 2005, EMBO 24:452-463). CCNE1 is encoded by the cyclin E1 ("CCNE1") gene (GenBank Accession No. NM_001238). The amino acid sequence of human CCNE1 is found at GenBank Accession No NP_001229/UniProtKB Accession No P24864).

In one aspect, the present disclosure provides a method of treating a subject having, or at risk of developing, a disease or disorder associated with CDK2, comprising administering to the subject a therapeutically effective amount of a compound disclosed herein, or a pharmaceutically acceptable salt thereof, or a pharmaceutical composition disclosed herein, wherein the subject has an amplification of the CCNE1 gene and/or have an expression level of CCNE1 higher than a control expression level of CCNE1. In some embodiments, the disease or disorder associated with CDK2 is cancer.

Also provided herein is a method of treating a patient having an amplified expression level of CCNE1 and suffering from, or at risk of developing, a solid tumor cancer, comprising administering to the patient a therapeutically effective amount of a compound disclosed herein, or a pharmaceutically acceptable salt thereof, or a pharmaceutical composition disclosed herein.

An amplification of the CCNE1 gene and/or an expression level of CCNE1 that is higher than a control expression level of CCNE1 is indicative/predictive that a human subject having or at risk of developing a disease or disorder associated with CDK2 will respond to a CDK2 inhibitor in some embodiments, the expression level of CCNE1 may be the level of CCNE1 mRNA. In other embodiments, the expression level of CCNE1 may be the level of CCNE1 protein.

Other Biomarkers

In some embodiments, the contemplated biomarker may be p16 (also known as cyclin-dependent kinase inhibitor 2A, cyclin-dependent kinase 4 inhibitor A, multiple tumor suppressor 1, and p16-INK4a), which acts as a negative regulator of the proliferation of normal cells by interacting with CDK4 and CDK6. In other embodiments, the contemplated biomarker may be phosphorylation of Rb at the serine corresponding to amino acid position 780. Rb is a regulator of the cell cycle and acts as a tumor suppressor. Rb is activated upon phosphorylation by cyclin D-CDK4/6 at Ser780 and Ser795 and by cyclin E/CDK2 at Ser807 and Ser811.

The contemplated biomarker may also be selected from the group consisting of RB1, RBL1, RBL2, CDKN2A, CDKN1A, CDKN1B, FBXW7, CCNE1, CCNE2, CCNA1, CCNA2, CND1, CCND2, CCND3, CDK2, CDK3, CDK4, CDK6, CDKN2A, CDNK1A, CDKN1B E2F1, E2F2, E2F3, MYC, MYCL, MYCN, EZH2, ER, HER2, IER3, HPV+, and EGFR.

Biological Samples

Suitable biological samples for the methods described herein include any sample that contains blood or tumor cells obtained or derived from the human subject in need of treatment. For example, a biological sample can contain tumor cells from biopsy from a patient suffering from a solid tumor. A tumor biopsy can be obtained by a variety of means known in the art. Alternatively, a blood sample can be obtained from a patient suffering from a hematological cancer.

A biological sample can be obtained from a human subject having, suspected of having, or at risk of developing, a disease or disorder associated with CDK2. In some embodiments, the disease or disorder associated with CDK2 is a cancer (such as those described supra).

Methods for obtaining and/or storing samples that preserve the activity or integrity of molecules (e.g., nucleic acids or proteins) in the sample are well known to those skilled in the art. For example, a biological sample can be further contacted with one or more additional agents such as buffers and/or inhibitors, including one or more of nuclease, protease, and phosphatase inhibitors, which preserve or minimize changes in the molecules in the sample.

Methods of Administration and Dosage Forms

The precise amount of compound administered to provide an "effective amount" to the subject will depend on the mode of administration, the type, and severity of the cancer, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of Formula (I) being used by following, for example, dosages reported in the literature and recommended in the *Physician's Desk Reference* (57th Ed., 2003).

"Treating" or"treatment" refers to obtaining a desired pharmacological and/or physiological effect. The effect can be therapeutic, which includes achieving, partially or substantially, one or more of the following results: partially or substantially reducing the extent of the disease, condition or cancer; ameliorating or improving a clinical symptom or indicator associated with the disease, condition or cancer; delaying, inhibiting or decreasing the likelihood of the progression of the disease, condition or cancer; or decreasing the likelihood of recurrence of the disease, condition or cancer.

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

In addition, a compound of the disclosure, a pharmaceutically acceptable salt thereof or a pharmaceutical composition of the disclosure can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds of the disclosure, a pharmaceutically acceptable salt thereof or a pharmaceutical composition of the disclosure will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g. the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a disease using the disclosed CDK2 inhibitors for guidance.

The compounds of the disclosure or a pharmaceutically acceptable salt thereof can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the disclosure is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the disclosure or a pharmaceutically acceptable salt thereof may be incorporated with excipient and used in the form of ingestible tablets, buccal tablets, troches, capsules, elixirs, suspensions, syrups, wafers, and the like.

Typically for parenteral administration, solutions of a compound of the disclosure can generally or a pharmaceutically acceptable salt thereof be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound of the disclosure for the extemporaneous preparation of sterile injectable solutions or dispersions are appropriate.

The following examples are intended to be illustrative and are not intended to be limiting in any way to the scope of the disclosure.

EXEMPLIFICATION

Examples

Preparation of Exemplary Compounds

Definitions

TsOH 4-methylbenzenesulfonic acid
TEA triethylamine
THF tetrahydrofuran
MsCl methanesulfonyl chloride
DCM dichloromethane
$NH_4Cl$ ammonium chloride
$MgSO_4$ magnesium sulfate
$NaN_3$ sodium azide
DMF dimethyl formamide
EA ethyl acetate
$Na_2SO_4$ sodium sulfate
MeOH methanol
$N_2$ nitrogen
$H_2$ hydrogen
$LiAlH_4$ lithium aluminum hydride
$NaHCO_3$ sodium bicarbonate
CbzCl benzyl carbonochloridate
PE petroleum ether
DAST N-ethyl-N-(trifluoro-sulfanyl)ethanamine
HCl hydrochloride
ACN acetontirile
DIPEA diisopropylethylamine
DMSO dimethylsulfoxide
DMA dimethylacetamide
h hours
HPLC high performance liquid chromatography
min minutes
C Celsius
$IC_{50}$ inhibitory concentration 50%
IPA isopropyl alcohol
MTBE methyl tert-butyl ether
rt room temperature
TFA trifluoroacetic acid
IPA isopropyl alcohol Methods for preparing compounds of the invention can be carried out in suitable solvents which can be readily selected by one of skill in the art of organic synthesis. Suitable solvents can be substantially non-reactive with the starting materials (reactants), intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1H$ or $^{13}C$), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS: The liquid chromatography-mass spectrometry (LC-MS) data (sample analyzed for purity and identity) were obtained with an Agilent model-1260 LC system using an Agilent model 6120 mass spectrometer utilizing ES-API ionization fitted with an Agilent Poroshel 120 (EC-C18, 2.7 um particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

Alternatively, the liquid chromatography-mass spectrometry (LC-MS) data (sample analyzed for purity and identity) were obtained with a Shimadzu LCMS system using an Shimadzu LCMS mass spectrometer utilizing ESI ionization fitted with an Agilent (Poroshel HPH-C18 2.7 um particle size, 3.0×50 mm dimensions) reverse-phase column at 22.4 degrees Celsius. The mobile phase consisted of a mixture of solvent 5 mM $NH_4HCO_3$ (or 0.05% TFA) in water and acetonitrile. A constant gradient from 90% aqueous/10% organic to 5% aqueous/95% organic mobile phase over the course of 2 minutes was utilized. The flow rate was constant at 1.5 mL/min.

Prep LC-MS: Preparative HPLC was performed on a Shimadzu Discovery VP® Preparative system fitted with a Xtimate 10 um 150A 21.2×250 mm column at 22.4 degrees Celsius. Under basic conditions, the mobile phase consisted of a mixture of water (0.1% $NH_4HCO_3$) and ACN. A constant gradient from 85% aqueous/15% organic to 5% aqueous/95% organic over the course of 18 minutes was utilized. The flow rate was constant at 20 mL/min. Under acidic conditions, the mobile phase consisted of a mixture of water (0.1% FA) and ACN. A constant gradient from 65% aqueous/35% organic to 55% aqueous/45% organic over the course of 8 minutes was utilized.

Alternatively, the preparative HPLC was performed on a Waters Preparative system fitted with Column: XBridge Shield RP18 OBD Column, 30*150 mm, 5 um; The mobile phase consisted of a mixture of solvent Water (10 mmol/L $NH_4HCO_3$+0.05% $NH_3 \cdot H_2O$) and acetonitrile. A constant gradient from 95% aqueous/5% organic to 5% aqueous/95% organic mobile phase over the course of 11 minutes was utilized. The flow rate was constant at 60 mL/min. Reactions carried out in a microwave were done so in a Biotage Initiator microwave unit.

Silica gel chromatography: Silica gel chromatography was performed on a Teledyne Isco CombiFlash® Rf unit, a Biotage® Isolera Four unit, or a Biotage® Isolera Prime unit.

Proton NMR: $^1H$ NMR spectra were obtained with a Varian 400 MHz Unity Inova 400 MHz NMR instrument (acquisition time=3.5 seconds with a 1 second delay; 16 to 64 scans) or a Avance 400 MHz Unity Inova 400 MHz NMR instrument (acquisition time=3.99 seconds with a 1 second delay; 4 to 64 scans) or a Avance 300 MHz Unity Inova 300 MHz NMR instrument (acquisition time=5.45 seconds with a 1 second delay; 4 to 64 scans). Unless otherwise indicated, all protons were reported in DMSO-d6 solvent as parts-per million (ppm) with respect to residual DMSO (2.50 ppm).

Example 1. 3-fluoro-4-((4-(1-(2-hydroxy-2-methylpropyl)-1H-pyrazol-4-yl)-5-(trifluoromethyl)pyrimidin-2-yl)amino)benzenesulfonamide

Step 1. Synthesis of 1-(4-(2-chloro-5-(trifluoromethyl)pyrimidin-4-yl)-1H-pyrazol-1-yl)-2-methylpropan-2-ol (Intermediate 1)

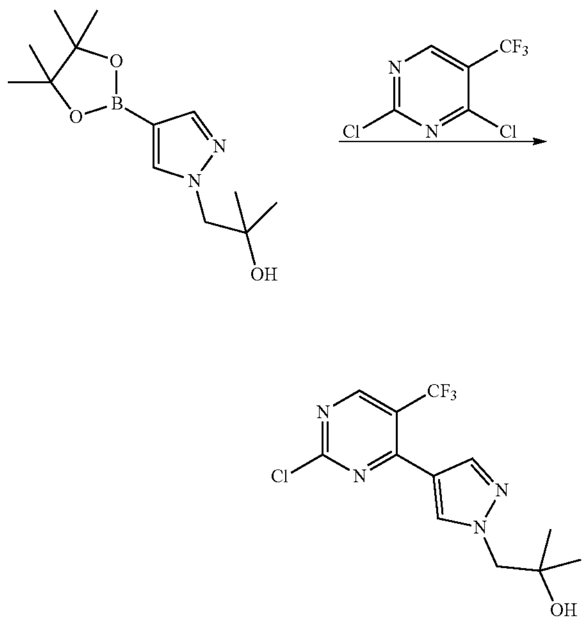

Intermediate 1

A mixture of 2-methyl-1-(4-(4,4,5,5-tetramethyl-1,3,2-dioxaborolan-2-yl)-1H-pyrazol-1-yl)propan-2-ol (1.0 g, 3.75 mmol), 2,4-dichloro-5-(trifluoromethyl)pyrimidine (2.4 g, 11.2 mmol), $Na_2CO_3$ (1.18 g, 11.2 mmol) and Pd(dppf)$Cl_2$ (306 mg, 375 μmol) in dioxane (20 mL) and $H_2O$ (5 mL) was stirred at 80° C. for 2 h under $N_2$. LCMS indicated completion of the reaction. The reaction mixture was concentrated, and the residue was purified by flash chromatography on silica gel eluting with EA/PE (1/4) to afford the title compound (400 mg, 33% yield) as a yellow solid. MS (ES+) $C_{12}H_{12}ClF_3N_4O$ requires; 320, found: 321 $[M+H]^+$.

Step 2. Synthesis of 3-fluoro-4-((4-(1-(2-hydroxy-2-methylpropyl)-1H-pyrazol-4-yl)-5-(trifluoromethyl)pyrimidin-2-yl)amino)benzenesulfonamide (Compound 1)

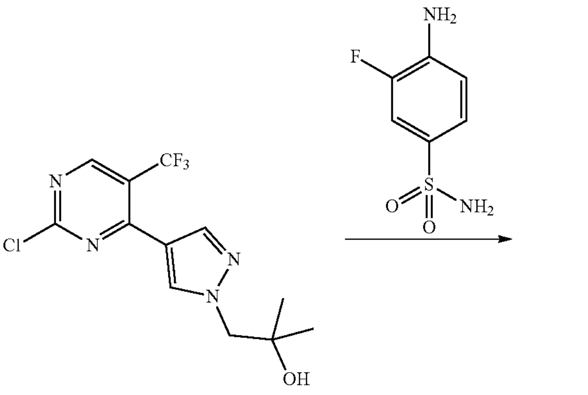

Intermediate 1

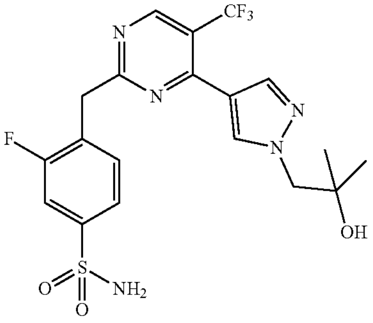

1

To a mixture of Intermediate 1 (40 mg, 124 μmol) and 4-amino-3-fluorobenzenesulfonamide (23.5 mg, 124 μmol) in IPA (2 mL) was added TsOH (21.3 mg, 124 μmol), then stirred at 90° C. for 16 h. LCMS indicated completion of the reaction. The reaction mixture was purified by Prep-HPLC (Mobile phase: A=water(0.1% $NH_4HCO_3$), B=acetonitrile; Gradient: B=15%-95% in 18 min; Column: Xtimate 10 um 150A 21.2×250 mm) to give the title compound (32.2 mg, 54% yield) as a white solid. MS (ES+) $C_{18}H_{18}F_4N_6O_3S$ requires: 474, found: 475 $[M+H]^+$. $^1H$-NMR (400 MHz, DMSO-$d_6$) δ ppm 8.77 (s, 1H), 8.25 (s, 1H), 8.02 (t, J=8.4 Hz, 1H), 7.95 (s, 1H), 7.70-7.67 (m, 2H), 7.45 (br. s., 1H), 4.80 (s, 1H), 4.12 (s, 2H), 1.08 (s, 6H).

Example 2. 4-((4-(1-(2-hydroxy-2-methylpropyl)-1H-pyrazol-4-yl)-5-(trifluoromethyl)pyrimidin-2-yl)amino)-3-methylbenzenesulfonamide

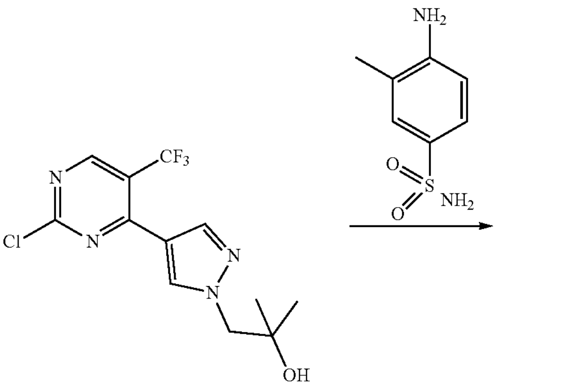

-continued

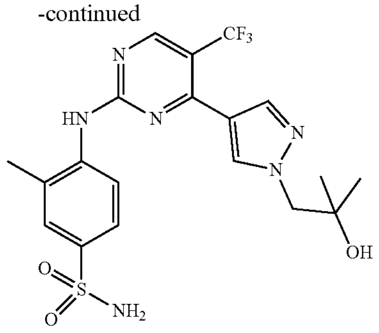

To a mixture of Intermediate 1 (140 mg, 436 μmol) and 4-amino-3-methylbenzenesulfonamide (81.1 mg, 436 μmol) in IPA (10 mL) was added TsOH (75.0 mg, 436 μmol), then stirred at 90° C. for 16 h. LCMS indicated completion of the reaction. The reaction mixture was purified by Prep-HPLC (Mobile phase: A=water(0.1% $NH_4HCO_3$). B=acetonitrile; Gradient: B=15%-95% in 18 min; Column: Xtimate 10 um 150A 21.2x250 mm) to give the title compound (46.3 mg, 22% yield) as a white solid. MS (ES+) $C_{19}H_{21}F_3N_6O_3S$ requires: 470, found: 471 $[M+H]^+$. $^1$H-NMR (400 MHz, DMSO-$d_6$) δ ppm 9.68 (s, 1H), 8.70 (s, 1H), 8.22 (s, 1H), 7.91 (s, 1H), 7.75-7.68 (m, 3H), 7.28 (s, 2H), 4.77 (s, 1H), 4.11 (s, 2H), 2.34 (s, 3H), 1.08 (s, 6H).

Example 3. 4-((5-chloro-4-(1-(2-hydroxy-2-methylpropyl)-1H-pyrazol-4-yl)pyrimidin-2-yl)amino)benzenesulfonamide

Step 1. Synthesis of 1-(4-(2,5-dichloropyrimidin-4-yl)-1H-pyrazol-1-yl)-2-methylpropan-2-ol (Intermediate 2)

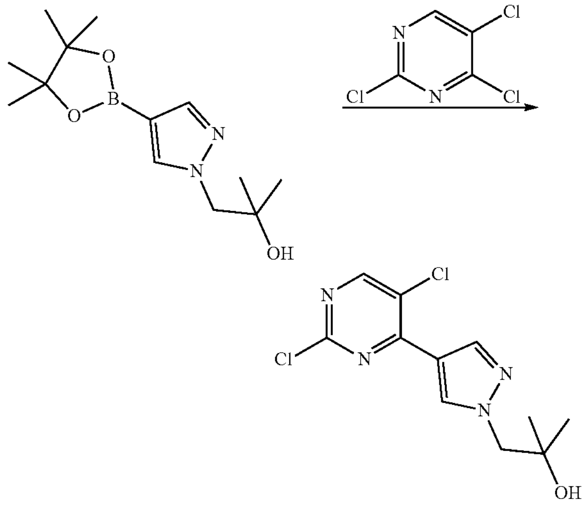

Intermediate 2

A mixture of 2-methyl-1-(4-(4,4,5,5-tetramethyl-1,3,2-dioxaborolan-2-yl)-1H-pyrazol-1-yl)propan-2-ol (200 mg, 751 μmol), 2,4,5-trichloropyrimidine (137 mg, 751 μmol), $Na_2CO_3$ (279 mg, 2.25 mmol) and Pd(dppf)$Cl_2$ (61.3 mg, 75.1 μmol) in dioxane (10 mL) and $H_2O$ (2.5 mL) was stirred at 80° C. for 2 h under $N_2$. LCMS indicated completion of the reaction. The reaction mixture was concentrated and the residue was purified by flash chromatography on silica gel eluting with EA/PE (2/1) to afford the title compound (200 mg, 93% yield) as a white solid. MS (ES+) $C_{11}H_{12}C_{12}N_4O$ requires: 286, found: 287 [M+H]+.

Step 2. Synthesis of 4-((5-chloro-4-(1-(2-hydroxy-2-methylpropyl)-1H-pyrazol-4-yl)pyrimidin-2-yl)amino)benzenesulfonamide (Example 3)

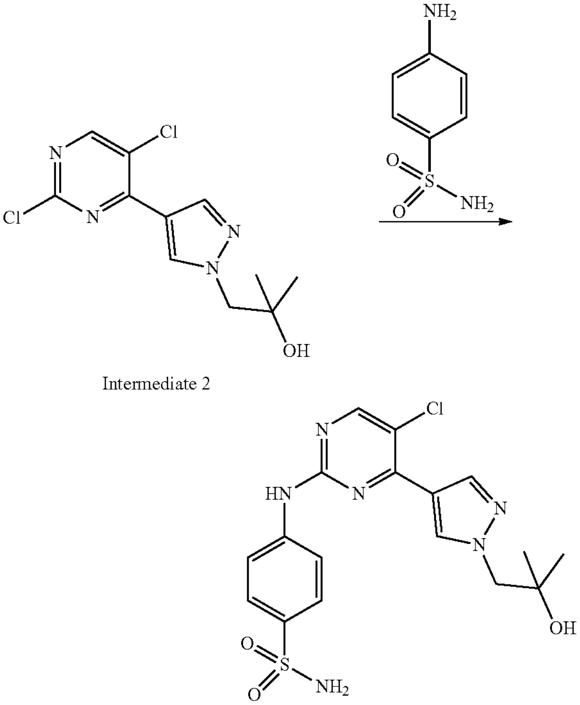

To a mixture of Intermediate 2 (140 mg, 436 μmol) and 4-aminobenzenesulfonamide (100 mg, 584 μmol) in IPA (5 mL) was added TsOH (167 mg, 974 μmol), then the reaction stirred at 90° C. for 16 h. LCMS indicated completion of the reaction. The reaction mixture was purified by Prep-HPLC (basic conditions) to give the title compound (25.9 mg, 12% yield) as a white solid. MS (ES+) $C_{19}H_{21}F_3N_6O_3S$ requires: 422, found: 423 $[M+H]^+$. $^1$H-NMR (400 MHz, DMSO-$d_6$) δ ppm 10.16 (s, 1H), 8.59 (s, 1H), 8.58 (s, 1H), 8.27 (s, 11H), 7.93 (d, J=8.8 Hz, 2H), 7.78 (d, J=8.8 Hz, 2H), 7.19 (s, 2H), 4.81 (s, 1H), 4.16 (s, 2H), 1.11 (s, 6H).

Example 4. 4-((5-(difluoromethyl)-4-(1-(2-hydroxy-2-methylpropyl)-1H-pyrazol-4-yl)pyrimidin-2-yl)amino)benzenesulfonamide

Step 1: Synthesis of 2,4-dichloro-5-(difluoromethyl)pyrimidine (Intermediate 3)

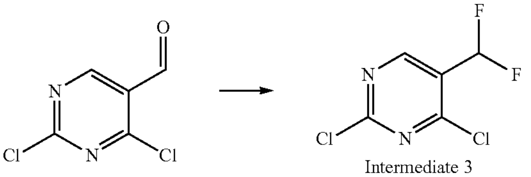 [SMILES: O=Cc1cnc(Cl)nc1Cl ; FC(F)c1cnc(Cl)nc1Cl]

Intermediate 3

To a solution of 2,4-dichloropyrimidine-5-carbaldehyde (500 mg, 2.84 mmol) in DCM (10 mL) was added DAST (914 mg, 5.68 mmol) and the reaction stirred at rt for 14 h. LCMS indicated completion of the reaction. The reaction mixture was concentrated and the residue was purified by flash chromatography on silica gel eluting with PE/EA (20/1) to afford the title compound (450 mg, 80% yield) as a colorless oil. $^1$H-NMR (400 MHz, $CDCl_3$) δ ppm 8.82 (s, 1H), 6.90 (t, J=53.6 Hz, 1H).

Step 2: Synthesis of 1-(4-(2-chloro-5-(difluoromethyl)pyrimidin-4-yl)-1H-pyrazol-1-yl)-2-methylpropan-2-ol (Intermediate 4)

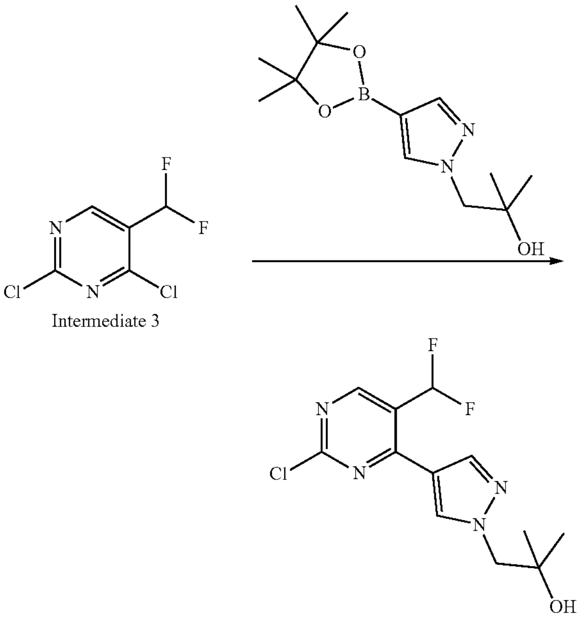

Intermediate 3

Intermediate 4

The title compound was obtained as a light yellow solid, 200 mg, 65% yield, from 2-methyl-1-(4-(4,4,5,5-tetramethyl-1,3,2-dioxaborolan-2-yl)-1H-pyrazol-1-yl)propan-2-ol and Intermediate 3, following a similar procedure to that described in Example 3, step 1. MS (ES+) $C_{12}H_{13}ClF_2N_4O$ requires: 302, found: 303 $[M+H]^+$.

Step 3. Synthesis of 4-((5-(difluoromethyl)-4-(1-(2-hydroxy-2-methylpropyl)-1H-pyrazol-4-yl)pyrimidin-2-yl)amino)benzenesulfonamide (Example 4)

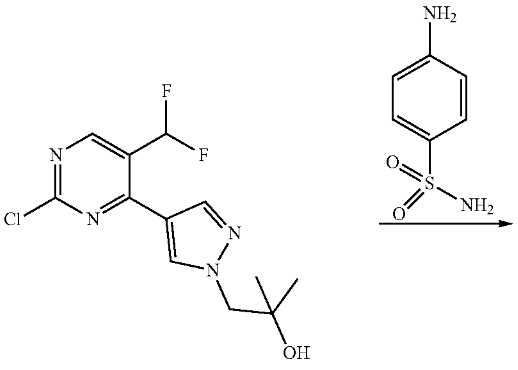

Intermediate 4

-continued

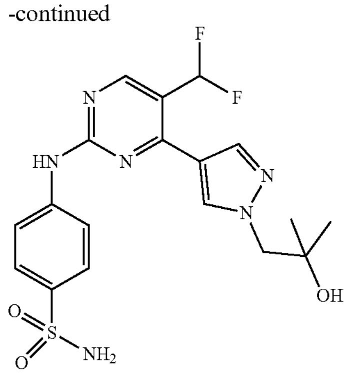

To a mixture of Intermediate 4 (200 mg, 0.66 mmol) and 4-aminobenzenesulfonamide (114 mg, 0.66 mmol) in IPA (3 mL) was added TsOH (114 mg, 0.66 mmol), then the reaction stirred at 90° C. for 16 h. LCMS indicated completion of the reaction. The reaction mixture was purified by Prep-HPLC (basic conditions) to give the title compound (83.6 mg, 28% yield) as a white solid. MS (ES+) $C_{18}H_{20}F_2N_6O_3S$ requires: 438, found: 439 $[M+H]^+$. $^1$H-NMR (400 MHz, DMSO-$d_6$) δ ppm 10.38 (br. s, 1H), 8.72 (s, 1H), 8.31 (s, 1H), 8.05 (s, 1H), 7.98 (d, J=8.8 Hz, 2H), 7.79 (d, J=8.8 Hz, 2H), 7.24 (t, J=54.4 Hz, 1H), 4.84 (s, 1H), 4.14 (s, 2H), 1.11 (s, 6H).

Example 5. 4-((4-(1-(2-hydroxy-2-methylpropyl)-1H-pyrazol-4-yl)-5-(trifluoromethyl)pyrimidin-2-yl)amino)benzenesulfonamide

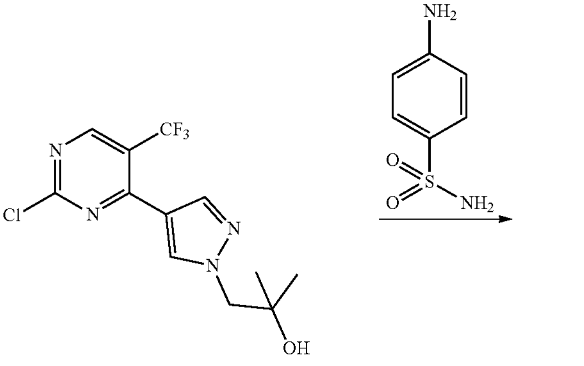

Intermediate 1

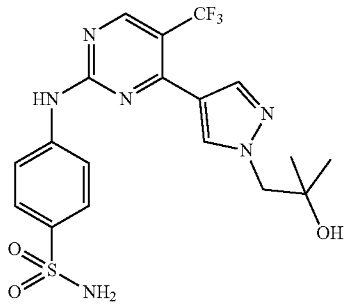

The title compound was obtained as a white solid, 19.2 mg, 45% yield, from Intermediate 1 and 4-aminobenzenesulfonamide, following a similar procedure to that described in Example 4, step 3. MS (ES+) $C_{18}H_{19}F_3N_6O_3S$ requires:

456, found: 457 $[M+H]^+$. $^1H$-NMR (400 MHz, DMSO-$d_6$) δ ppm 10.55 (br. s, 1H), 8.82 (s, 1H), 8.32 (s, 1H), 8.03 (s, 1H), 7.96 (d, J=8.8 Hz, 2H), 7.80 (d, J=8.8 Hz, 2H), 7.21 (br. s, 2H), 4.83 (s, 1H), 4.15 (s, 2H), 1.10 (s, 6H).

Example 6. (S)-3-fluoro-4-((4-(1-(3-hydroxy-3-methylbutan-2-yl)-1H-pyrazol-4-yl)-5-(trifluoromethyl)pyrimidin-2-yl)amino)benzenesulfonamide or (R)-3-fluoro-4-((4-(1-(3-hydroxy-3-methylbutan-2-yl)-1H-pyrazol-4-yl)-5-(trifluoromethyl)pyrimidin-2-yl)amino)benzenesulfonamide Step 1. Synthesis of 3-(4-(4,4,5,5-tetramethyl-1,3,2-dioxaborolan-2-yl)-1H-pyrazol-1-yl)butan-2-one (Intermediate 5)

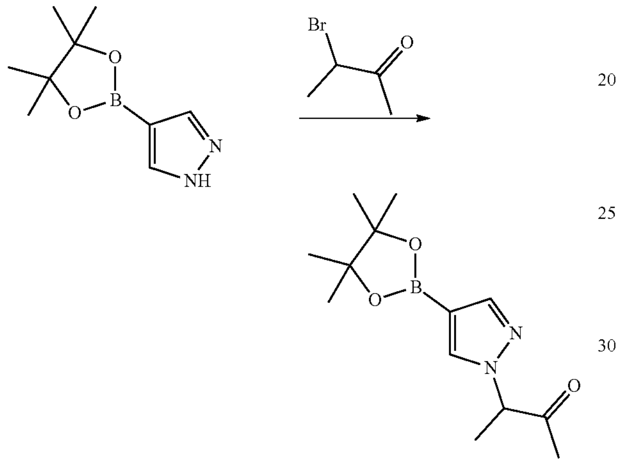

Intermediate 5

A mixture of 4-(4,4,5,5-tetramethyl-1,3,2-dioxaborolan-2-yl)-1H-pyrazole (4.00 g, 20.6 mmol) and NaH (60%, 880 mg, 22.7 mmol) in dry DMF (200 mL) was stirred at 0° C. to rt for 20 min. 3-Bromobutan-2-one (3.76 g, 24.90 mmol) was added at 0° C. and the resulting mixture was stirred at 120° C. for 6 h. The mixture was cooled to rt and water and EA were added. The aqueous layer was extracted with EA, and the combined EA layers were washed with water and concentrated in vacuo. The residue was purified by flash chromatography on silica gel eluting with EA/PE=1/3 to afford the title product as an oil (4.80 g, 88% yield). MS (ES+) $C_{13}H_{21}BN_2O_3$ requires: 264, found: 265$[M+H]^+$.

Step 2. Synthesis of 3-(4-(2-chloro-5-(trifluoromethyl)pyrimidin-4-yl)-1H-pyrazol-1-yl)butan-2-one (Intermediate 6)

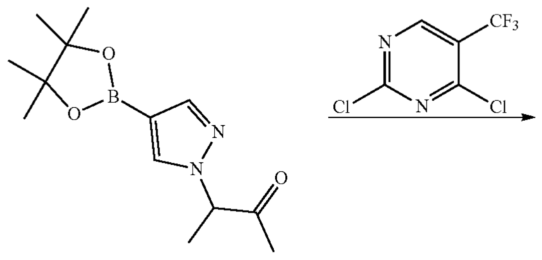

Intermediate 5

-continued

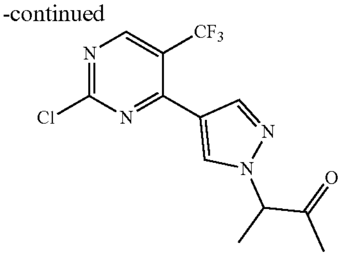

Intermediate 6

Under $N_2$, a mixture of 2,4-dichloro-5-(trifluoromethyl) pyrimidine (2.05 g, 9.45 mmol), Intermediate 5 (1.25 g, 4.72 mmol), Pd(dppf)$Cl_2$ (192 mg, 0.24 mmol) and $Na_2CO_3$ (751 mg, 7.09 mmol) in dioxane (30 mL) and water (7.5 mL) was heated at 90° C. for 16 h. It was concentrated in vacuo and the aqueous residue was extracted with EA. The combined EA layers were concentrated in vacuo. The residue was purified by flash chromatography on silica gel eluting with EA/PE=1/1 to give the title product as an oil (200 mg, 13% yield). MS (ES+) $C_{12}H_{10}ClF_3N_4O$ requires: 318, found: 319 $[M+H]^+$.

Step 3. Synthesis of (R)-3-(4-(2-chloro-5-(trifluoromethyl)pyrimidin-4-yl)-1H-pyrazol-1-yl)-2-methylbutan-2-ol and (S)-3-(4-(2-chloro-5-(trifluoromethyl)pyrimidin-4-yl)-1H-pyrazol-1-yl)-2-methylbutan-2-ol (Intermediate 7 and Intermediate 8)

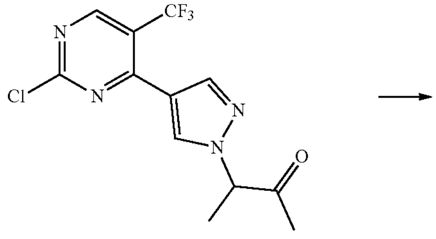

Intermediate 6

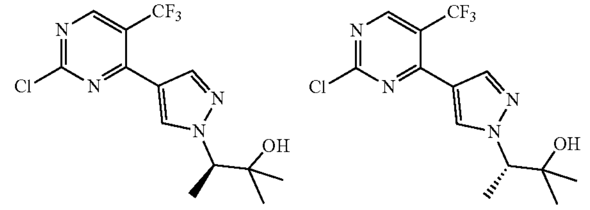

Intermediate 7 Intermediate 8

At 0° C., to a mixture of Intermediate 6 (800 mg, 2.51 mmol) in THF (5 mL) was added MeMgBr (3 M, 2 mL, 6 mmol) and the reaction stirred at 0° C. to rt for 2 h. Saturated aqueous $NH_4Cl$ was added at 0° C. and the resulting mixture was extracted with EA. The combined EA layers were concentrated in vacuo. The resulting residue was purified by flash chromatography on silica gel eluting with EA/PE=2/1 to give 3-(4-(2-chloro-5-(trifluoromethyl)pyrimidin-4-yl)-1H-pyrazol-1-yl)-2-methylbutan-2-ol. MS (ES+) $C_{13}H_{14}ClF_3N_4O$ requires: 334, found: 335 $[M+H]^+$. This racemic product was separated by chiral-SFC, Column: AD 20*250 mm, 10 um (Daicel), Column temperature: 35° C. Mobile phase: $CO_2$/MeOH (0.2% Methanol Ammonia)=60/

40, Flow rate: 80 g/min, to afford peak 1, Intermediate 7, 214 mg, (R)-3-(4-(2-chloro-5-(trifluoromethyl)pyrimidin-4-yl)-1H-pyrazol-1-yl)-2-methylbutan-2-ol or (S)-3-(4-(2-chloro-5-(trifluoromethyl)pyrimidin-4-yl)-1H-pyrazol-1-yl)-2-methylbutan-2-ol.

Further elution provided peak 2, Intermediate 8, 200 mg, as a white solid, (S)-3-(4-(2-chloro-5-(trifluoromethyl)pyrimidin-4-yl)-1H-pyrazol-1-yl)-2-methylbutan-2-ol or (R)-3-(4-(2-chloro-5-(trifluoromethyl)pyrimidin-4-yl)-1H-pyrazol-1-yl)-2-methylbutan-2-ol.

Step 4. Synthesis of (S)-3-fluoro-4-((4-(1-(3-hydroxy-3-methylbutan-2-yl)-1H-pyrazol-4-yl)-5-(trifluoromethyl)pyrimidin-2-yl)amino)benzenesulfonamide or (R)-3-fluoro-4-((4-(1-(3-hydroxy-3-methylbutan-2-yl)-1H-pyrazol-4-yl)-5-(trifluoromethyl)pyrimidin-2-yl)amino) benzenesulfonamide (Example 6)

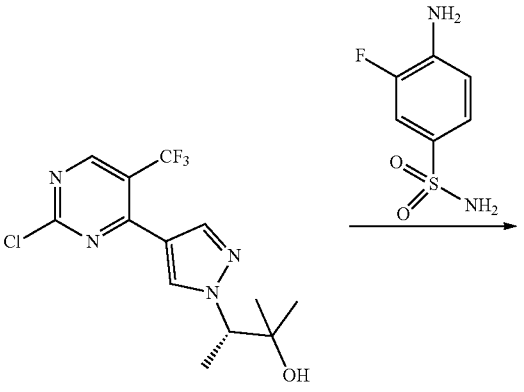

Intermediate 8

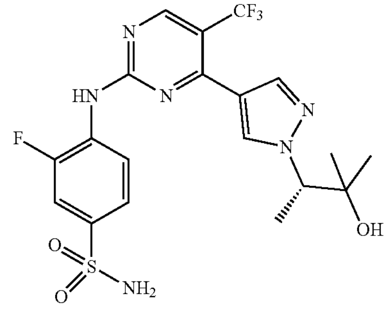

The title compound was obtained as a white solid, 80.2 mg, 27% yield, from Intermediate 8 and 4-amino-3-fluorobenzene-1-sulfonamide following a similar procedure to that described in Example 4, step 3. MS (ES+) $C_{19}H_{20}F_4N_6O_3S$ requires: 488, found: 489 $[M+H]^+$. $^1H$ NMR (400 MHz, DMSO) δ 10.08 (s, 1H), 8.76 (s, 1H), 8.26 (s, 1H), 8.02 (t, J=8.0 Hz, 1H), 7.94 (s, 1H), 7.69 (s, 1H), 7.67 (s, 1H), 7.45 (s, 2H), 4.76 (s, 1H), 4.34 (q, J=7.0 Hz, 1H), 1.46 (d, J=7.0 Hz, 3H), 1.07 (s, 3H), 1.02 (s, 3H).

Example 7. (R)-3-fluoro-4-((4-(1-(3-hydroxy-3-methylbutan-2-yl)-1H-pyrazol-4-yl)-5-(trifluoromethyl)pyrimidin-2-yl)amino)benzenesulfonamide or (S)-3-fluoro-4-((4-(1-(3-hydroxy-3-methylbutan-2-yl)-1H-pyrazol-4-yl)-5-(trifluoromethyl)pyrimidin-2-yl)amino)benzenesulfonamide

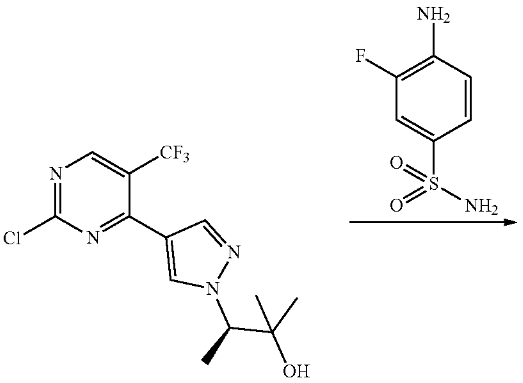

Intermediate 7

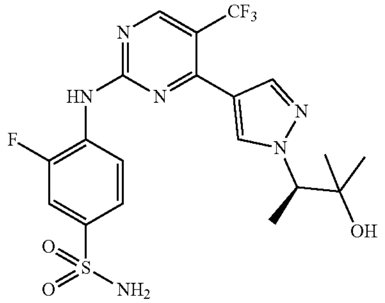

The title compound was obtained as a white solid, 68.2 mg, 22% yield, from Intermediate 7 and 4-amino-3-fluorobenzene-1-sulfonamide following a similar procedure to that described in Example 4, step 3. MS (ES+) $C_{19}H_{20}F_4N_6O_3S$ requires: 488, found: 489 $[M+H]^+$. $^1H$ NMR (400 MHz, DMSO) δ 10.08 (s, 1H), 8.76 (s, 1H), 8.26 (s, 1H), 8.02 (t, J=8.0 Hz, 1H), 7.94 (s, 1H), 7.69 (s, 1H), 7.67 (s, 1H), 7.45 (s, 2H), 4.76 (s, 1H), 4.34 (q, J=7.0 Hz, 1H), 1.46 (d, J=7.0 Hz, 3H), 1.07 (s, 3H), 1.02 (s, 3H).

Example 8. 4-((5-cyano-4-(1-(2-hydroxy-2-methylpropyl)-1H-pyrazol-4-yl)pyrimidin-2-yl)amino)benzenesulfonamide Step 1. Synthesis of 4-((4-chloro-5-cyanopyrimidin-2-yl)amino)benzenesulfonamide

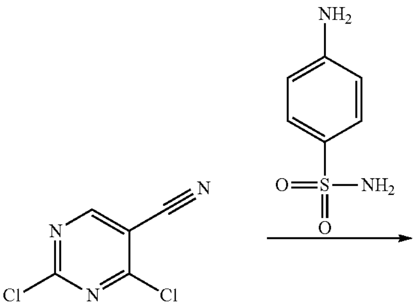

-continued

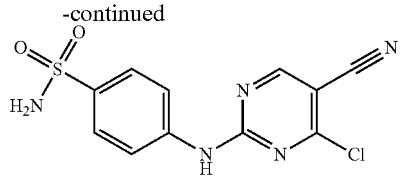

Intermediate 9

To a mixture of 2,4-dichloropyrimidine-5-carbonitrile (10.0 g, 57.5 mmol) and 4-aminobenzenesulfonamide (9.90 g, 57.5 mmol) in IPA (100 mL) was added DIPEA (11.1 g, 86.2 mmol) in one portion at 25° C. The mixture was stirred at 50° C. for 1 h. The reaction mixture was filtered and concentrated under reduced pressure to give a residue. The combined crude product was purified by Prep-HPLC (acidic condition) to yield the title compound (3.0 g) as a yellow solid.

Step 2. Synthesis of 4-((5-cyano-4-(1-(2-hydroxy-2-methylpropyl)-1H-pyrazol-4-yl)pyrimidin-2-yl) amino benzenesulfonamide (Example 8)

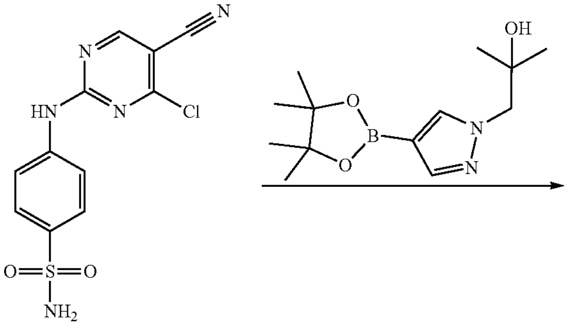

Intermediate 9

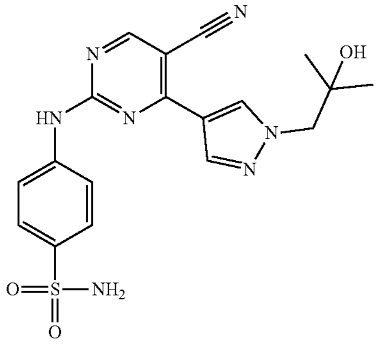

To a mixture of Intermediate 9 (74.3 mg, 0.240 mmol) in DMF (3.0 mL) was added 2-methyl-1-(4-(4,4,5,5-tetramethyl-1,3,2-dioxaborolan-2-yl)-1H-pyrazol-1-yl)propan-2-ol (95.7 mg, 0.360 mmol), $Cs_2CO_3$ (312 mg, 0.960 mmol), $H_2O$ (0.5 mL) and Pd(dppf)$Cl_2$ (12.0 μmol) under $N_2$ atmosphere. The reaction mixture was stirred at 100° C. for 16 h. LCMS indicated completion of the reaction. The mixture was filtered and the solvent removed in vacuo. The residue was purified by Prep-HPLC (Acidic conditions) to give the title compound (36.8 mg, 37%). MS (ES+) $C_{18}H_{19}N_7O_3S$ requires: 413.5, found: 414.1 [M+H]+. 1H NMR (500 MHz, DMSO) δ 10.59 (s, 1H), 8.85 (d, J=1.7 Hz, 1H), 8.53 (s, 1H), 8.22 (s, 1H), 7.92-7.84 (m, 2H), 7.80-7.71 (m, 2H), 7.18 (s, 2H), 4.77 (d, J=1.7 Hz, 1H), 4.11 (s, 2H), 1.05 (s, 6H).

Example 9. Synthesis of 3-fluoro-4-((4-(1-((2S,3S)-3-hydroxybutan-2-yl)-1H-pyrazol-4-yl)-5-(trifluoromethyl)pyrimidin-2-yl)amino)benzenesulfonamide or 3-fluoro-4-((4-(1-((2R,3R)-3-hydroxybutan-2-yl)-1H-pyrazol-4-yl)-5-(trifluoromethyl)pyrimidin-2-yl) amino)benzenesulfonamide or 3-fluoro-4-((4-(1-((2R,3S)-3-hydroxybutan-2-yl)-1H-pyrazol-4-yl)-5-(trifluoromethyl)pyrimidin-2-yl)amino) benzenesulfonamide or 3-fluoro-4-((4-(1-((2S,3R)-3-hydroxybutan-2-yl)-1H-pyrazol-4-yl)-5-(trifluoromethyl)pyrimidin-2-yl)amino) benzenesulfonamide Step 1. Synthesis of 3-(4-(4,4,5,5-tetramethyl-1,3,2-dioxaborolan-2-yl)-1H-pyrazol-1-yl)butan-2-ol (Intermediate 10)

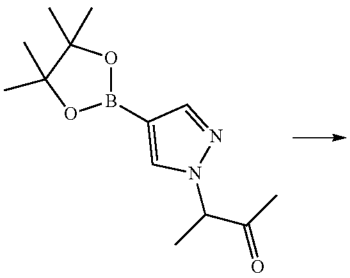

Intermediate 5

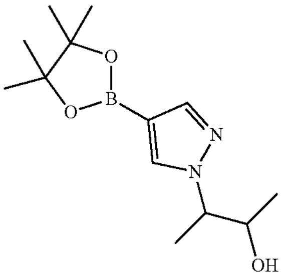

Intermediate 10

To a solution of Intermediate 5 (2 g, 7.57 mmol) in MeOH (20 mL) was added $NaBH_4$ (427 mg, 11.3 mmol) and the reaction stirred at rt for 30 min. LCMS indicated completion of the reaction. The reaction was quenched with water and extracted with DCM. The combined organic layer was washed with water and brine, dried over sodium sulfate, filtered and concentrated. The residue was purified by flash chromatography on silica gel eluting with PE/EA (1/1) to afford the title compound (1.2 g, 59% yield) as a colorless oil. MS (ES+) $C_{13}H_{23}BN_2O_3$ requires: 266, found: 267 [M+H].

Step 2. Synthesis of (2R,3R)-3-(4-(2-amino-5-(trifluoromethyl)pyrimidin-4-yl)-1H-pyrazol-1-yl)butan-2-ol, (2S,3S)-3-(4-(2-amino-5-(trifluoromethyl)pyrimidin-4-yl)-1H-pyrazol-1-yl)butan-2-ol, (2R,3S)-3-(4-(2-amino-5-(trifluoromethyl)pyrimidin-4-yl)-1H-pyrazol-1-yl)butan-2-ol and (2S,3R)-3-(4-(2-amino-5-(trifluoromethyl)pyrimidin-4-yl)-1H-pyrazol-1-yl)butan-2-ol (Intermediates 12-P1, 12-P2, 13-P1 and 13-P2)

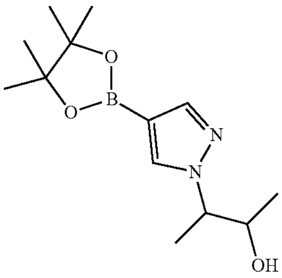

Intermediate 10

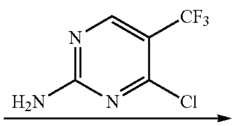

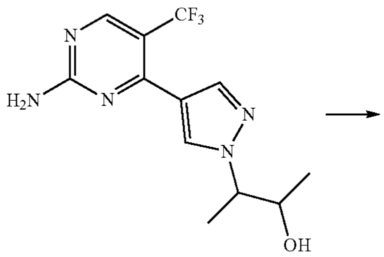

Intermediate 11

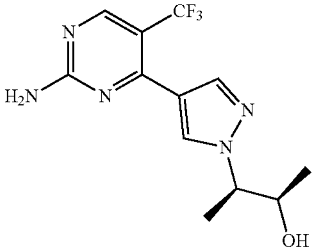

Cis racemate
Intermediate 12

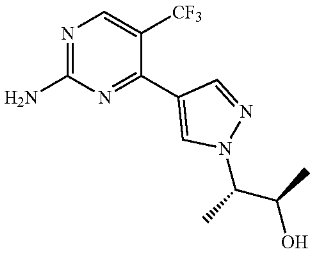

Trans Racemate
Intermediate 13

-continued

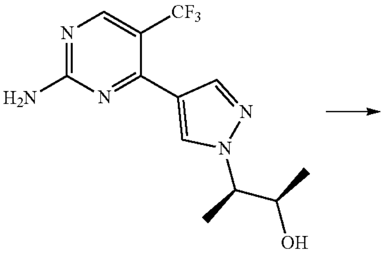

Intermediate 12

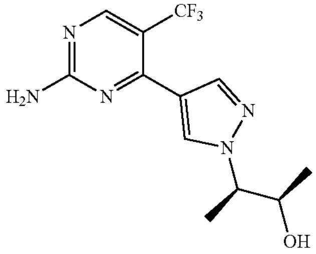

Intermediate 12-P1

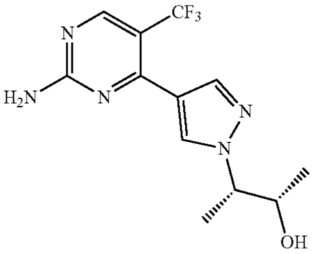

Intermediate 12-P2

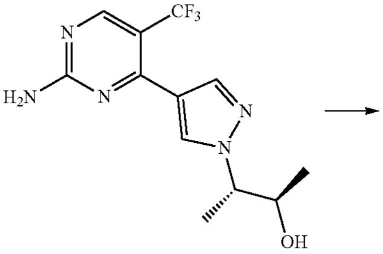

Intermediate 13

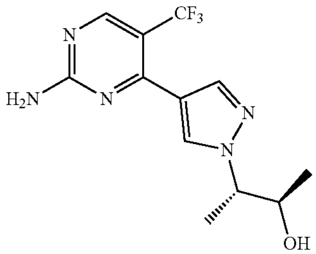

Intermediate 13-P1

-continued

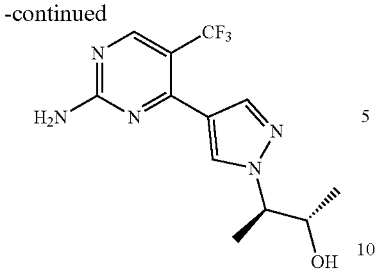

Intermediate 13-P2

A mixture of Intermediate 10 (1 g, 3.75 mmol), 4-chloro-5-(trifluoromethyl)pyrimidin-2-amine (740 mg, 3.75 mmol), $Na_2CO_3$ (1.09 g, 11.2 mmol) and Pd(dppf)$Cl_2$ (275 mg, 375 μmol) in dioxane (15 mL) and $H_2O$ (4 mL) was stirred at 90° C. overnight under $N_2$. LCMS indicated completion of the reaction. The residue was purified by flash chromatography on silica gel eluting with EA/PE (1/1) and then by Prep-HPLC (Basic Conditions) to give 3-(4-(2-amino-5-(trifluoromethyl)pyrimidin-4-yl)-1H-pyrazol-1-yl)butan-2-ol (800 mg, 71% yield). This product (800 mg) was separated by chiral-HPLC to afford Peak 1, Intermediate 12, cis-rac-(2R,3R)-3-(4-(2-amino-5-(trifluoromethyl)pyrimidin-4-yl)-1H-pyrazol-1-yl)butan-2-ol or (280 mg) trans-rac-(2R,3S)-3-(4-(2-amino-5-(trifluoromethyl)pyrimidin-4-yl)-1H-pyrazol-1-yl)butan-2-ol and Peak 2, Intermediate 13, trans-rac-(2R,3S)-3-(4-(2-amino-5-(trifluoromethyl)pyrimidin-4-yl)-1H-pyrazol-1-yl)butan-2-ol or cis-rac-(2R,3R)-3-(4-(2-amino-5-(trifluoromethyl)pyrimidin-4-yl)-1H-pyrazol-1-yl)butan-2-ol (350 mg).

Intermediate 12 (280 mg) was separated by chiral-SFC (Column: IG 20*250 mm, 10 um (Daicel); Column temperature: 35° C.; Mobile phase: CO2/MeOH (0.2% Methanol Ammonia)=80/20; Flow rate: 100 g/min to afford Intermediate 12-P1 (110 mg), (2R,3R)-3-(4-(2-amino-5-(trifluoromethyl)pyrimidin-4-yl)-1H-pyrazol-1-yl)butan-2-ol or (2S,3S)-3-(4-(2-amino-5-(trifluoromethyl)pyrimidin-4-yl)-1H-pyrazol-1-yl)butan-2-ol or (2R,3S)-3-(4-(2-amino-5-(trifluoromethyl)pyrimidin-4-yl)-1H-pyrazol-1-yl)butan-2-ol or (2S,3R)-3-(4-(2-amino-5-(trifluoromethyl)pyrimidin-4-yl)-1H-pyrazol-1-yl)butan-2-ol and Intermediate 12-P2 (100 mg), (2S,3S)-3-(4-(2-amino-5-(trifluoromethyl)pyrimidin-4-yl)-1H-pyrazol-1-yl)butan-2-ol or (2R,3R)-3-(4-(2-amino-5-(trifluoromethyl)pyrimidin-4-yl)-1H-pyrazol-1-yl)butan-2-ol or (2R,3S)-3-(4-(2-amino-5-(trifluoromethyl)pyrimidin-4-yl)-1H-pyrazol-1-yl)butan-2-ol or (2S,3R)-3-(4-(2-amino-5-(trifluoromethyl)pyrimidin-4-yl)-1H-pyrazol-1-yl)butan-2-ol as a white solid.

Intermediate 13 (350 mg) was separated by chiral-SFC (Column: IG 20*250 mm, 10 um (Daicel); Column temperature: 35° C.; Mobile phase: CO2/MeOH (0.2% Methanol Ammonia)=80/20; Flow rate: 100 g/min, to afford Intermediate 13-P1 (140 mg), (2R,3S)-3-(4-(2-amino-5-(trifluoromethyl)pyrimidin-4-yl)-1H-pyrazol-1-yl)butan-2-ol or (2S,3R)-3-(4-(2-amino-5-(trifluoromethyl)pyrimidin-4-yl)-1H-pyrazol-1-yl)butan-2-ol or (2R,3R)-3-(4-(2-amino-5-(trifluoromethyl)pyrimidin-4-yl)-1H-pyrazol-1-yl)butan-2-ol or (2S,3S)-3-(4-(2-amino-5-(trifluoromethyl)pyrimidin-4-yl)-1H-pyrazol-1-yl)butan-2-ol, and Intermediate 13-P2 (190 mg), (2S,3R)-3-(4-(2-amino-5-(trifluoromethyl)pyrimidin-4-yl)-1H-pyrazol-1-yl)butan-2-ol or (2R,3S)-3-(4-(2-amino-5-(trifluoromethyl)pyrimidin-4-yl)-1H-pyrazol-1-yl)butan-2-ol or (2R,3R)-3-(4-(2-amino-5-(trifluoromethyl)pyrimidin-4-yl)-1H-pyrazol-1-yl)butan-2-ol or (2S,3S)-3-(4-(2-amino-5-(trifluoromethyl)pyrimidin-4-yl)-1H-pyrazol-1-yl)butan-2-ol as a white solid. MS (ES+) $C_{12}H_{14}F_3N_5O$ requires: 301, found: 302 $[M+H]^+$.

Step 3. Synthesis of 3-fluoro-4-((4-(1-((2S,3S)-3-hydroxybutan-2-yl)-1H-pyrazol-4-yl)-5-(trifluoromethyl)pyrimidin-2-yl)amino)benzenesulfonamide or 3-fluoro-4-((4-(1-((2R,3R)-3-hydroxybutan-2-yl)-1H-pyrazol-4-yl)-5-(trifluoromethyl)pyrimidin-2-yl)amino)benzenesulfonamide or 3-fluoro-4-((4-(1-((2R,3S)-3-hydroxybutan-2-yl)-1H-pyrazol-4-yl)-5-(trifluoromethyl)pyrimidin-2-yl)amino)benzenesulfonamide or 3-fluoro-4-((4-(1-((2S,3R)-3-hydroxybutan-2-yl)-1H-pyrazol-4-yl)-5-(trifluoromethyl)pyrimidin-2-yl)amino)benzenesulfonamide (Example 9)

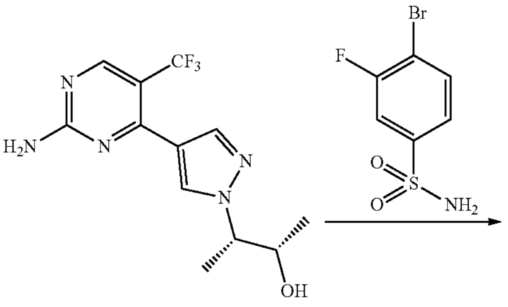

Intermediate 12-P2

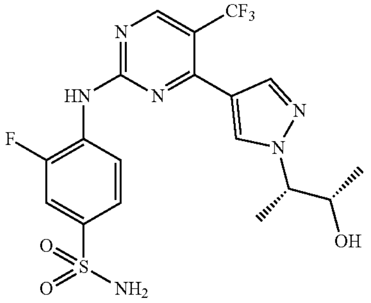

A mixture of Intermediate 12-P2 (100 mg, 331 μmol), 4-bromo-3-fluorobenzene-1-sulfonamide (84.0 mg, 331 μmol), potassium acetate (97.4 mg, 993 μmol) and BrettPhos Pd G4 (50.8 mg, 33.1 μmol) in dioxane (5 mL) was stirred at 90° C. overnight under $N_2$. The reaction mixture was concentrated and the residue was purified by flash chromatography on silica gel eluting with EA/PE (5/1) and then by Prep-HPLC (Basic conditions) to give the title product (29.6 mg, 18% yield) as a white solid. MS (ES+) $C_{18}H_{18}F_4N_6O_3S$ requires: 474, found: 475 $[M+H]^+$. $^1$H-NMR (400 MHz, DMSO-$d_6$) δ ppm 10.08 (s, 1H), 8.76 (s, 1H), 8.27 (s, 1H), 8.03 (t, J=8.4 Hz, 1H), 7.96 (s, 1H), 7.70-7.67 (m, 2H), 7.43 (s, 2H), 5.06-5.04 (m, 1H), 4.32-4.28 (m, 1H), 3.88-3.85 (m, 1H), 1.46 (d, J=6.8 Hz, 3H), 0.90 (d, J=6.0 Hz, 3H).

Example 10. 4-((5-chloro-4-(1-(2-hydroxy-2-methylpropyl)-1H-pyrazol-4-yl)pyrimidin-2-yl)amino)-3-fluorobenzenesulfonamide

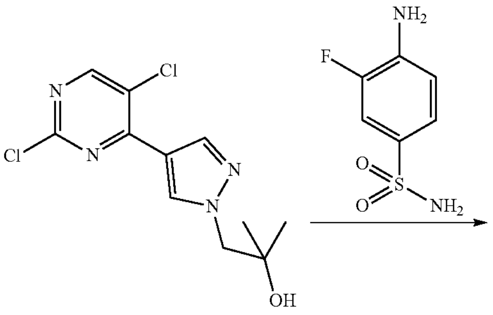

Intermediate 2

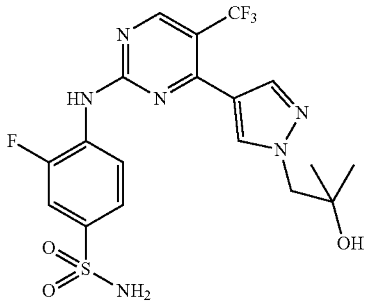

The title compound was obtained as a white solid, 23.6 mg, 8% yield, from Intermediate 2 and 4-amino-3-fluorobenzenesulfonamide, following the procedure described in Example 4, step 3. MS (ES+) $C_{17}H_{18}ClFN_6O_3S$ requires: 440, found: 441 $[M+H]^+$. $^1$H-NMR (400 MHz, DMSO-$d_6$) δ ppm 9.63 (br. s, 1H), 8.55 (s, 2H), 8.19 (s, 1H), 7.98 (t, J=8.4 Hz, 1H), 7.69-7.63 (m, 2H), 7.41 (br.s, 2H), 4.82 (s, 1H), 4.14 (s, 2H), 1.10 (s, 6H).

Example 11. 4-((5-(difluoromethyl)-4-(1-(2-hydroxy-2-methylpropyl)-1H-pyrazol-4-yl)pyrimidin-2-yl)amino)-3-fluorobenzenesulfonamide

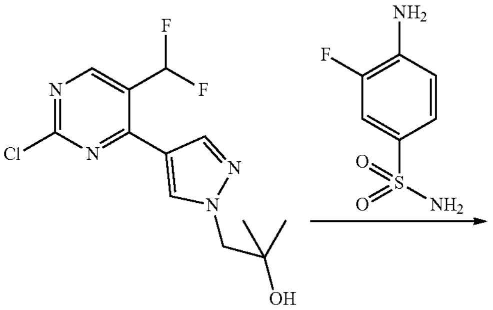

Intermediate 4

-continued

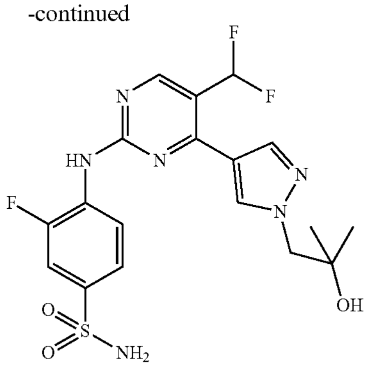

The title compound was obtained as a white solid, 156.8 mg, 19% yield, from Intermediate 4 and 4-amino-3-fluorobenzenesulfonamide following the procedure described in Example 4, step 3. MS (ES+) C18H19F3N6O3S requires: 456, found: 457 [M+H]+. 1H-NMR (400 MHz, DMSO-d6) δ ppm 9.84 (s, 1H), 8.67 (s, 1H), 8.26 (s, 1H), 8.10 (t, 1H, J=8.0 Hz), 7.98 (s, 1H), 7.68-7.65 (m, 2H), 7.42 (s, 2H), 7.22 (t, 1H, J=53.6 Hz), 4.79 (s, 1H), 4.12 (s, 2H), 1.09 (s, 6H).

Example 12. (R)-3-fluoro-4-((4-(1-(2-hydroxy-2-methylbutyl)-1H-pyrazol-4-yl)-5-(trifluoromethyl)pyrimidin-2-yl)amino)benzenesulfonamide or (S)-3-fluoro-4-((4-(1-(2-hydroxy-2-methylbutyl)-1H-pyrazol-4-yl)-5-(trifluoromethyl)pyrimidin-2-yl)amino)benzenesulfonamide Step 1. Synthesis of 2-methyl-1-(4-(4,4,5,5-tetramethyl-1,3,2-dioxaborolan-2-yl)-1H-pyrazol-1-yl)butan-2-ol (Intermediate 14)

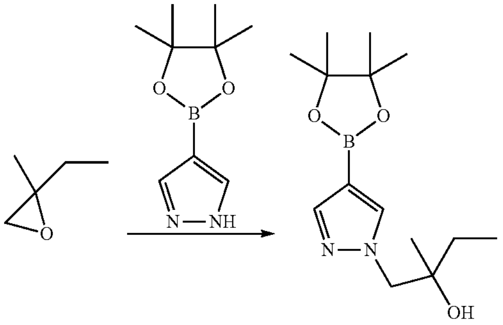

Intermediate 14

A mixture of 4-(4,4,5,5-tetramethyl-1,3,2-dioxaborolan-2-yl)-1H-pyrazole (400 mg, 2.05 mmol), 2-ethyl-2-methyloxirane (220 mg, 2.05 mmol) and $Cs_2CO_3$ (2.02 g, 6.16 mmol) in NMP (10 mL) was heated to 120° C. under microwave irradiation for 30 min, LCMS showed ~75% of product, the resulting reaction mixture was used in the next step directly. MS (ES+) $C_{14}H_{25}BN_2O_3$ requires: 280, found: 281$[M+H]^+$.

Step 2. Synthesis of 1-(4-(2-amino-5-(trifluoromethyl)pyrimidin-4-yl)-1H-pyrazol-1-yl)-2-methylbutan-2-ol (Intermediate 15)

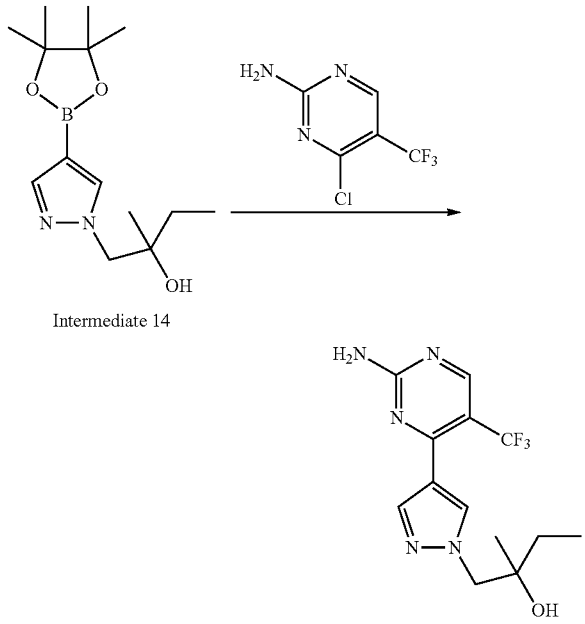

Intermediate 14

Intermediate 15

To the reaction mixture of Step 1 (Intermediate 14) was added 4-chloro-5-(trifluoromethyl)pyrimidin-2-amine (404 mg, 2.05 mmol), Pd(dppf)$Cl_2$ (38 mg, 0.05 mmol), $Cs_2CO_3$, dioxane (3 mL) and $H_2O$ (1 mL). The resulting mixture was stirred at 90° C. for 2 h under $N_2$. The reaction mixture was concentrated and the residue was purified by flash chromatography on silica gel eluting with MeOH/DCM (1/20) to give the title compound (250 mg, 39% yield) as a yellow solid. MS (ES+) $C_{13}H_{16}F_3N_5O$ requires: 315, found: 316 $[M+H]^+$.

Step 3. Synthesis of 3-fluoro-4-((4-(1-(2-hydroxy-2-methylbutyl)-1H-pyrazol-4-yl)-5-(trifluoromethyl)pyrimidin-2-yl)amino)benzenesulfonamide (Intermediate 16)

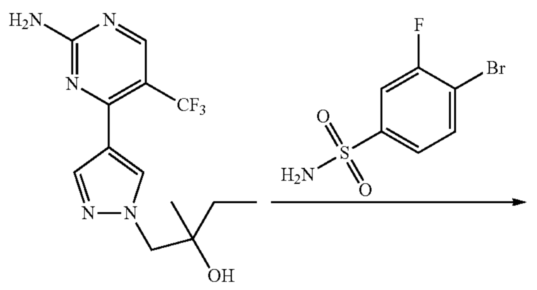

Intermediate 15

-continued

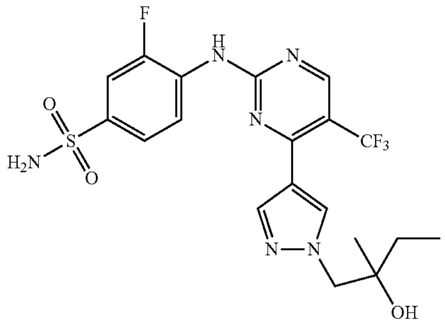

Intermediate 16

A mixture of Intermediate 15 (250 mg, 0.79 mmol), 4-bromo-3-fluorobenzene-1-sulfonamide (201 mg, 792 μmol), potassium acetate (232 mg, 2.37 mmol) and BrettPhos Pd G4 in dioxane (5 mL) was stirred at 90° C. for 2 h under $N_2$. The reaction mixture was concentrated and the residue was purified by flash chromatography on silica gel eluting with MeOH/DCM (1/10) and then by Prep-HPLC (Basic Conditions) to give the title product (180 mg).

Step 4. Synthesis of (R)-3-fluoro-4-((4-(1-(2-hydroxy-2-methylbutyl)-1H-pyrazol-4-yl)-5-(trifluoromethyl)pyrimidin-2-yl)amino)benzenesulfonamide or (S)-3-fluoro-4-((4-(1-(2-hydroxy-2-methylbutyl)-1H-pyrazol-4-yl)-5-(trifluoromethyl)pyrimidin-2-yl)amino)benzenesulfonamide (Example 12)

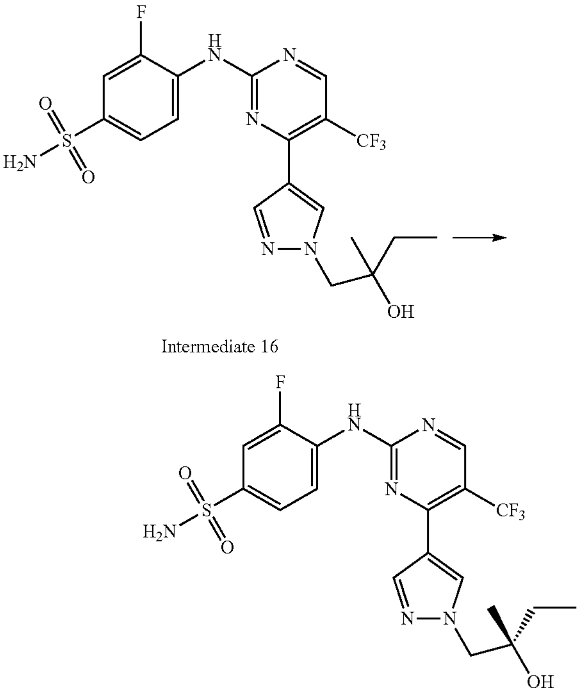

Intermediate 16

Example 12

-continued

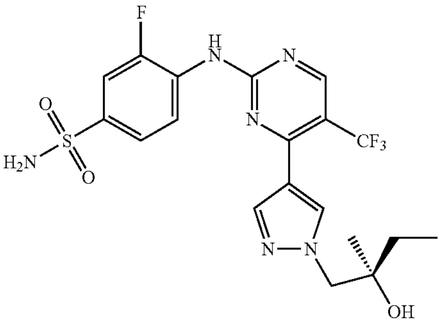

Intermediate 16 (180 mg) was separated by chiral-SFC (Column: AD-H 20*250 mm, 10 um (Daicel); Column temperature: 35° C.; Mobile phase: $CO_2$/IPA (1% Methanol Ammonia)=80/20; Flow rate: 80 g/min to afford Peak 1, Example 12 (73.2 mg, 19% yield). MS (ES+) $C_{19}H_{20}F_4N_6O_3S$ requires: 488, found: 489 $[M+H]^+$. $^1H$-NMR (400 MHz, DMSO-$d_6$) δ ppm 10.11 (s, 1H), 8.77 (s, 1H), 8.25 (s, 1H), 8.04-8.00 (m, 1H), 7.95 (s, 1H), 7.70-7.67 (m, 2H), 7.45 (s, 2H), 4.67 (s, 1H), 4.12 (s, 2H), 1.34 (q, 2H, J=7.6 Hz), 1.00 (s, 3H), 0.87 (t, 3H, J=7.6 Hz).

Example 13. 3-fluoro-4-((4-(1-((2S,3R)-3-hydroxybutan-2-yl)-1H-pyrazol-4-yl)-5-(trifluoromethyl)pyrimidin-2-yl)amino)benzenesulfonamide or 3-fluoro-4-((4-(1-((2R,3S)-3-hydroxybutan-2-yl)-1H-pyrazol-4-yl)-5-(trifluoromethyl)pyrimidin-2-yl)amino)benzenesulfonamide or 3-fluoro-4-((4-(1-((2R,3R)-3-hydroxybutan-2-yl)-1H-pyrazol-4-yl)-5-(trifluoromethyl)pyrimidin-2-yl)amino)benzenesulfonamide or 3-fluoro-4-((4-(1-((2S,3S)-3-hydroxybutan-2-yl)-1H-pyrazol-4-yl)-5-(trifluoromethyl)pyrimidin-2-yl)amino)benzenesulfonamide

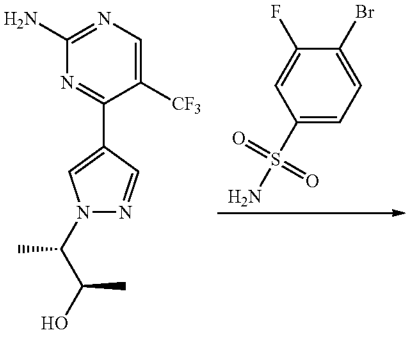

Intermediate 13-P1

-continued

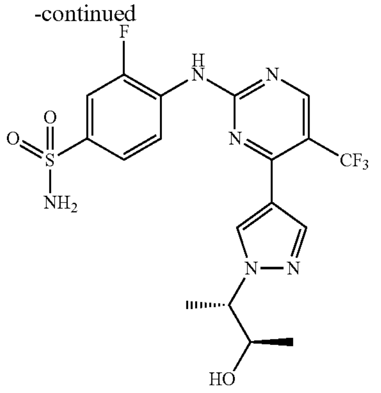

The title compound was obtained as a white solid, 72 mg, 32% yield, from Intermediate 13-P1, and 4-bromo-3-fluorobenzene-1-sulfonamide following the procedure described in Example 9, step 3. MS (ES+) $C_{18}H_{18}F_4N_6O_3S$ requires: 474, found: 475 $[M+H]^+$. $^1H$-NMR (400 MHz, DMSO-$d_6$) δ ppm 10.08 (s, 1H), 8.76 (s, 1H), 8.24 (s, 1H), 8.02 (t, J=8.4 Hz, 1H), 7.95 (s, 1H), 7.70-7.67 (m, 2H), 7.45 (s, 2H), 4.95 (s, 1H), 4.32-4.28 (m, 1H), 3.88-3.85 (m, 1H), 1.42 (d, J=7.2 Hz, 3H), 0.90 (d, J=6.4 Hz, 3H).

Example 14. 4-((5-chloro-4-(1-(2-hydroxy-2-methylpropyl)-1H-pyrazol-4-yl)pyrimidin-2-yl)amino-3-methylbenzenesulfonamide

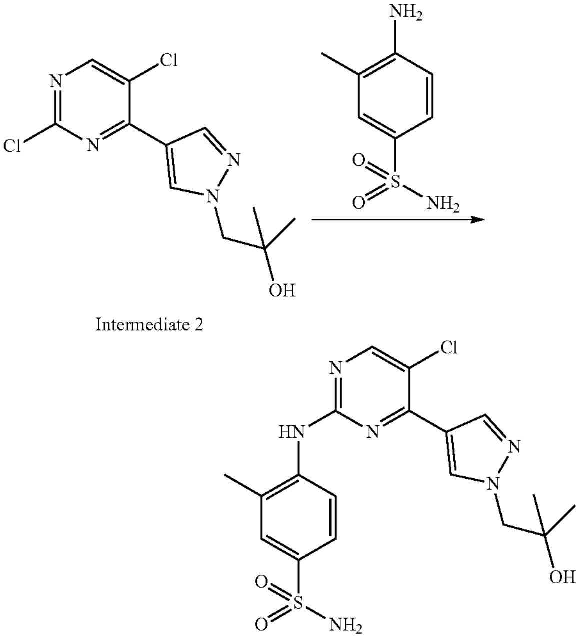

Intermediate 2

A mixture of 4-amino-3-methylbenzene-1-sulfonamide (30 mg, 161 μmol) and Intermediate 2, (50.8 mg, 177 μmol) in IPA (6 mL) and TsOH (55.4 mg, 322 μmol) was stirred at 120° C. for two days. The reaction mixture was purified by Prep-HPLC (Basic conditions) to give the title compound (2.1 mg, 2% yield) as a white solid. MS (ES+) $C_{18}H_{21}ClN_6O_3S$ requires: 436, found: 437 $[M+H]^+$. $^1H$-NMR (400 MHz, DMSO-$d_6$) δ ppm 9.11 (s, 1H), 8.51 (s, 1H), 8.47 (s, 1H), 8.13 (s, 1H), 7.84 (d, J=8.4 Hz, 1H), 7.68-7.64 (m, 2H), 7.23 (br.s, 2H), 4.80 (br.s, 1H), 4.12 (s, 2H), 2.33 (s, 3H), 1.09 (s, 6H).

Example 15: 3-fluoro-4-((4-(1-((2R,3S)-3-hydroxybutan-2-yl)-1H-pyrazol-4-yl)-5-(trifluoromethyl)pyrimidin-2-yl)amino)benzenesulfonamide or 3-fluoro-4-((4-(1-((2S,3R)-3-hydroxybutan-2-yl)-1H-pyrazol-4-yl)-5-(trifluoromethyl)pyrimidin-2-yl)amino)benzenesulfonamide or 3-fluoro-4-((4-(1-((2R,3R)-3-hydroxybutan-2-yl)-1H-pyrazol-4-yl)-5-(trifluoromethyl)pyrimidin-2-yl)amino)benzenesulfonamide or 3-fluoro-4-((4-(1-((2S,3S)-3-hydroxybutan-2-yl)-1H-pyrazol-4-yl)-5-(trifluoromethyl)pyrimidin-2-yl)amino)benzenesulfonamide

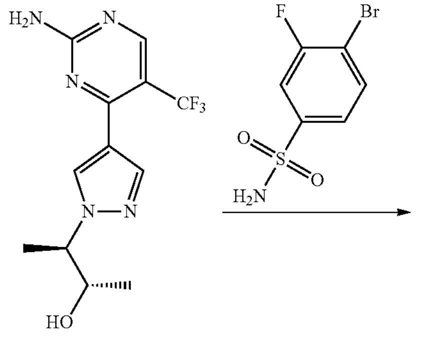

Intermediate 13-P2

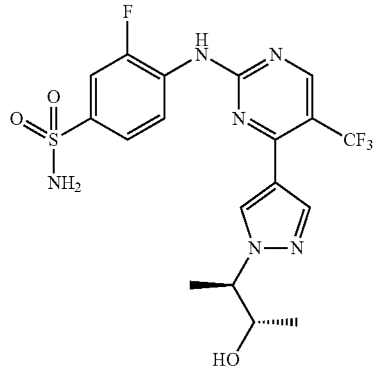

The title compound was obtained, 96.2 mg, 47% yield, as a white solid, from Intermediate 13-P2 and 4-bromo-3-fluorobenzene-1-sulfonamide following the procedure described in Example 9, step 3. MS (ES+) $C_{18}H_{18}f_4N_6O_3S$ requires: 474, found: 475 $[M+H]^+$. $^1$H-NMR (400 MHz, DMSO-$d_6$) δ ppm 10.08 (s, 1H), 8.76 (s, 1H), 8.24 (s, 1H), 8.02 (t, J=8.0 Hz, 1H), 7.95 (s, 1H), 7.70-7.67 (m, 2H), 7.45 (s, 2H), 4.93 (s, 1H), 4.33-4.29 (m, 1H), 3.88-3.85 (m, 1H), 1.42 (d, J=6.8 Hz, 3H), 1.02 (d, J=6.0 Hz, 3H).

Example 16: 3-fluoro-4-((4-(1-(1-(hydroxymethyl)cyclopropyl)-1H-pyrazol-4-yl)-5-(trifluoromethyl)pyrimidin-2-yl)amino)benzenesulfonamide

Step 1. Synthesis of methyl 1-(4-(4,4,5,5-tetramethyl-1,3,2-dioxaborolan-2-yl)-1H-pyrazol-1-yl)cyclopropane-1-carboxylate (Intermediate 17)

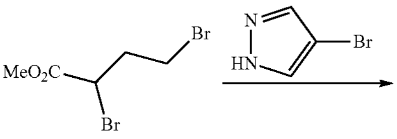

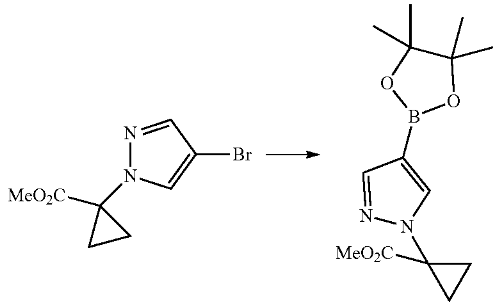

Intermediate 17

To a solution of 4-bromo-1H-pyrazole (1 g, 6.80 mmol) in anhydrous DMF at 0° C. was added NaH (326 mg, 13.6 mmol) followed by methyl 2,4-dibromobutanoate (1.94 g, 7.48 mmol). The mixture was stirred at rt overnight. LCMS indicated completion of the reaction. The reaction mixture was purified by flash chromatography on silica gel eluting with EA/PE (1/1) to afford methyl 1-(4-bromo-1H-pyrazol-1-yl)cyclopropane-1-carboxylate (700 mg, 42% yield) as a white solid.

A mixture of 4,4,5,5-tetramethyl-2-(4,4,5,5-tetramethyl-1,3,2-dioxaborolan-2-yl)-1,3,2-dioxaborolane (1.08 g, 4.27 mmol), methyl 1-(4-bromo-1H-pyrazol-1-yl)cyclopropane-1-carboxylate (700 mg, 2.85 mmol), $Pd(dppf)Cl_2$ (417 mg, 570 μmol) and KOAc (559 mg, 5.7 mmol) was stirred at 100° C. overnight under $N_2$. LCMS indicated completion of the reaction. The reaction mixture was concentrated and the residue was purified by flash chromatography on silica gel eluting with EA/PE (1/1) to afford the title compound (700 mg, 84% yield) as a white solid. MS (ES+) $C_{14}H_{21}BN_2O_4$ requires: 292, found: 293 [M+H].

Step 2. Synthesis of methyl 1-(4-(2-amino-5-(trifluoromethyl)pyrimidin-4-yl)-1H-pyrazol-1-yl)cyclopropane-1-carboxylate (Intermediate 18)

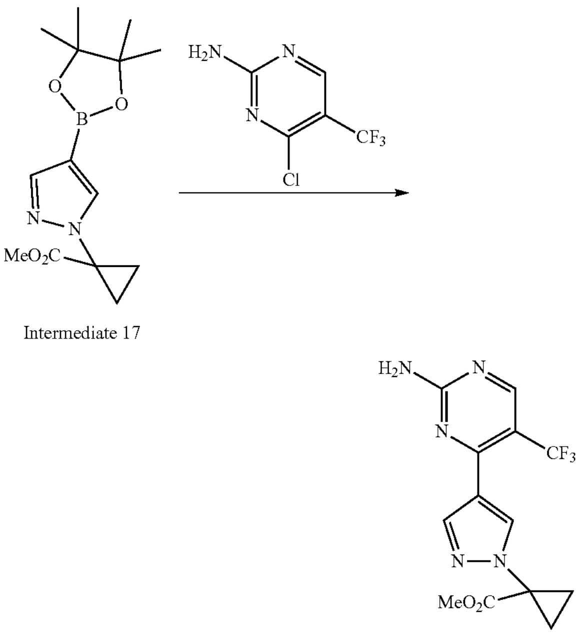

Intermediate 17

Intermediate 18

A mixture of 4-chloro-5-(trifluoromethyl)pyrimidin-2-amine (403 mg, 2.04 mmol), Intermediate 17 (400 mg, 1.36 mmol), $Na_2CO_3$ (288 mg, 2.7 mmol) and Pd(dppf)$Cl_2$ (199 mg, 272 μmol) in dioxane (20 mL) and $H_2O$ (5 mL) was stirred at 80° C. overnight under $N_2$. LCMS indicated completion of the reaction. The reaction mixture was concentrated and the residue was purified by flash chromatography on silica gel eluting with MeOH/DCM (5%) to afford the title compound (203 mg, 46% yield) as a white solid. MS (ES+) $C_{13}H_{12}F_3N_5O_2$ requires: 327, found: 328 $[M+H]^+$.

Step 3. Synthesis of methyl 1-(4-(2-((2-fluoro-4-sulfamoylphenyl)amino)-5-(trifluoromethyl)pyrimidin-4-yl)-1H-pyrazol-1-yl)cyclopropane-1-carboxylate (Intermediate 19)

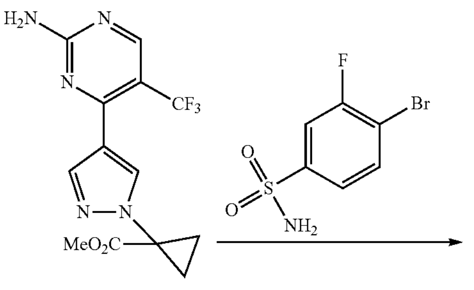

Intermediate 18

-continued

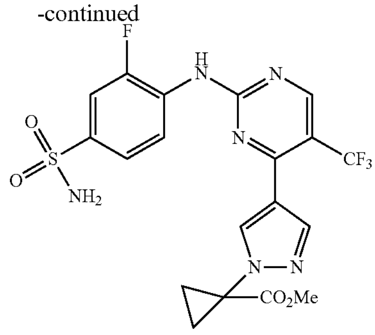

Intermediate 19

A mixture of Intermediate 18 (200 mg, 611 μmol), 4-bromo-3-fluorobenzene-1-sulfonamide (232 mg, 916 μmol), BrettPhos Pd G4 (100 mg) and KOAc (119 mg, 1.22 mmol) in dioxane (5 mL) was stirred at 100° C. overnight under $N_2$. LCMS indicated completion of the reaction. The reaction mixture was purified by flash chromatography on silica gel eluting with MeOH/DCM (5%) to afford the title compound (71 mg, 23% yield) as a white solid. MS (ES+) $C_{19}H_{16}F_4N_6O_4S$ requires: 500, found: 501 $[M+H]^+$.

Step 4. Synthesis of 3-fluoro-4-((4-(1-(1-(hydroxymethyl)cyclopropyl)-1H-pyrazol-4-yl)-5-(trifluoromethyl)pyrimidin-2-yl)amino)benzenesulfonamide (Example 16)

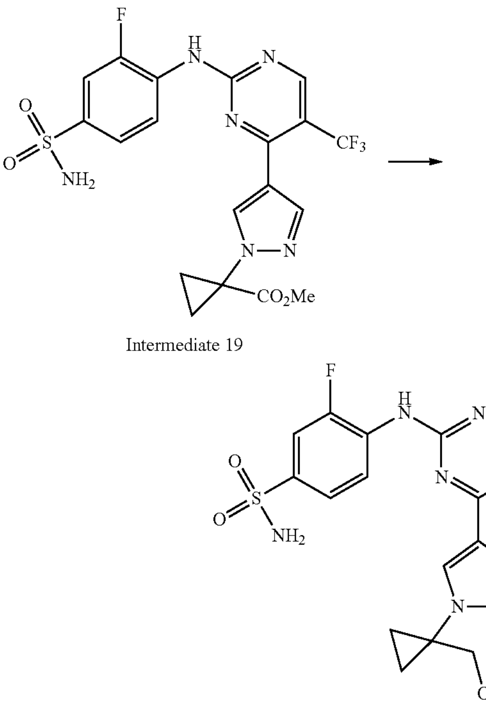

Intermediate 19

To a solution of Intermediate 19 (60 mg, 119 μmol) in THF/EtOH (v/v=1:1, 1 mL) was added $LiBH_4$ (25.9 mg, 1.19 mmol) and the mixture was stirred at 0° C. for 1 h. LCMS indicated completion of the reaction. The reaction mixture was purified by Prep-HPLC (Basic conditions) to give the title compound (5.6 mg, 10% yield) as a white solid.

MS (ES+) $C_{18}H_{16}F_4N_6O_3S$ requires; 472, found: 473 $[M+H]^+$. $^1H$-NMR (400 MHz, DMSO-$d_6$) δ ppm 10.08 (s, 1H), 8.77 (s, 1H), 8.27 (s, 1H), 8.02 (t, J=8.0 Hz, 1H), 7.94 (s, 1H), 7.70-7.65 (m, 2H), 7.44 (s, 2H), 5.10 (t, J=5.6 Hz, 1H), 3.63 (d, J=5.6 Hz, 2H), 1.24-1.05 (m, 4H).

Example 17. Synthesis of 4-((4-(1-(2-hydroxy-2-methylpropyl)-1H-pyrazol-4-yl)-5-methylpyrimidin-2-yl)amino)benzenesulfonamide Step 1. Synthesis of 1-(4-(2-chloro-5-methylpyrimidin-4-yl)-1H-pyrazol-1-yl)-2-methylpropan-2-ol (Intermediate 20)

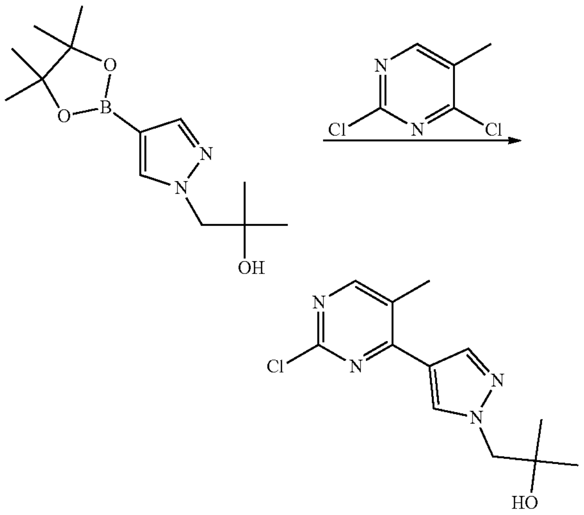

Intermediate 20

The title compound was obtained as a white solid, 170 mg, 85% yield, from 2-methyl-1-(4-(4,4,5,5-tetramethyl-1,3,2-dioxaborolan-2-yl)-1H-pyrazol-1-yl)propan-2-ol and 2,4,5-trichloropyrimidine, following the procedure described in Example 3, step 1. MS (ES+) $C_{11}H_{12}C_{12}N_4O$ requires: 266, found: 267 $[M+H]^+$.

Step 2. Synthesis of 4-((4-(1-(2-hydroxy-2-methylpropyl)-1H-pyrazol-4-yl)-5-methylpyrimidin-2-yl)amino)benzenesulfonamide (Example 17)

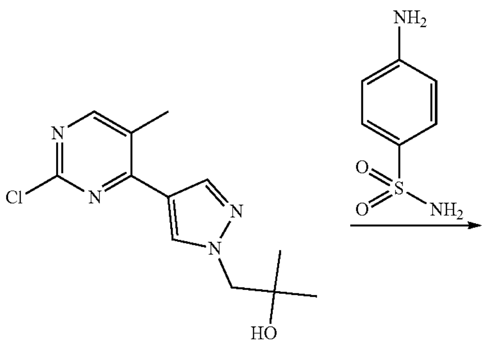

Intermediate 20

-continued

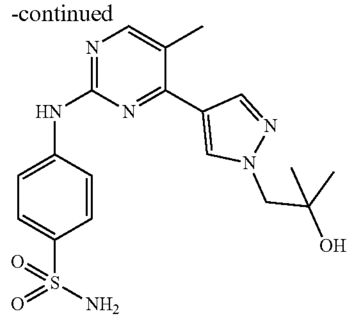

To a mixture of Intermediate 20 (160 mg, 599 μmol) and 4-aminobenzenesulfonamide (123 mg, 718 μmol) in IPA (5 mL) was added TsOH (204 mg, 1.19 mmol). The reaction mixture was stirred at 90° C. for 16 h. LCMS indicated completion of the reaction. The reaction mixture was purified by Prep-HPLC (Basic conditions) to give the title compound (76.3 mg, 31% yield) as a white solid. MS (ES+) $C_{18}H_{22}N_6O_3S$ requires: 402, found: 403 $[M+H]^+$. $^1H$-NMR (400 MHz, DMSO-$d_6$) δ ppm 9.85 (s, 1H), 8.37 (s, 1H), 8.34 (s, 1H), 8.10 (s, 1H), 7.96 (d, J=8.8 Hz, 2H), 7.54 (d, J=8.8 Hz, 2H), 7.16 (s, 2H), 4.81 (s, 1H), 4.14 (s, 2H), 2.34 (s, 3H), 11 (s, 6H).

Example 18. 4-((5-fluoro-4-(1-(2-hydroxy-2-methylpropyl)-1H-pyrazol-4-yl)pyrimidin-2-yl)amino)benzenesulfonamide Step 1. Synthesis of 1-(4-(2-chloro-5-fluoropyrimidin-4-yl)-1H-pyrazol-1-yl)-2-methylpropan-2-ol (Intermediate 21)

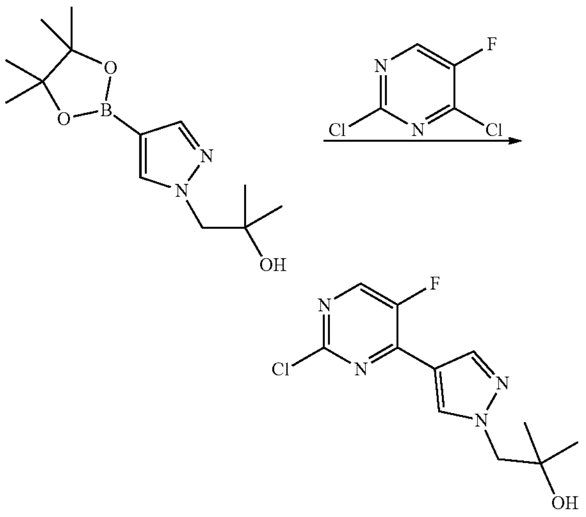

Intermediate 21

The title compound was obtained, 200 mg, 62% yield, from 2-methyl-1-(4-(4,4,5,5-tetramethyl-1,3,2-dioxaborolan-2-yl)-1H-pyrazol-1-yl)propan-2-ol and 2,4-dichloro-5-fluoropyrimidine, following a similar procedure to that described in Example 3, step 1. MS (ES+) $C_{11}H_{12}ClFN_4O$ requires: 270, found: 271 $[M+H]^+$.

Step 2. 4-((5-fluoro-4-(1-(2-hydroxy-2-methylpropyl)-1H-pyrazol-4-yl)pyrimidin-2-yl)amino)benzenesulfonamide (Example 18)

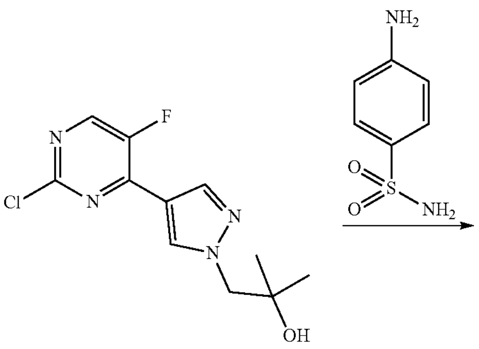

Intermediate 21

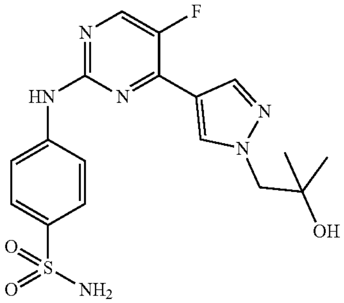

The title compound was obtained as a white solid, 15.1 mg, 10% yield, from Intermediate 21 and 4-aminobenzenesulfonamide following the procedure described in Example 4, step 3. MS (ES+) $C_{17}H_{19}FN_6O_3S$ requires: 406, found: 407 $[M+H]^+$. $^1$H-NMR (400 MHz, DMSO-$d_6$) δ ppm 10.08 (s, 1H), 8.59 (s, 1H, J=2.8 Hz), 8.39 (s, 1H), 8.13 (s, 1H), 7.94 (d, J=8.8 Hz, 2H), 7.76 (d, J=8.8 Hz, 2H), 7.18 (s, 2H), 4.82 (s, 1H), 4.16 (s, 2H), 1.10 (s, 6H).

Example 19. 4-((5-cyano-4-(1-(2-hydroxy-2-methylpropyl)-1H-pyrazol-4-yl)pyrimidin-2-yl)amino)-3-fluorobenzenesulfonamide Step 1. Synthesis of 4-(1-(2-hydroxy-2-methylpropyl)-1H-pyrazol-4-yl)-2-(methylthio)pyrimidine-5-carbonitrile (Intermediate 22)

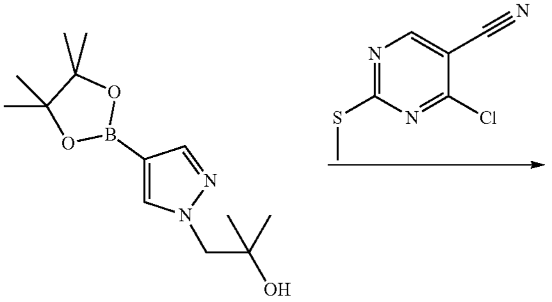

-continued

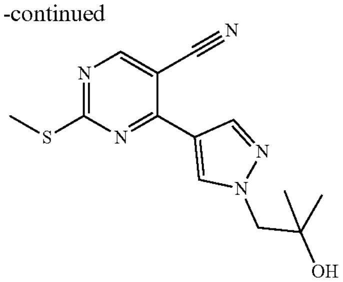

Intermediate 22

The title compound was obtained as a yellow solid, 400 mg, 85% yield, from 2-methyl-1-(4-(4,4,5,5-tetramethyl-1,3,2-dioxaborolan-2-yl)-1H-pyrazol-1-yl)propan-2-ol and 4-chloro-2-(methylthio)pyrimidine-5-carbonitrile following a similar procedure to that described in Example 3, step 1. MS (ES+) $C_{13}H_{15}N_5OS$ requires: 289, found: 290 $[M+H]^+$.

Step 2. Synthesis of 4-(1-(2-hydroxy-2-methylpropyl)-1H-pyrazol-4-yl)-2-(methylsulfonyl)pyrimidine-5-carbonitrile (Intermediate 23)

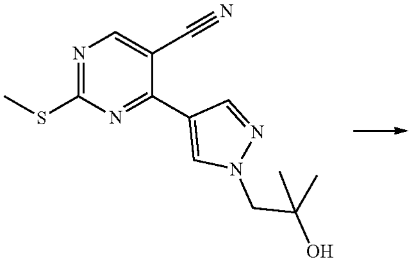

Intermediate 22

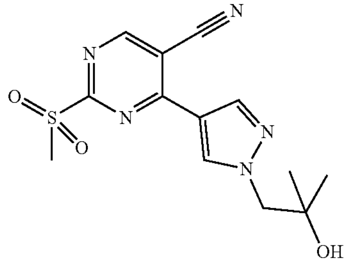

Intermediate 23

To a mixture of Intermediate 22 (400 mg, 1.38 mmol) in DCM (20 mL) was added m-CPBA (477 mg, 2.76 mmol). The reaction mixture was stirred at 25° C. for 16 h. The mixture was filtered and the filtrate was purified by flash chromatography on silica gel eluting with EA/PE (5/1) to afford the title compound (110 mg, 24% yield) as a yellow solid. MS (ES+) $C_{13}H_{15}N_5O_3S$ requires: 321, found: 322 $[M+H]^+$.

Step 3. Synthesis of 4-((5-cyano-4-(1-(2-hydroxy-2-methylpropyl)-1H-pyrazol-4-yl)pyrimidin-2-yl)amino)-3-fluorobenzenesulfonamide (Example 19)

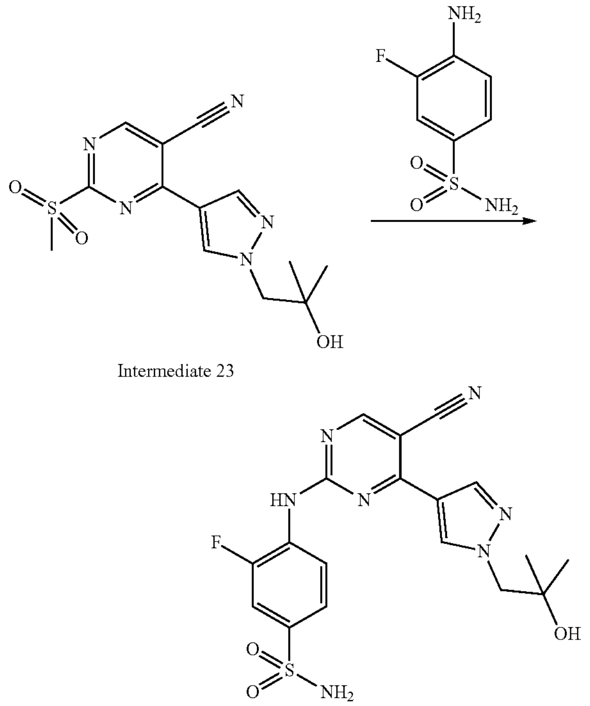

Intermediate 23

The title compound was obtained as a white solid, 23.6 mg, 22% yield, from Intermediate 23 and 4-amino-3-fluorobenzenesulfonamide, following a similar procedure to that described in Example 4, step 3. MS (ES+) $C_{18}H_{18}FN_7O_3S$ requires: 431, found: 432 $[M+H]^+$. $^1$H-NMR (400 MHz, DMSO-$d_6$) δ ppm 9.96 (s, 1H), 8.87 (s, 1H), 8.53 (s, 1H), 8.16 (s, 1H), 8.02-7.98 (m, 1H), 7.71-7.67 (m, 2H), 7.47 (s, 2H), 4.84 (s, 1H), 4.15 (s, 2H), 1.09 (s, 6H).

Example 20. (R)-3-fluoro-4-((4-(1-(2-hydroxypropyl)-1H-pyrazol-4-yl)-5-(trifluoromethyl)pyrimidin-2-yl)amino)benzenesulfonamide Step 1. Synthesis of (R)-1-(4-(4,4,5,5-tetramethyl-1,3,2-dioxaborolan-2-yl)-1H-pyrazol-1-yl)propan-2-ol (Intermediate 24)

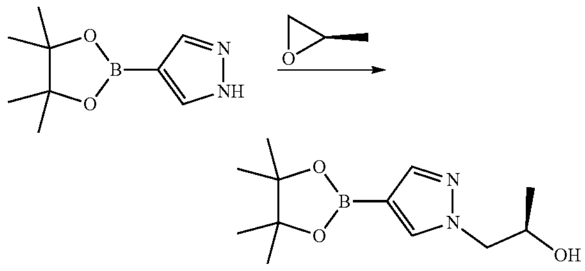

Intermediate 24

A mixture of 4-(4,4,5,5-tetramethyl-1,3,2-dioxaborolan-2-yl)-1H-pyrazole (1.0 g, 5.15 mmol), (2R)-2-methyloxirane (448 mg, 7.72 mmol) and $Cs_2CO_3$ (5.01 g, 15.4 mmol) in ACN (15 mL) was stirred at 80° C. overnight under $N_2$. LCMS indicated completion of the reaction. The reaction mixture was concentrated and the residue was purified by flash chromatography on silica gel eluting with PE/EA (1/1) to afford the tide compound (800 mg, 62% yield) as a yellow solid. MS (ES+) $C_{12}H_{21}BN_2O_3$ requires: 252, found: 253 $[M+H]^+$.

Step 2. Synthesis of (2R)-1-(4-(2-chloro-5-(trifluoromethyl)pyrimidin-4-yl)-1H-pyrazol-1-yl)propan-2-ol (Intermediate 25)

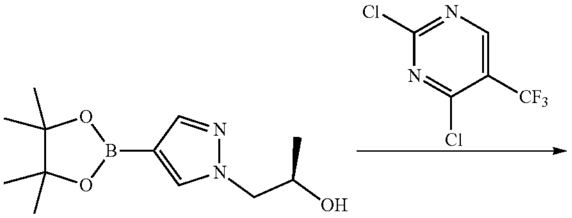

Intermediate 24

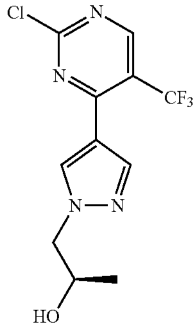

Intermediate 25

A mixture of Intermediate 24 (500 mg, 1.98 mmol) and 2,4-dichloro-5-(trifluoromethyl)pyrimidine (642 mg, 2.96 mmol) Pd(dppf)$Cl_2$ (72.6 mg, 99.0 μmol) and potassium carbonate (409 mg, 2.96 mmol) in dioxane (6 mL) and $H_2O$ (1.5 mL) was stirred at 90° C. overnight under $N_2$. LCMS indicated completion of the reaction. The reaction mixture was concentrated and the residue was purified by flash chromatography on silica gel eluting with PE/EA (1/1) to afford the title compound (300 mg, 49% yield) as a yellow solid. MS (ES+) $C_{11}H_{10}ClF_3N_4O$ requires: 306, found: 307 $[M+H]^+$.

Step 3. Synthesis of (R)-3-fluoro-4-((4-(1-(2-hydroxypropyl)-1H-pyrazol-4-yl)-5-(trifluoromethyl)pyrimidin-2-yl)amino)benzenesulfonamide (Example 20)

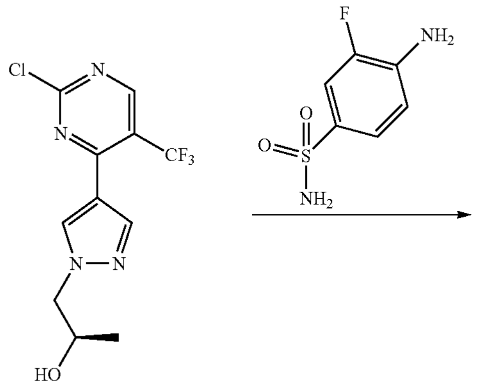

Intermediate 25

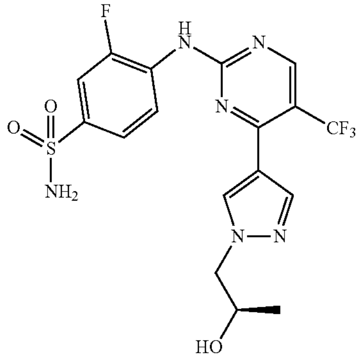

To a mixture of Intermediate 25 (150 mg, 489 μmol) and 4-amino-3-fluorobenzene-1-sulfonamide (111 mg, 586 μmol) in IPA (8 mL) was added TsOH (84.2 mg, 498 μmol) and the reaction stirred at 90° C. for 16 h. LCMS indicated completion of the reaction. The reaction mixture was purified by Prep-HPLC (Acidic conditions) to give the title compound (21.8 mg, 9% yield) as a white solid. MS (ES+) $C_{17}H_{16}F_4N_6O_3S$ requires: 460. found: 461 $[M+H]^+$. $^1H$ NMR (400 MHz, DMSO) δ 10.08 (s, 1H), 8.77 (s, 1H), 8.25 (s, 1H), 8.02 (t, J=8.0 Hz, 1H), 7.96 (s, 1H), 7.70-7.67 (m, 2H), 7.44 (s, 2H), 4.98 (s, 1H), 4.14-4.09 (m, 2H), 4.00 (s, 1H), 1.05 (d, J=6.0 Hz, 3H).

Example 21. 3-fluoro-4-((4-(1-(2-hydroxy-2-methylpropyl)-1H-pyrazol-4-yl)-5-(trifluoromethyl)pyrimidin-2-yl)amino)-2-methylbenzenesulfonamide Step 1. Synthesis of 4-bromo-3-fluoro-2-methylbenzenesulfonamide (Intermediate 26)

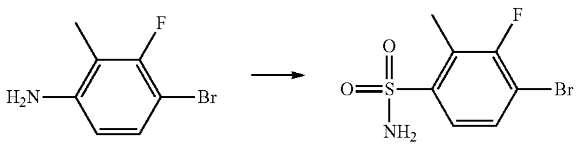

Intermediate 26

To a mixture of 4-bromo-3-fluoro-2-methylaniline (204 mg, 1.00 mmol) in ACN (12 mL) was added AcOH (0.6 mL) and conc. HCl (0.7 mL) at 0° C. Sodium nitrite (82.1 mg, 1.19 mmol) in water (0.5 mL) was added slowly. After stirring for 20 min at 0° C. $SO_2$ was pumped into the reaction mixture for 1.5 h at 0-5° C., and then $CuCl_2$ (159 mg, 1.19 mmol) was added and $SO_2$ was pumped into the resulting mixture for another 1 h. Then the reaction was stirred at 0° C. for 1 h, cold water was added and the mixture was extracted with DCM. The organic layer was washed with brine and concentrated. The residue was dissolved with DCM, and then added slowly to a cold $NH_3$/MeOH solution. After stirring for 10 min the reaction was diluted with DCM, washed with water and concentrated. Then EA/PE=1:5 was added and the resulting solid was collected by filtration to give the title product (120 mg, 45% yield) as a yellow solid. MS (ES+) $C_7H_7BrFNO_2S$ requires: 267, found: 268 $[M+H]^+$.

Step 2. Synthesis of 1-(4-(2-amino-5-(trifluoromethyl)pyrimidin-4-yl)-1H-pyrazol-1-yl)-2-methylpropan-2-ol (Intermediate 27)

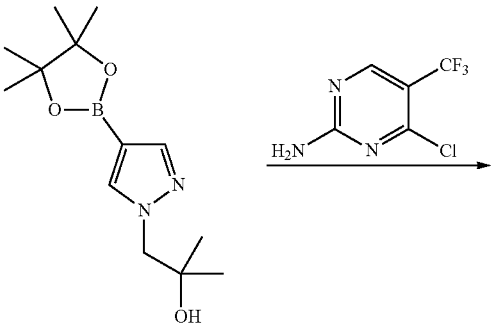

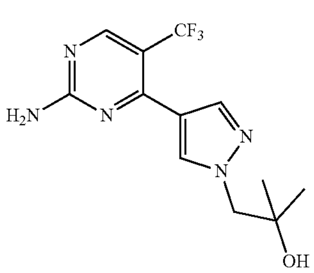

Intermediate 27

The title compound was obtained as a yellow solid, 1.7 g, 74% yield, from 4-chloro-5-(trifluoromethyl)pyrimidin-2-amine and 2-methyl-1-(4-(4,4,5,5-tetramethyl-1,3,2-dioxaborolan-2-yl)-1H-pyrazol-1-yl)propan-2-ol, following the procedure described in Example 3, step 1. MS (ES+) $C_{12}H_{14}F_3N_5O$ requires: 301, found: 302 $[M+H]^+$.

Step 2. Synthesis of 3-fluoro-4-((4-(1-(2-hydroxy-2-methylpropyl)-1H-pyrazol-4-yl)-5-(trifluoromethyl)pyrimidin-2-yl)amino)-2-methylbenzenesulfonamide (Example 21)

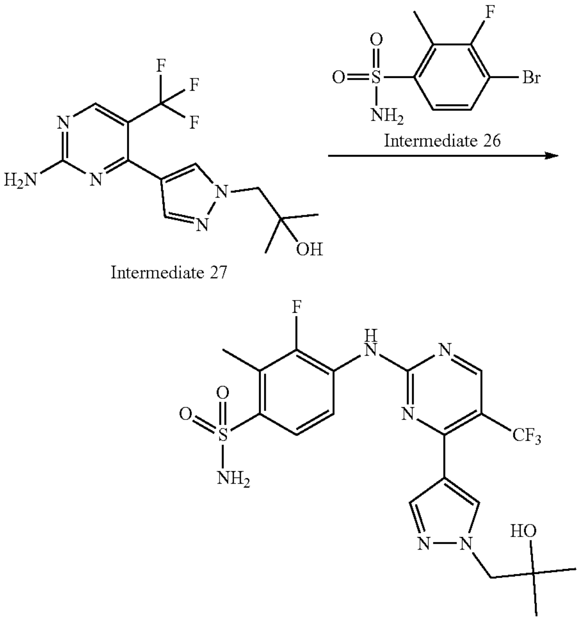

The title compound was obtained as a yellow solid, 54.8 mg, 25% yield, from 4-bromo-3-fluoro-2-methylbenzene-1-sulfonamide and 1-(4-(2-amino-5-(trifluoromethyl)pyrimidin-4-yl)-1H-pyrazol-1-yl)-2-methylpropan-2-ol, following the procedure described in Example 12, step 3. MS (ES+) $C_{19}H_{20}F_4N_6O_3S$ requires: 488, found: 489 $[M+H]^+$. $^1$H-NMR (400 MHz, DMSO-$d_6$) δ ppm 9.97 (s, 1H), 8.77 (s, 1H), 8.25 (s, 1H), 7.95 (s, 1H), 7.90-7.84 (m, 1H), 7.74-7.71 (m, 11H), 7.49 (s, 2H), 5.60 (s, 1H), 4.12 (s, 2H), 2.54 (s, 3H), 1.08 (s, 6H).

Example 22. 3-fluoro-4-((4-(1-(1-hydroxy-2-methylpropan-2-yl)-1H-pyrazol-4-yl)-5-(trifluoromethyl)pyrimidin-2-yl)amino)benzenesulfonamide

Step 1. Synthesis of 2-methyl-2-(4-(2-(methylthio)-5-(trifluoromethyl)pyrimidin-4-yl)-1H-pyrazol-1-yl)propan-1-ol (Intermediate 28)

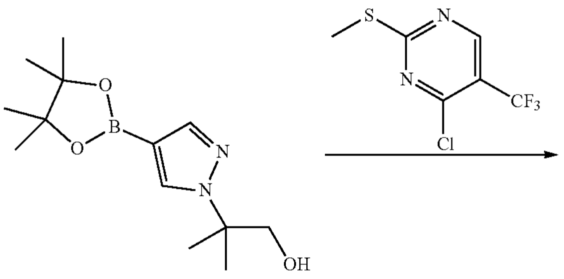

-continued

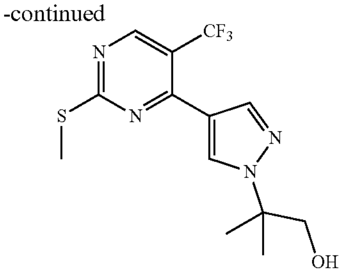

Intermediate 28

The title compound was obtained as a yellow solid, 150 mg, 48% yield, from 2-methyl-2-(4-(4,4,5,5-tetramethyl-1,3,2-dioxaborolan-2-yl)-1H-pyrazol-1-yl)propan-1-ol and 4-chloro-2-(methylthio)-5-(trifluoromethyl)pyrimidine following the procedure described in Example 3, step 1. MS (ES+) $C_{13}H_{15}F_3N_4OS$ requires: 332, found: 333 $[M+H]^+$.

Step 2. Synthesis of 2-methyl-2-(4-(2-(methylsulfonyl)-5-(trifluoromethyl)pyrimidin-4-yl)-1H-pyrazol-1-yl)propan-1-ol (Intermediate 29)

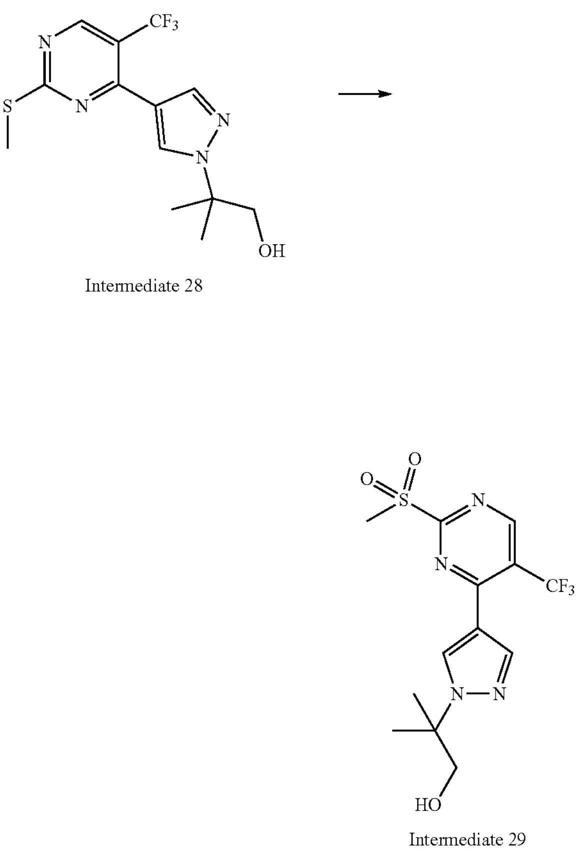

To a mixture of Intermediate 28 (150 mg, 451 μmol) in DCM (20.0 mL) was added m-CPBA (155 mg, 902 μmol). The reaction mixture was stirred at 25° C. for 16 h. The mixture was filtered and the filtrate was purified by flash chromatography on silica gel eluting with EA/PE (5/1) to afford the title compound (135 mg, 79% yield) as a yellow solid. MS (ES+) $C_{13}H_{15}F_3N_4O_3S$ requires: 364, found: 365 $[M+H]^+$.

Step 3. Synthesis of 3-fluoro-4-((4-(1-(1-hydroxy-2-methylpropan-2-yl)-1H-pyrazol-4-yl)-5-(trifluoromethyl)pyrimidin-2-yl)amino)benzenesulfonamide (Example 22)

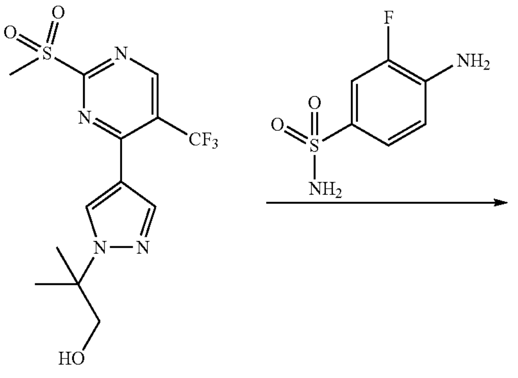

Intermediate 29

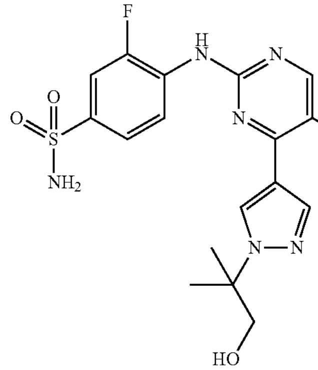

To a mixture of Intermediate 29 (90 mg, 247 μmol) and 4-amino-3-fluorobenzenesulfonamide (51 mg, 271 μmol) in IPA (10.0 mL) was added TsOH (4 mg, 24 μmol) and the reaction stirred at 90° C. for 16 h. LCMS indicated completion of the reaction. The reaction mixture was purified by Prep-HPLC (Basic conditions) to give the title compound (4.9 mg, 4% yield) as a white solid. MS (ES+) $C_{18}H_{18}F_4N_6O_3S$ requires: 474, found: 475 $[M+H]^+$. $^1$H-NMR (400 MHz, DMSO-$d_6$) δ ppm 10.08 (s, 1H), 8.76 (s, 1H), 8.27 (s, 1H), 8.02 (t, J=8.0 Hz, 1H), 7.96 (s, 1H), 7.70-7.67 (m, 2H), 7.67 (s, 1H), 7.45 (s, 2H), 5.15 (s, 1H), 3.61 (m, 2H), 1.50 (s, 6H).

Example 23. 3-chloro-4-((5-chloro-4-(1-(2-hydroxy-2-methylpropyl)-1H-pyrazol-4-yl)pyrimidin-2-yl)amino)benzenesulfonamide

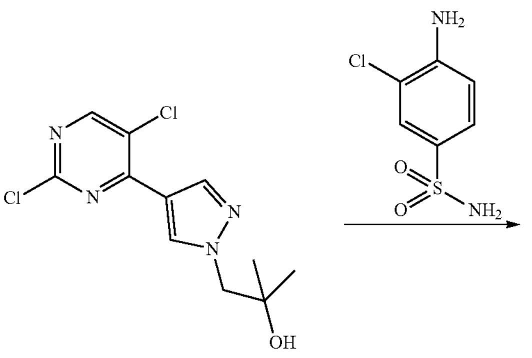

Intermediate 2

-continued

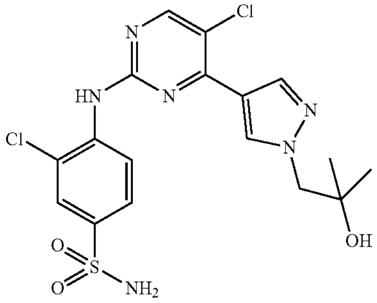

To a mixture of 4-amino-3-chlorobenzene-1-sulfonamide (70 mg, 338 μmol) and Intermediate 2 (97.0 mg, 338 μmol) in IPA (6 mL) was added TsOH (116 mg, 676 μmol), then the mixture was stirred at 120° C. overnight. The reaction mixture was purified by Prep-HPLC (Basic conditions) to give the title compound (18.4 mg, 12% yield) as a white solid. MS (ES+) $C_{17}H_{18}Cl_2NO_3S$ requires: 456, found: 457 $[M+H]^+$. $^1$H-NMR (400 MHz, DMSO-$d_6$) δ ppm 9.16 (s, 1H), 8.56 (s, 1H), 8.54 (s, 1H), 8.18 (s, 1H), 8.16 (d, J=8.8 Hz, 1H), 7.90 (d, J=2.4 Hz, 1H), 7.80 (dd, J=8.8 Hz, 2.4 Hz, 1H), 7.43 (s, 2H), 4.79 (s, 1H), 4.13 (s, 2H), 1.09 (s, 6H).

Example 24. 4-((5-ethyl-4-(1-(2-hydroxy-2-methylpropyl)-1H-pyrazol-4-yl)pyrimidin-2-yl)amino)benzenesulfonamide Step 1. Synthesis of 1-(4-(2-chloro-5-ethylpyrimidin-4-yl)-1H-pyrazol-1-yl)-2-methylpropan-2-ol (Intermediate 30)

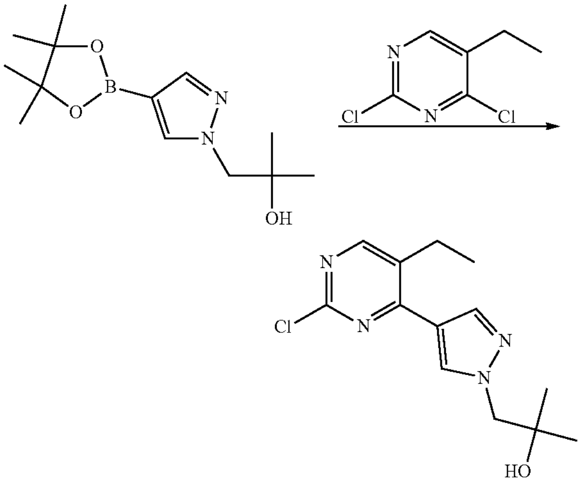

Intermediate 30

The tide compound was obtained as a white solid, 163 mg, 84% yield from 2-methyl-1-(4-(4,4,5,5-tetramethyl-1,3,2-dioxaborolan-2-yl)-1H-pyrazol-1-yl)propan-2-ol and 2,4-dichloro-5-ethylpyrimidine, following the procedure described in Example 3, step 1. MS (ES+) $C_{13}H_{17}ClN_4O$ requires: 280, found: 281 [M+H]+.

Step 2. 4-((5-ethyl-4-(1-(2-hydroxy-2-methylpropyl)-1H-pyrazol-4-yl)pyrimidin-2-yl)amino)benzenesulfonamide (Example 24

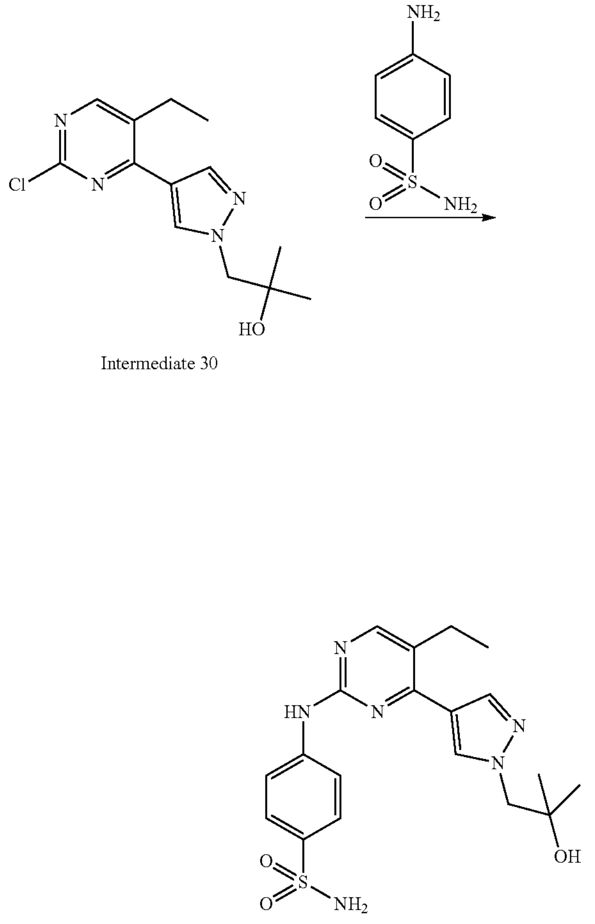

To a mixture of Intermediate 30 (140 mg, 498 μmol) and 4-aminobenzenesulfonamide (102 mg, 597 μmol) in IPA (5 mL) was added TsOH (171 mg, 996 μmol) and the reaction stirred at 90° C. for 16 h. LCMS indicated completion of the reaction. The reaction mixture was purified by Prep-HPLC (Basic conditions) to give the title compound (74.6 mg, 36% yield) as a white solid. MS (ES+) $C_{19}H_{24}N_6O_3S$ requires: 416, found: 417 $[M+H]^+$. $^1$H-NMR (400 MHz, DMSO-$d_6$) δ ppm 9.87 (s, 1H), 8.39 (s, 1H), 8.31 (s, 11H), 8.06 (s, 1H), 7.96 (d, J=8.8 Hz, 2H), 7.74 (d, J=8.8 Hz, 2H), 7.12 (s, 2H), 4.81 (s, 1H), 4.14 (s, 2H), 2.74 (d, J=7.6 Hz, 2H), 1.22 (d, J=7.6 Hz, 3H), 1.11 (s, 6H).

Example 25. 3-fluoro-4-((4-(1-((2R,3R)-3-hydroxybutan-2-yl)-1H-pyrazol-4-yl)-5-(trifluoromethyl)pyrimidin-2-yl)amino)benzenesulfonamide or 3-fluoro-4-((4-(1-((2S,3S)-3-hydroxybutan-2-yl)-1H-pyrazol-4-yl)-5-(trifluoromethyl)pyrimidin-2-yl)amino)benzenesulfonamide or 3-fluoro-4-((4-(1-((2R,3S)-3-hydroxybutan-2-yl)-1H-pyrazol-4-yl)-5-(trifluoromethyl)pyrimidin-2-yl)amino)benzenesulfonamide or 3-fluoro-4-((4-(1-((2S,3R)-3-hydroxybutan-2-yl)-1H-pyrazol-4-yl)-5-(trifluoromethyl)pyrimidin-2-yl)amino)benzenesulfonamide

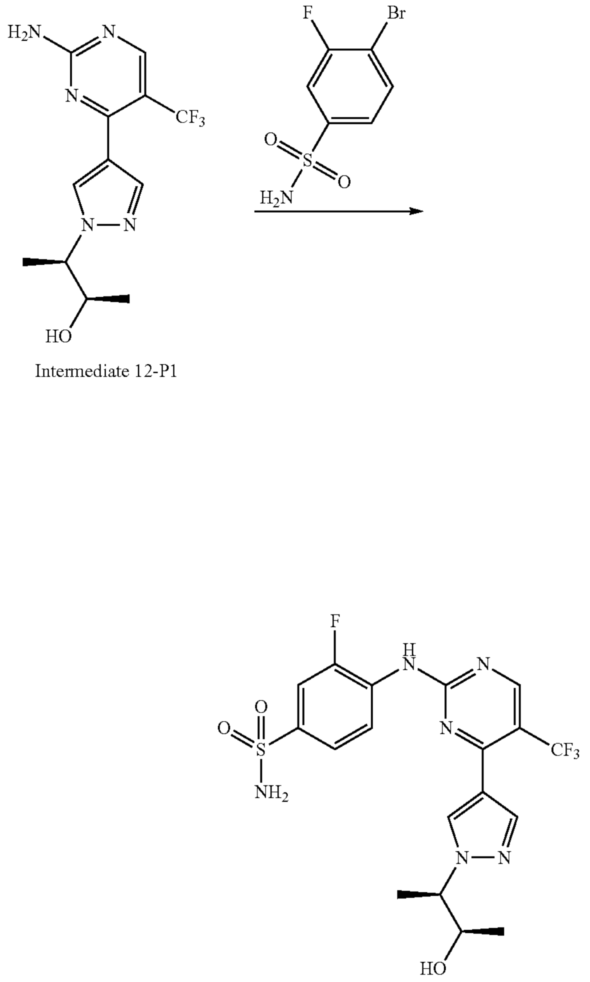

The title compound was obtained as a white solid, 43.5 mg, 25% yield, from Intermediate 12-P1 and 4-bromo-3-fluorobenzene-1-sulfonamide following the procedure described in Example 9, step 3. MS (ES+) $C_{18}H_{18}F_4N_6O_3S$ requires: 474, found: 475 $[M+H]^+$. $^1$H-NMR (400 MHz, DMSO-$d_6$) δ ppm 10.09 (s, 1H), 8.76 (s, 1H), 8.27 (s, 1H), 8.04 (t, J=8.0 Hz, 1H), 7.96 (s, 1H), 7.70-7.67 (m, 2H), 7.43 (s, 2H), 5.06-5.04 (m, 1H), 4.32-4.28 (m, 1H), 3.88-3.85 (m, 1H), 1.46 (d, J=6.8 Hz, 3H), 0.90 (d, J=6.0 Hz, 3H).

Example 26. (S)-3-fluoro-4-((4-(1-(2-hydroxy-2-methylbutyl)-1H-pyrazol-4-yl)-5-(trifluoromethyl)pyrimidin-2-yl)amino)benzenesulfonamide or (R)-3-fluoro-4-((4-(1-(2-hydroxy-2-methylbutyl)-1H-pyrazol-4-yl)-5-(trifluoromethyl)pyrimidin-2-yl)amino)benzenesulfonamide

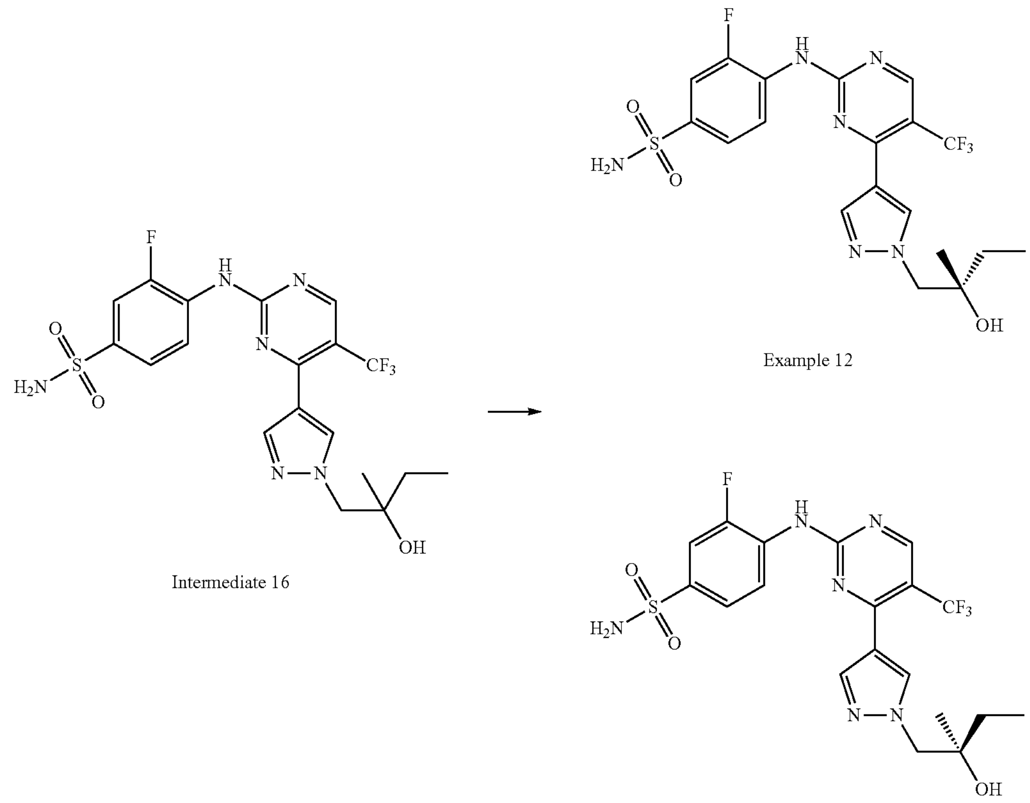

Intermediate 16

Example 12

Example 26

Intermediate 16 (180 mg) was separated by chiral-SFC (Column-AD-H 20*250 mm, 10 um (Daicel); Column temperature: 35° C.; Mobile phase: $CO_2$/IPA (1% Methanol Ammonia)=80/20; Flow rate: 80 g/min to afford Peak 1, Example 12 (73.2 mg, 19% yield) and Peak 2. Example 26 (70.8 mg, 18% yield). MS (ES+) $C_{19}H_{20}F_4N_6O_3S$ requires: 488. found: 489 $[M+H]^+$. $^1H$-NMR (400 MHz, DMSO-$d_6$) δ ppm 10.11 (s, 11H), 8.77 (s, 11H), 8.25 (s, 1H), 8.04-8.00 (m, 1H), 7.95 (s, 1H), 7.70-7.67 (m, 2H), 7.45 (s, 2H), 4.67 (s, 1H), 4.12 (s, 2H), 1.34 (q, 2H, J=7.6 Hz), 1.00 (s, 3H), 0.87 (t, 3H, J=7.6 Hz).

Example 27. 4-((4-(1-(2-hydroxy-2-methylpropyl)-1H-pyrazol-4-yl)-5-(trifluoromethyl)pyrimidin-2-yl)amino)-3-methoxybenzenesulfonamide

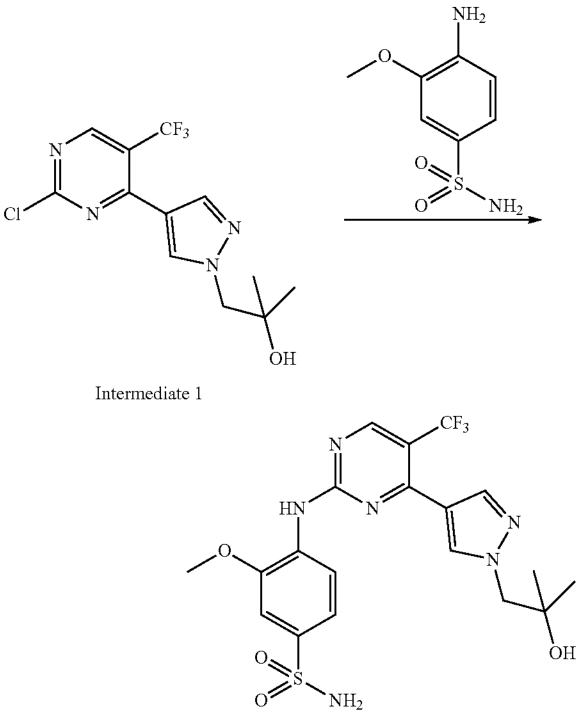

Intermediate 1

The title compound was obtained as a white solid, 52.3 mg, 34% yield, from Intermediate 1 and 4-amino-3-methoxybenzenesulfonamide following the procedure described in Example 4, step 3. MS (ES+) $C_{19}H_{21}F_3N_6O_4S$ requires: 486, found: 487 $[M+H]^+$. $^1$H-NMR (400 MHz, DMSO-$d_6$) δ ppm 9.00 (s, 1H), 8.77 (s, 1H), 8.30 (s, 1H), 8.22 (d, J=8.4 Hz, 1H), 8.00 (s, 1H), 7.51-7.47 (m, 2H), 7.30 (s, 2H), 4.80 (s, 11H), 4.14 (s, 2H), 3.93 (s, 3H), 1.10 (s, 6H).

Example 28. 4-((5-chloro-4-(1-(2-hydroxy-2-methylpropyl)-1H-pyrazol-4-yl)pyrimidin-2-yl)amino)-3-methoxybenzenesulfonamide

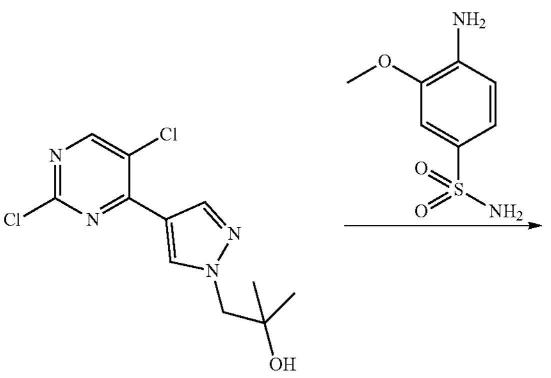

Intermediate 2

-continued

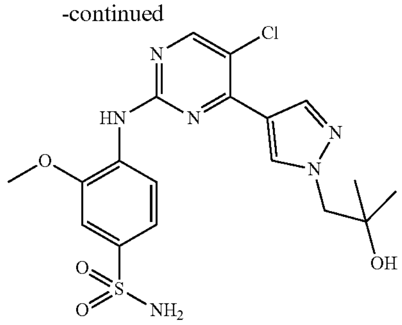

A mixture of 4-amino-3-methoxybenzene-1-sulfonamide (100 mg, 494 μmol), Intermediate 2 (184 mg, 642 μmol) and TsOH (170 mg, 988 μmol) in dioxane (6 mL) was stirred at 120° C. for 4 days. The reaction mixture was purified by Prep-HPLC (Basic conditions) to give the title compound (16.7 mg, 7% yield) as a white solid. MS (ES+) $C_{18}H_{21}ClN_6O_4S$ requires: 452, found: 453 $[M+H]^+$. $^1$H-NMR (400 MHz, DMSO-$d_6$) δ ppm 8.59 (s, 1H), 8.57 (s, 1H), 8.43 (s, 1H), 8.38 (d, J=7.6 Hz, 1H), 8.26 (s, 1H), 7.51-7.47 (m, 2H), 7.26 (s, 2H), 4.82 (s, 1H), 4.15 (s, 2H), 3.94 (s, 3H), 1.11 (s, 6H).

Example 29. Synthesis of 2,3-difluoro-4-((4-(1-(2-hydroxy-2-methylpropyl)-1H-pyrazol-4-yl)-5-(trifluoromethyl)pyrimidin-2-yl)amino)benzenesulfonamide

Step 1. Synthesis of 4-bromo-2,3-difluorobenzenesulfonamide (Intermediate 31)

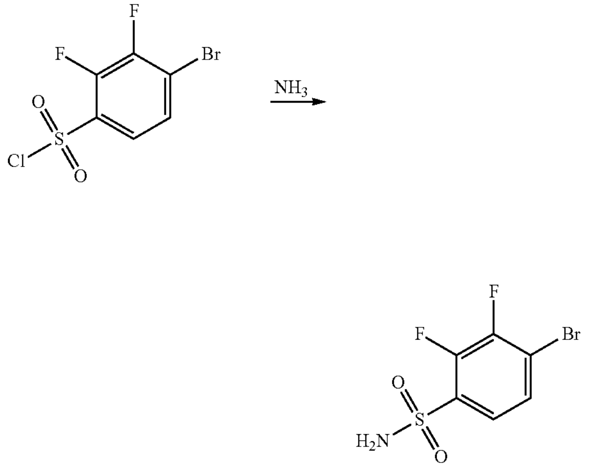

Intermediate 31

To a solution of $NH_3$ in dioxane (0.5 M, 5 mL) was added 4-bromo-2,3-difluorobenzene-1-sulfonyl chloride (300 mg, 1.02 mmol) at 0° C., and the reaction mixture was stirred at 0° C. for 1 h. The reaction mixture was diluted with EA and washed with water and brine. The organic layer was concentrated and the residue was purified by flash chromatography on silica gel eluting with EA/PE (1/2) to afford the title compound (270 mg, 97% yield) as a yellow solid.

Step 2. Synthesis of 2,3-difluoro-4-((4-(1-(2-hydroxy-2-methylpropyl)-1H-pyrazol-4-yl)-5-(trifluoromethyl)pyrimidin-2-yl)amino)benzenesulfonamide

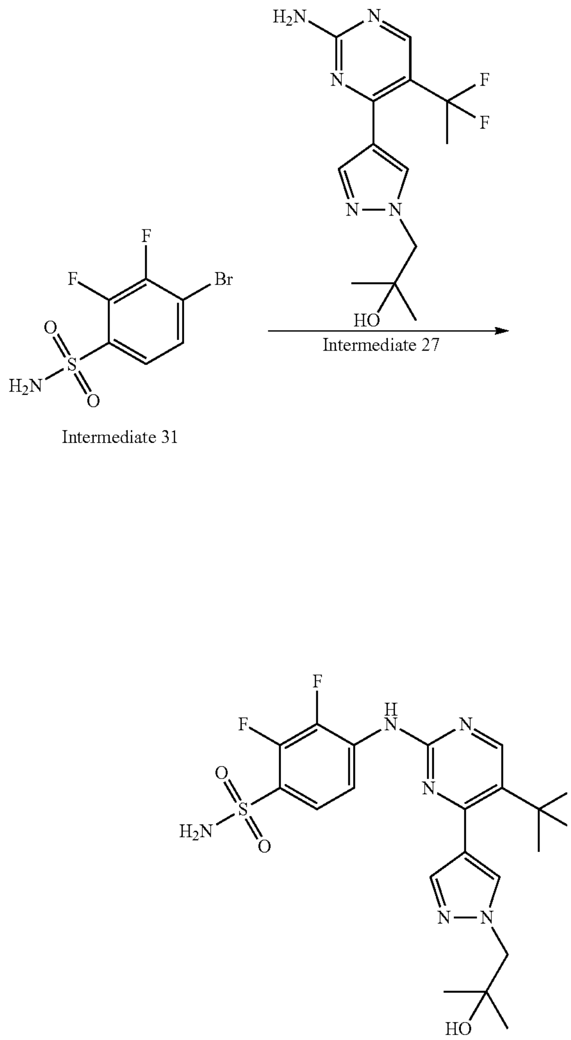

A mixture of Intermediate 31 (270 mg, 992 μmol), Intermediate 27 (298 mg, 992 μmol), BrettPhos Pd G4 (91.3 mg, 99.2 μmol) and KOAc (291 mg, 2.97 mmol) in dioxane (10 mL) was stirred at 90° C. for 14 h under $N_2$. The LCMS showed the reaction was complete. The reaction mixture was purified by Prep-HPLC (Basic conditions) to give the title compound (100 mg, 20% yield) as a white solid. MS (ES+) $C_{18}H_{17}F_5N_6O_3S$ requires: 492, found: 493 $[M+H]^+$. $^1H$-NMR (400 MHz, DMSO-$d_6$) δ ppm 8.80 (s, 1H), 8.26 (s, 1H), 7.96 (s, 1H), 7.82 (t, J=7.2 Hz, 1H), 7.62 (t, J=7.2 Hz, 1H), 4.80 (s, 1H), 4.12 (s, 2H), 1.08 (s, 6H).

Example 30. 3-fluoro-4-((5-fluoro-4-(1-(2-hydroxy-2-methylpropyl)-1H-pyrazol-4-yl)pyrimidin-2-yl)amino)benzenesulfonamide

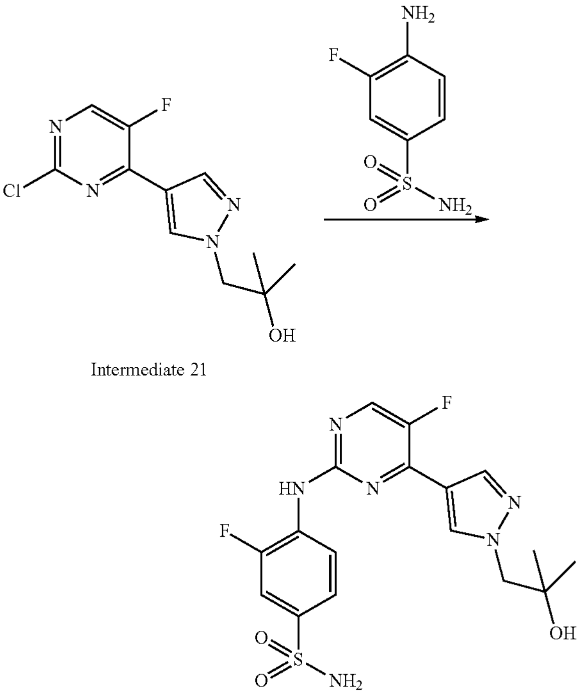

The title compound was obtained as a white solid, 6 mg, 5% yield from Intermediate 21 and 4-amino-3-fluorobenzenesulfonamide, following the procedure described in Example 4, step 3. MS (ES+) $C_{17}H_{18}F_2N_6O_3S$ requires: 424, found: 425 $[M+H]^+$. $^1H$-NMR (400 MHz, DMSO-$d_6$) δ ppm 9.46 (s, 1H), 8.56 (d, J=2.8 Hz, 1H), 8.35 (s, 1H), 8.24 (t, J=8.0 Hz, 1H), 8.07 (s, 1H), 7.69-7.60 (m, 2H), 7.38 (s, 2H), 4.80 (s, 1H), 4.15 (s, 2H), 1.10 (s, 6H).

Example 31. 4-((5-fluoro-4-(1-(2-hydroxy-2-methylpropyl)-1H-pyrazol-4-yl)pyrimidin-2-yl)amino)-3-methylbenzenesulfonamide

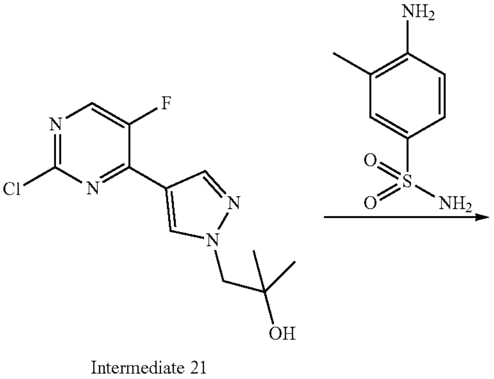

-continued

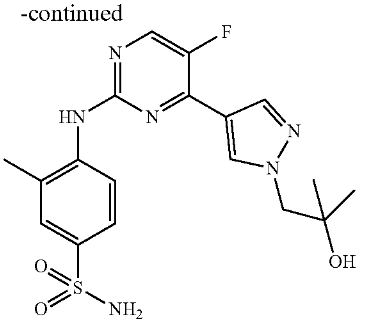

A mixture of Intermediate 21 (80 mg, 296 μmol), 4-amino-3-methylbenzenesulfonamide (55 mg, 296 μmol), KOAc (87 mg, 888 μmol), tBuXPhos (12.5 mg, 29.6 μmol) and $Pd_2(dba)_3$ (27.1 mg, 29.6 μmol) in dioxane (2 mL) was stirred at 90° C. for 16 h under $N_2$. LCMS indicated completion of the reaction. The reaction mixture was purified by Prep-HPLC (Basic conditions) to give the title compound (45.4 mg, 36% yield) as a white solid. MS (ES+) $C_{18}H_{21}FN_6O_3S$ requires: 420, found: 421 $[M+H]^+$. $^1$H-NMR (400 MHz, DMSO-$d_6$) δ ppm 8.93 (s, 1H), 8.49 (d, J=3.2 Hz, 1H), 8.31 (s, 1H), 8.02 (s, 1H), 7.90 (d, J=8.4 Hz, 1H), 7.66-7.63 (m, 2H), 7.20 (s, 2H), 4.79 (s, 1H), 4.14 (s, 2H), 2.34 (s, 2H), 1.10 (s, 6H).

Example 32. 4-((4-(1-(2-cyclopropyl-2-hydroxyethyl)-1H-pyrazol-4-yl)-5-(trifluoromethyl)pyrimidin-2-yl)amino)-3-fluorobenzenesulfonamide

Step 1. Synthesis of 1-cyclopropyl-2-(4-(4,4,5,5-tetramethyl-1,3,2-dioxaborolan-2-yl)-1H-pyrazol-1-yl)ethan-1-one (Intermediate 32)

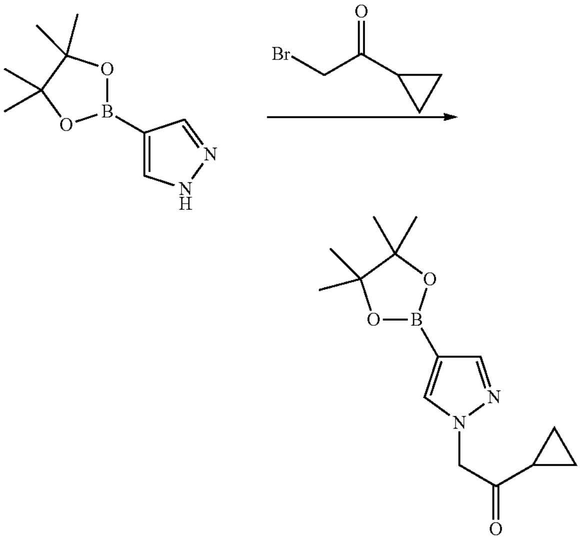

Intermediate 32

To a solution of 2-bromo-1-cyclopropylethan-1-one (402 mg, 2.47 mmol) in MeCN (6 mL) was added 4-(4,4,5,5-tetramethyl-1,3,2-dioxaborolan-2-yl)-1H-pyrazole (400 mg, 2.06 mmol) and $K_2CO_3$ (840 mg, 6.18 mmol). The mixture was stirred at 60° C. overnight. LCMS indicated completion of the reaction. The reaction mixture was concentrated and the residue was purified by flash chromatography on silica gel eluting with EA/PE (1/4) to afford the title compound (362 mg, 64% yield) as a yellow solid. MS (ES+) $C_{14}H_{21}BN_2O_3$ requires: 276, found: 277 $[M+H]^+$.

Step 2. Synthesis of 1-cyclopropyl-2-(4-(2-(methylthio)-5-(trifluoromethyl)pyrimidin-4-yl)-1H-pyrazol-1-yl)ethan-1-one (Intermediate 33)

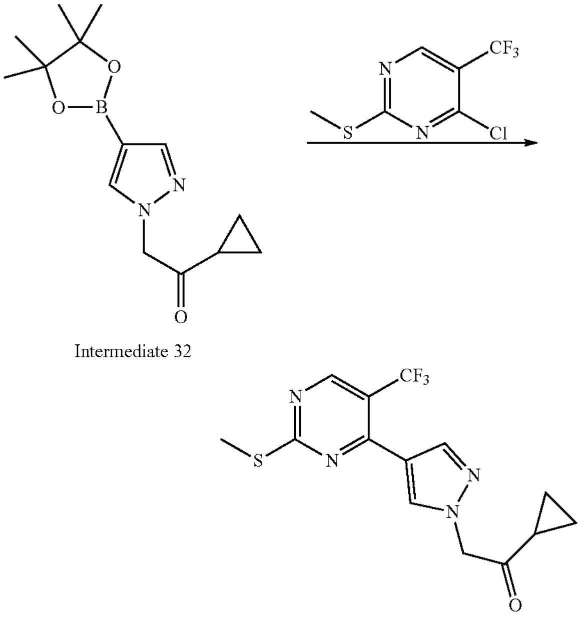

Intermediate 32

Intermediate 33

A mixture of Intermediate 32 (240 mg, 864 μmol), 2,4-dichloro-5-(trifluoromethyl)pyrimidine (187.2 mg, 864 μmol), $Na_2CO_3$ (183 mg, 1.7 mmol) and $Pd(tBu_3P)_2$ (88.2 mg, 173 μmol) in dioxane (4 mL) and $H_2O$ (1 mL) was stirred at 90° C. overnight under $N_2$. LCMS indicated completion of the reaction. The reaction mixture was concentrated and the residue was purified by flash chromatography on silica gel eluting with EA/PE (1/2) to afford the title compound (200 mg, 70% yield) as a yellow solid. MS (ES+) $C_{14}H_{13}F_3N_4OS$ requires: 342, found: 343 $[M+H]^+$.

Step 3. Synthesis of 1-cyclopropyl-2-(4-(2-(methylthio)-5-(trifluoromethyl)pyrimidin-4-yl)-1H-pyrazol-1-yl)ethan-1-ol (Intermediate 34)

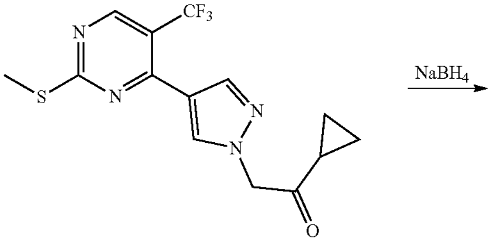

Intermediate 33

-continued

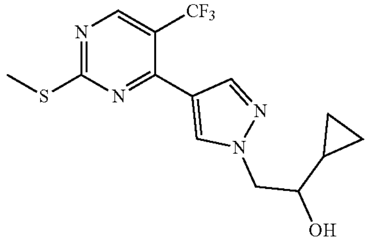

Intermediate 34

To a solution of Intermediate 33 (200 mg, 584 μmol) in MeOH (10 mL) was added $NaBH_4$ (43.8 mg, 1.16 mmol). The reaction mixture was stirred at rt overnight. LCMS indicated completion of the reaction. The reaction mixture was purified by flash chromatography on silica gel eluting with MeOH/DCM (5%) to afford the title compound (113 mg, 56% yield) as a yellow solid. MS (ES+) $C_{14}H_{15}F_3N_4OS$ requires: 344, found: 345.

Step 4. Synthesis of 1-cyclopropyl-2-(4-(2-(methylsulfonyl)-5-(trifluoromethyl)pyrimidin-4-yl)-1H-pyrazol-1-yl)ethan-1-ol (Intermediate 35)

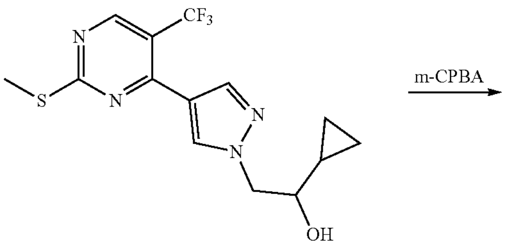

Intermediate 34

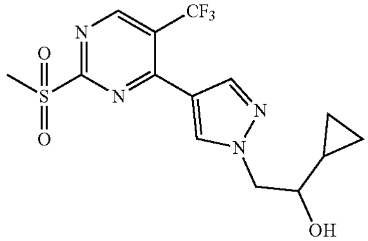

Intermediate 35

To a solution of Intermediate 34 (90 mg, 261 μmol) in DCM (2 mL) was added m-CPBA (90 mg, 522 μmol) and the reaction stirred at rt overnight. LCMS indicated completion of the reaction. The reaction mixture was purified by flash chromatography on silica gel eluting with EA/PE (1/1) to afford the title compound (73 mg, 74% yield) as a yellow solid. MS (ES+) $C_{14}H_{15}F_3N_4O_3S$ requires: 376, found: 377.

Step 5. Synthesis of 4-((4-(1-(2-cyclopropyl-2-hydroxyethyl)-1H-pyrazol-4-yl)-5-(trifluoromethyl)pyrimidin-2-yl)amino)-3-fluorobenzenesulfonamide (Example 32)

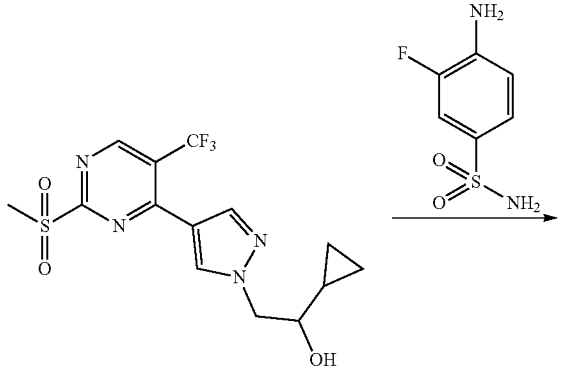

Intermediate 35

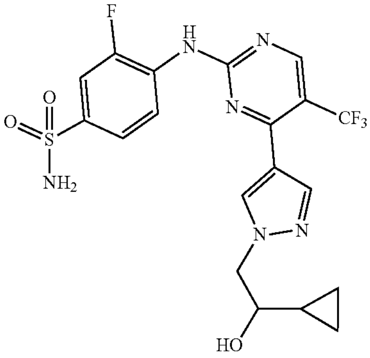

To a mixture of 4-amino-3-fluorobenzene-1-sulfonamide (20.1 mg, 106 μmol) and Intermediate 35 (40 mg, 106 μmol) in dioxane (2 mL) was added TsOH (9.12 mg, 53 μmol). The mixture was stirred at 90° C. for 16 h. LCMS indicated completion of the reaction. The reaction mixture was purified by Prep-HPLC (Basic conditions) to give the title compound (2.2 mg, 4% yield) as a yellow solid. MS (ES+) $C_{19}H_{18}F_4N_6O_3S$ requires: 486, found: 487 $[M+H]^+$. $^1H$-NMR (400 MHz, DMSO-$d_6$) δ ppm 8.75 (s, 1H), 8.25 (s, 1H), 8.00 (t, J=8 Hz, 1H), 7.85 (s, 1H), 7.68 (s, 1H), 7.66 (s, 1H), 5.02 (s, 1H), 4.29-4.17 (m, 2H), 3.30-3.20 (m, 1H), 0.85-0.76 (m, 1H), 0.41-0.31 (m, 2H), 0.31-0.26 (m, 1H), 0.12-0.06 (m, 1H), Example 33. 3-fluoro-4-((4-(1-(2-hydroxyethyl)-1H-pyrazol-4-yl)-5-(trifluoromethyl)pyrimidin-2-yl)amino)benzenesulfonamide or 3-fluoro-4-((2-(1-(2-hydroxyethyl)-1H-pyrazol-4-yl)-5-(trifluoromethyl)pyrimidin-4-yl)amino)benzenesulfonamide Step 1. Synthesis of 2-(4-(4-chloro-5-(trifluoromethyl)pyrimidin-2-yl)-1H-pyrazol-1-yl)ethan-1-ol (Intermediate 36) or 2-(4-(2-chloro-5-(trifluoromethyl)pyrimidin-4-yl)-1H-pyrazol-1-yl)ethan-1-ol

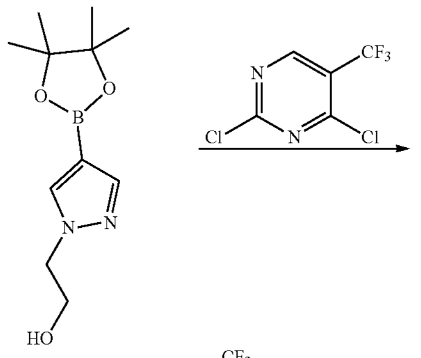

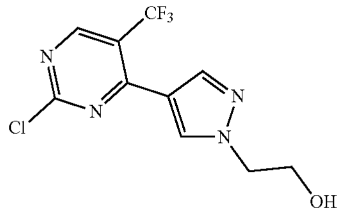

+

Intermediate 36

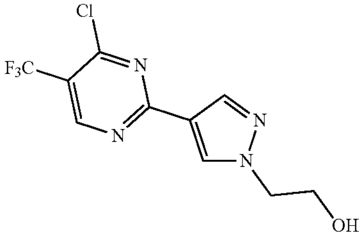

A mixture of 2-(4-(4,4,5,5-tetramethyl-1,3,2-dioxaborolan-2-yl)-1H-pyrazol-1-yl)ethan-1-ol (328 mg, 1.38 mmol), 2,4-dichloro-5-(trifluoromethyl)pyrimidine (300 mg, 1.38 mmol), $Na_2CO_3$ (380 mg, 3.58 mmol) and $Pd(dppf)Cl_2$ 32 mg, 35 μmol) in dioxane (6 mL) and $H_2O$ (2 mL) was stirred at 90° C. overnight under $N_2$. LCMS indicated completion of the reaction. The reaction mixture was concentrated and the residue was purified by flash chromatography on silica gel eluting with PE/EA (1/1) to afford peak 1 (15 mg), Intermediate 36, 2-(4-(2-chloro-5-(trifluoromethyl)pyrimidin-2-yl)-1H-pyrazol-1-yl)ethan-1-ol or 2-(4-(4-chloro-5-(trifluoromethyl)pyrimidin-4-yl)-1H-pyrazol-1-yl)ethan-1-ol and peak 2 (35 mg), 2-(4-(4-chloro-5-(trifluoromethyl)pyrimidin-2-yl)-1H-pyrazol-1-yl)ethan-1-ol or 2-(4-(2-chloro-5-(trifluoromethyl)pyrimidin-4-yl)-1H-pyrazol-1-yl)ethan-1-ol as a yellow solid. MS (ES+) $C_{10}H_8ClF_3N_4O$ requires: 292, found: 293 [M+H]+.

Step 2. Synthesis of 3-fluoro-4-((2-(1-(2-hydroxyethyl)-1H-pyrazol-4-yl)-5-(trifluoromethyl)pyrimidin-4-yl)amino)benzenesulfonamide (Example 33)

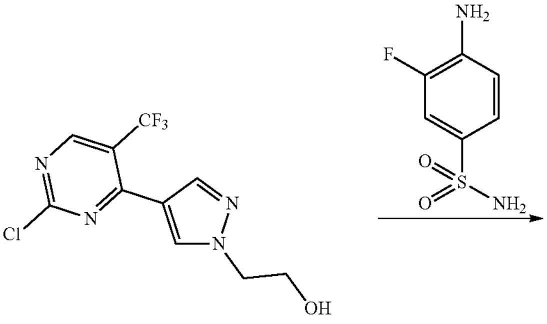

Intermediate 36

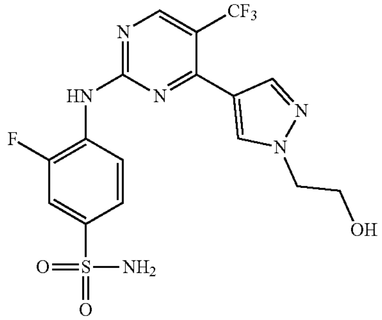

A solution of Intermediate 36 (35 mg, 120 μmol), 4-amino-3-fluorobenzene-1-sulfonamide (22.7 mg, 120 μmol) and TsOH (22.7 mg, 120 μmol) in IPA (2 mL) was stirred at 90° C. for 15 h. LCMS indicated completion of the reaction. The reaction mixture was purified by Prep-HPLC (Basic conditions) to give the title compound (24.7 mg, 46% yield) as a white solid. MS (ES+) $C_{16}H_{14}F_4N_6O_3S$ requires: 446, found: 447 [M+H]+. $^1H$ NMR (400 MHz, DMSO) δ 9.13 (s, 1H), 8.66 (s, 1H), 8.15 (s, 1H), 7.77-7.70 (m, 4H), 7.51 (s, 2H), 4.92-4.90 (m, 1H), 4.19-4.06 (m, 2H), 3.74-3.72 (m, 2H).

Example 34. 4-((5-cyano-4-(1-(2-hydroxyethyl)-1H-pyrazol-4-yl)pyrimidin-2-yl)amino)benzenesulfonamide

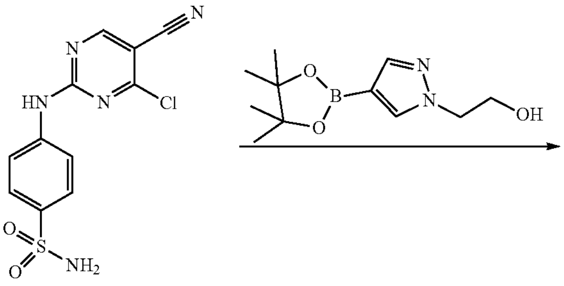

Intermediate 9

-continued

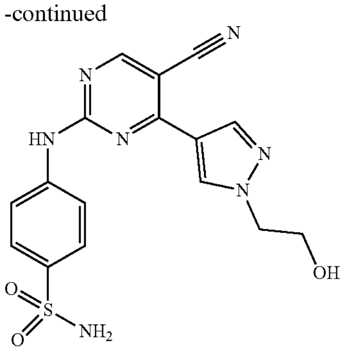

To a mixture of Intermediate 9 (70 mg, 226 μmol) and 2-(4-(4,4,5,5-tetramethyl-1,3,2-dioxaborolan-2-yl)-1H-pyrazol-1-yl)ethan-1-ol (64.5 mg, 271 μmol) in dioxane (5 mL) and water (0.5 mL) was added $Pd(t-Bu_3P)_2$ (46.1 mg, 90.4 μmol) and $Na_2CO_3$ (71.8 mg, 678 μmol) and the reaction stirred at 100° C. for 2 h. LCMS indicated completion of the reaction. The reaction mixture was purified by Prep-HPLC (Basic conditions) to give the title compound (9.7 mg, 11% yield) as a white solid. MS (ES+) $C_{16}H_{15}N_7O_3S$ requires: 385, found: 386 $[M+H]^+$. $^1H$-NMR (400 MHz, DMSO-$d_6$) δ ppm 10.67 (s, 1H), 8.91 (s, 1H), 8.59 (s, 1H), 8.30 (s, 1H), 7.96 (d, J=9.0 Hz, 2H), 7.82 (d, J=9.0 Hz, 2H), 7.25 (s, 2H), 5.00 (t, J=5.2 Hz, 1H), 4.31 (t, J=5.2 Hz, 2H), 3.78 (q, J=5.2 Hz, 2H).

Example 35. (S)-3-fluoro-4-((4-(1-(2-hydroxypropyl)-1H-pyrazol-4-yl)-5-(trifluoromethyl)pyrimidin-2-yl)amino)benzenesulfonamide Step 1. Synthesis of(S)-1-(4-(4,4,5,5-tetramethyl-1,3,2-dioxaborolan-2-yl)-1H-pyrazol-1-yl)propan-2-ol (Intermediate 37)

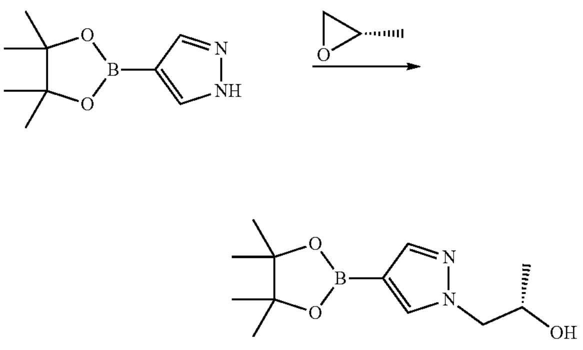

Intermediate 37

A mixture of 4-(4,4,5,5-tetramethyl-1,3,2-dioxaborolan-2-yl)-1H-pyrazole (1.0 g, 5.15 mmol), (S)-2-methyloxirane (1.49 g, 25.77 mmol) and $Cs_2CO_3$ (5.02 g, 15.45 mmol) in ACN (25 mL) was stirred at 80° C. for 48 h under $N_2$. LCMS indicated completion of the reaction. The reaction mixture was concentrated and the residue was purified by flash chromatography on silica gel eluting with DCM/MeOH (20/1) to afford the title compound (700 mg, 54% yield) as a colorless oil. MS (ES+) $C_{12}H_{21}BN_2O_3$ requires: 252, found: 253 $[M+H]^+$.

Step 2. Synthesis of(S)-1-(4-(2-chloro-5-(trifluoromethyl)pyrimidin-4-yl)-1H-pyrazol-1-yl)propan-2-ol (Intermediate 38)

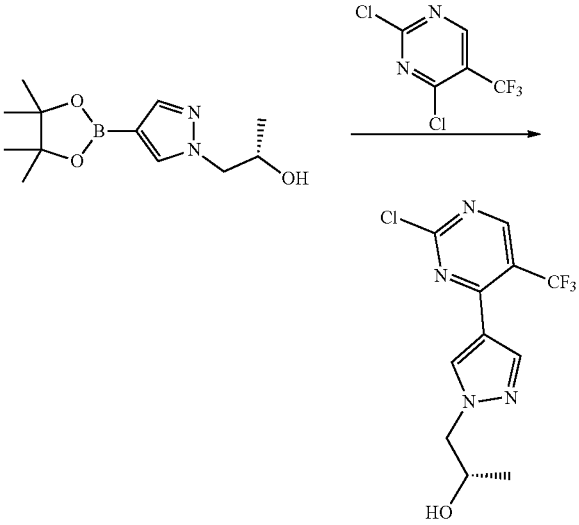

Intermediate 38

A mixture of Intermediate 37 (250 mg, 0.99 mmol), 2,4-dichloro-5-(trifluoromethyl)pyrimidine (214 mg, 0.99 mmol), $NaHCO_3$ (249 mg, 2.97 mmol) and $Pd(dppf)Cl_2$ (145 mg, 0.19 mmol) in THF (10 mL) and $H_2O$ (3 mL) was stirred at 60° C. for 2 h under $N_2$. LCMS indicated completion of the reaction. The reaction mixture was concentrated and the residue was purified by flash chromatography on silica gel eluting with EA/PE (1/1) to afford the title compound (140 mg, 46% yield) as a yellow solid. MS (ES+) $C_{11}H_{10}ClF_3N_4O$ requires: 306, found: 307 $[M+H]^+$.

Step 3. Synthesis of(S)-3-fluoro-4-((4-(1-(2-hydroxypropyl)-1H-pyrazol-4-yl)-5-(trifluoromethyl)pyrimidin-2-yl)amino)benzenesulfonamide (Example 35)

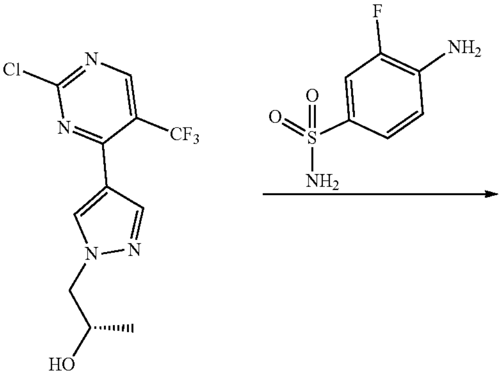

Intermediate 38

-continued

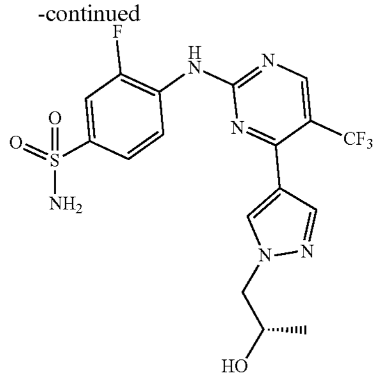

The title compound was obtained as a white solid, 39.2 mg 18% yield from Intermediate 38 and 4-amino-3-fluorobenzenesulfonamide following the procedure described in Example 4, step 3. MS (ES+) $C_{17}H_{16}F_4N_6O_3S$ requires: 460, found: 461 $[M+H]^+$. $^1$H-NMR (400 MHz, DMSO-$d_6$) δ ppm 10.08 (s, 1H), 8.77 (s, 1H), 8.24 (s, 1H), 8.02 (t, J=8.0 Hz, 1H), 7.96 (s, 1H), 7.69 (s, 1H), 7.67 (s, 1H), 7.44 (s, 2H), 4.97 (d, J=4.8 Hz, 1H), 4.17-4.06 (m, 2H), 4.02-3.96 (m, 1H), 1.06 (d, J=6.4 Hz, 3H).

Example 36. 3-fluoro-4-((4-(1-(2-hydroxy-2-methylpropyl)-1H-pyrazol-4-yl)-5-methylpyrimidin-2-yl)amino)benzenesulfonamide

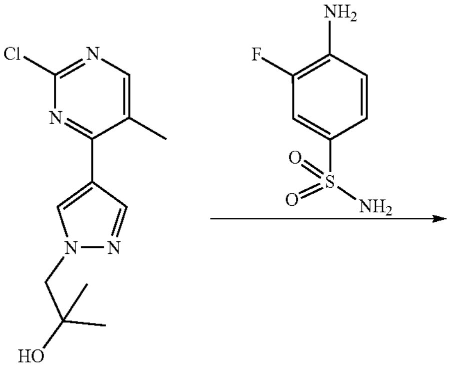

Intermediate 20

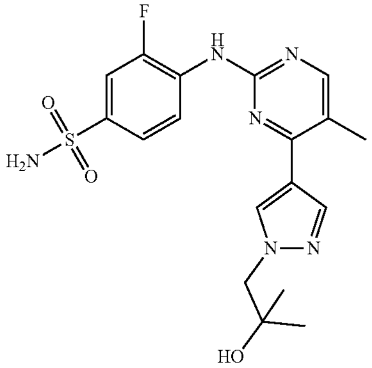

The title compound was obtained as a white solid, 83.8 mg, 35% yield from Intermediate 20 and 4-amino-3-fluorobenzene-1-sulfonamide following the procedure described in Example 4, step 3. MS (ES+) $C_{18}H_{21}FN_6O_3S$ requires: 420, found: 421 $[M+H]^+$. $^1$H NMR (400 MHz, DMSO) δ 9.13 (s, 1H), 8.35-8.32 (m, 3H), 8.06 (s, 1H), 7.66-7.60 (m, 2H), 7.35 (s, 2H), 4.78 (s, 1H), 4.12 (s, 2H), 2.34 (s, 3H), 1.10 (s, 6H).

Example 37. 4-((4-(1-(2-hydroxy-2-methylpropyl)-1H-pyrazol-4-yl)-5-(trifluoromethyl)pyrimidin-2-yl)amino)-2,6-dimethylbenzenesulfonamide

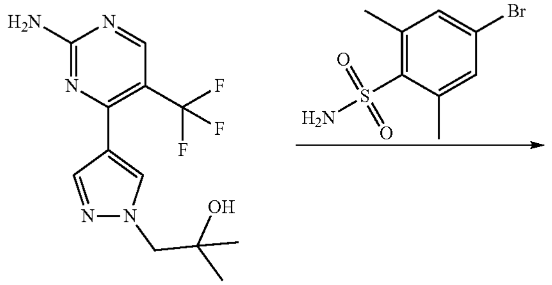

Intermediate 27

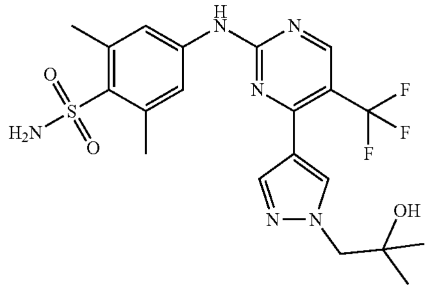

A mixture of 4-bromo-2,6-dimethylbenzenesulfonamide (130 mg, 0.492 mmol), Intermediate 27 (148 mg, 0.492 mmol), BrettPhos Pd G4 (78 mg, 0.05 mmol) and potassium acetate (74 mg, 0.76 mmol) in dioxane (5 mL) was stirred at 100° C. for overnight under $N_2$. LCMS showed the reaction was full conversion, the reaction mixture was purified with Prep-HPLC (Basic conditions) to give the title product (58.2 mg, 36% yield) as a white solid. MS (ES+) $C_{20}H_{23}F_3N_6O_3S$ requires: 484, found: 485 $[M+H]^+$. $^1$H-NMR (400 MHz, DMSO-$d_6$) δ ppm 10.27 (s, 1H), 8.80 (s, 1H), 8.26 (s, 1H), 8.04-7.99 (m, 1H), 7.96 (s, 1H), 7.85 (d, J=8.8 Hz, 1H), 7.72 (s, 2H), 4.78 (s, 1H), 4.12 (s, 2H), 1.08 (s, 6H).

Example 38. 2-chloro-3-fluoro-4-((4-(1-(2-hydroxy-2-methylpropyl)-1H-pyrazol-4-yl)-5-(trifluoromethyl)pyrimidin-2-yl)amino)benzenesulfonamide Step 1. Synthesis of 4-bromo-2-chloro-3-fluorobenzenesulfonyl chloride (Intermediate 39)

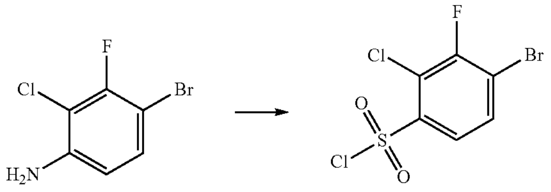

Intermediate 39

To a mixture of 4-bromo-2-chloro-3-fluoroaniline (400 mg, 1.78 mmol) in ACN (12 mL) was added AcOH (0.6 mL) and con. HCl (0.7 mL) at 0° C. Sodium nitrite (142 mg, 2.14 mmol) in water (0.5 mL) was added slowly. After stirring for 20 min at 0° C. $SO_2$ was pumped into the reaction mixture for 1.5 h at 0-5° C., and then $CuCl_2$ (287 mg, 2.14 mmol) was added and $SO_2$ was pumped into the resulting mixture for a further 1 h. The reaction was stirred at 0° C. for 1 h, cold water was added and the mixture extracted with DCM. The organic layer was washed with brine and concentrated to give the crude product (200 mg) as a yellow oil which was used in the next step without any further purification.

Step 2. Synthesis of 4-bromo-2-chloro-3-fluorobenzenesulfonamide (Intermediate 40)

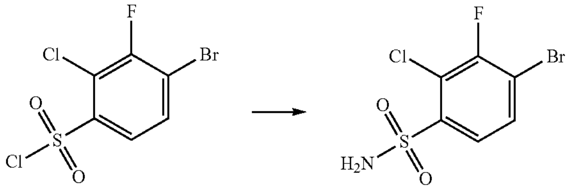

Intermediate 39 Intermediate 40

The crude of Step 1 (Intermediate 39, 200 mg, 0.66 mmol) in DCM (3 mL) was added to cold $NH_3$/MeOH (10 mL) and the reaction stirred for 10 min. The reaction was diluted with DCM, washed with water, and the organic layer was concentrated, EA was added and the resulting solid was collected by filtration to give the title product (120 mg, 64% yield) as a white solid. MS (ES+) $C_6H_4BrClFNO_2S$ requires: 287, found: 288 $[M+H]^+$.

Step 3. Synthesis of 2-chloro-3-fluoro-4-((4-(1-(2-hydroxy-2-methylpropyl)-1H-pyrazol-4-yl)-5-(trifluoromethyl)pyrimidin-2-yl)amino)benzenesulfonamide (Example 38)

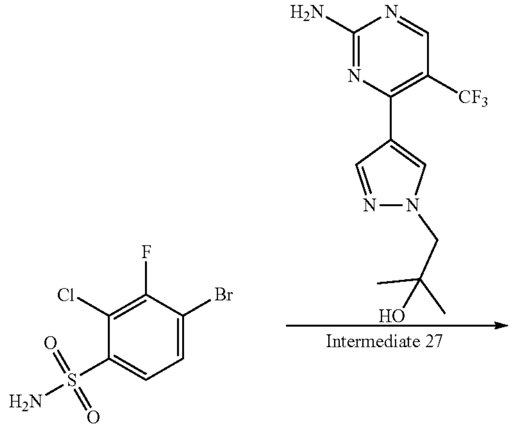

Intermediate 40

-continued

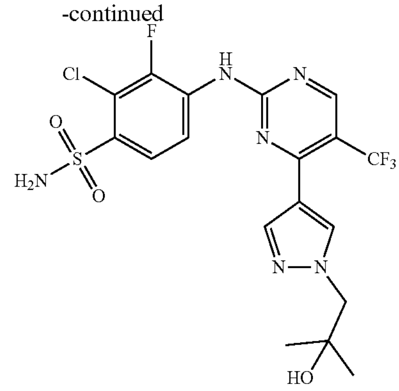

The title compound was obtained as a yellow solid, 60 mg, 28% yield, from Intermediate 27 and Intermediate 40 following the procedure described in Example 9, step 3. MS (ES+) $C_{18}H_{17}ClF_4N_6O_3S$ requires: 508, found: 509 $[M+H]^+$. $^1$H-NMR (400 MHz, DMSO-$d_6$) δ ppm 10.33 (s, 1H), 8.81 (s, 1H), 8.30 (s, 1H), 8.00 (s, 11H), 7.64 (s, 2H), 7.17 (s, 2H), 4.80 (br. s, 1H), 4.13 (s, 2H), 2.59 (s, 6H), 1.10 (s, 6H).

Example 39. 4-((5-cyano-4-(1-(oxetan-3-yl)-1H-pyrazol-4-yl)pyrimidin-2-yl)amino)benzenesulfonamide

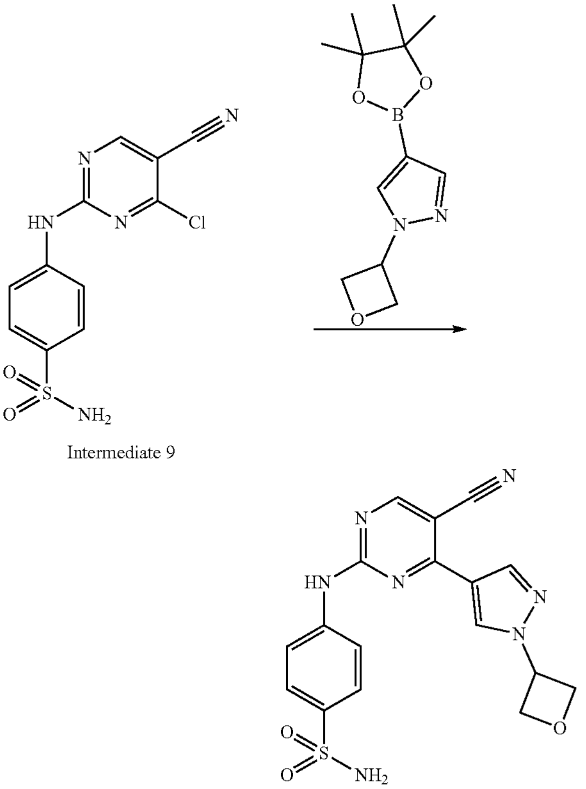

To a solution of Intermediate 9 (100 mg, 322 μmol) and 1-(oxetan-3-yl)-4-(4,4,5,5-tetramethyl-1,3,2-dioxaborolan-2-yl)-1H-pyrazole (96.5 mg, 386 μmol) in dioxane (10 mL) and $H_2O$ (1 mL) was added $Pd(t\text{-}Bu_3P)_2$ (65.4 mg, 128 μmol) and $Na_2CO_3$ (102 mg, 965 μmol). The reaction was stirred at 100° C. for 2 h. The reaction mixture was purified by Prep-HPLC (Basic conditions) to give the title compound (17.2 mg, 13.5% yield) as a white solid. MS (ES+) $C_{17}H_{15}N_7O_3S$ requires: 397, found: 398 $[M+H]^+$. $^1H$-NMR (400 MHz, DMSO-$d_6$) δ ppm 10.70 (s, 1H), 8.93 (s, 1H), 8.69 (s, 1H), 8.43 (s, 1H), 7.96 (d, J=8.8 Hz, 2H), 7.83 (d, J=8.8 Hz, 2H), 7.26 (s, 2H), 5.86-5.82 (m, 1H), 4.98-4.92 (m, 4H).

Example 40. 3-fluoro-4-((4-(1-(2-hydroxy-2-methylpropyl)-1H-pyrazol-4-yl)-5-(trifluoromethyl)pyrimidin-2-yl)amino)-2-methoxybenzenesulfonamide

Step 1. Synthesis of 4-bromo-3-fluoro-2-methoxybenzenesulfonyl chloride (Intermediate 41)

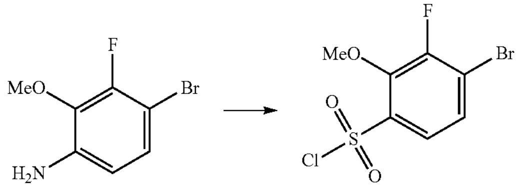

Intermediate 41

The title compound was obtained (200 mg, crude) from 4-bromo-3-fluoro-2-methoxyaniline, following the procedure described in Example 38, step 1.

Step 2. Synthesis of 4-bromo-3-fluoro-2-methoxybenzenesulfonamide (Intermediate 42)

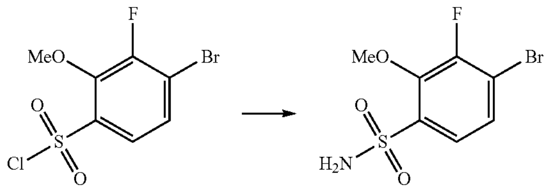

Intermediate 41 Intermediate 42

The title compound was obtained as a yellow solid, 150 mg, 80% yield, from Intermediate 41, following a similar procedure to that described in Example 28, step 2. MS (ES+) $C_7H_7BrFNO_3S$ requires: 283, found: 284 $[M+H]^+$.

Step 3. Synthesis of 3-fluoro-4-((4-(1-(2-hydroxy-2-methylpropyl)-1H-pyrazol-4-yl)-5-(trifluoromethyl)pyrimidin-2-yl)amino)-2-methoxybenzenesulfonamide (Example 40)

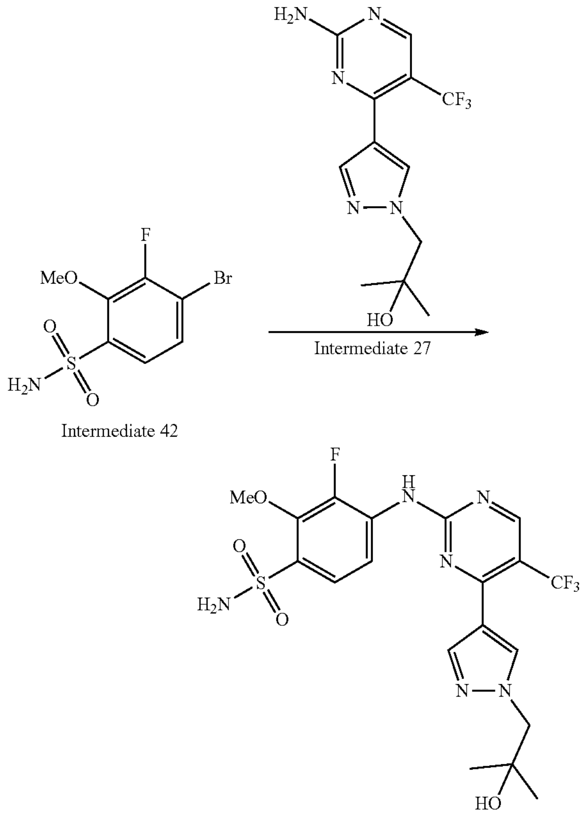

The title compound was obtained as a yellow solid, 60 mg, 28% yield, from Intermediate 27, and Intermediate 42, following the procedure described in Example 9, step 3. MS (ES+) $C_{19}H_{20}F_4N_6O_4S$ requires: 504, found: 505 $[M+H]^+$. $^1H$-NMR (400 MHz, DMSO-$d_6$) δ ppm 10.09 (s, 1H), 8.77 (s, 1H), 8.24 (s, 1H), 7.95 (s, 1H), 7.67 (dd, J=8.8 Hz, 6.4 Hz, 1H), 7.58 (d, J=8.8 Hz, 1H), 7.33 (s, 2H), 4.78 (s, 1H), 4.11 (s, 2H), 3.98 (s, 3H), 1.07 (s, 6H).

Example 41. 3-fluoro-4-((4-(1-((3-hydroxyoxetan-3-yl)methyl)-1H-pyrazol-4-yl)-5-(trifluoromethyl)pyrimidin-2-yl)amino)benzenesulfonamide

Step 1. Synthesis of 3-((4-(4,4,5,5-tetramethyl-1,3,2-dioxaborolan-2-yl)-1H-pyrazol-1-yl)methyl)oxetan-3-ol (Intermediate 43)

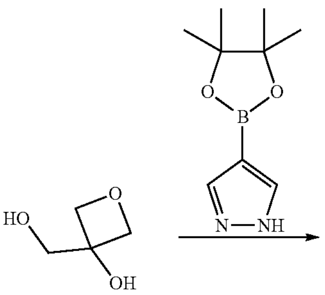

-continued

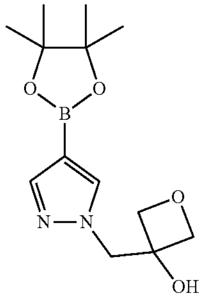

Intermediate 43

To a mixture of 4-(4,4,5,5-tetramethyl-1,3,2-dioxaborolan-2-yl)-1H-pyrazole (931 mg, 4.80 mmol), 3-(hydroxymethyl)oxetan-3-ol (500 mg, 4.80 mmol) and triphenyl phosphine (1.51 g, 5.76 mmol) in toluene (20 mL) was added dropwise DIAD (1.16 g, 5.76 mmol) at 80° C. The reaction mixture was stirred overnight. LCMS indicated completion of the reaction. The reaction was quenched with water and extracted with EA. The combined organic layer was washed with water and brine, dried over sodium sulfate, filtered and concentrated. The residue was purified by flash chromatography on silica gel eluting with PE/EA (4/1) to give the title compound (700 mg, 52% yield) as a yellow solid. MS (ES+) $C_{13}H_{21}BN_2O_4$ requires: 280, found: 281 $[M+H]^+$.

Step 2. Synthesis of 3-((4-(2-amino-5-(trifluoromethyl)pyrimidin-4-yl)-1H-pyrazol-1-yl)methyl) oxetan-3-ol (Intermediate 44)

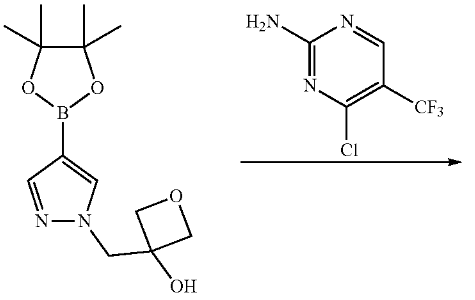

Intermediate 43

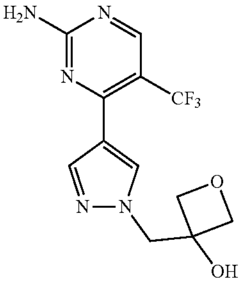

Intermediate 44

A mixture of Intermediate 43 (250 mg, 892 µmol), 4-chloro-5-(trifluoromethyl)pyrimidin-2-amine (176 mg, 892 µmol), $Na_2CO_3$ (283 mg, 2.67 mmol) and $Pd(dppf)Cl_2$ (65.2 mg, 89.2 µmol) in dioxane (10 mL) and $H_2O$ (2.5 mL) was stirred at 80° C. for 4 h under $N_2$. LCMS indicated completion of the reaction. The reaction mixture was concentrated and the residue was purified by flash chromatography on silica gel eluting with DCM/MeOH (5/1) to afford the title compound (170 mg, 60% yield) as a white solid. MS (ES+) $C_{12}H_{12}F_3N_5O_2$ requires: 315, found: 316 [M+H]+.

Step 3. Synthesis of 3-fluoro-4-((4-(1-((3-hydroxyoxetan-3-yl)methyl)-1H-pyrazol-4-yl)-5-(trifluoromethyl)pyrimidin-2-yl)amino)benzenesulfonamide (Example 41)

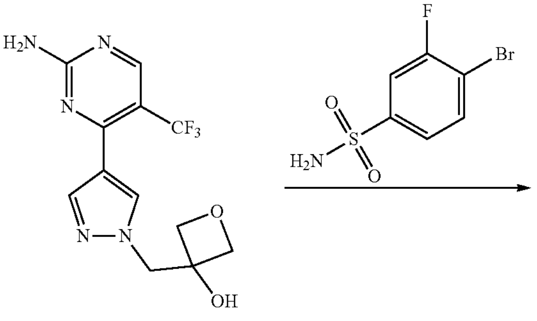

Intermediate 44

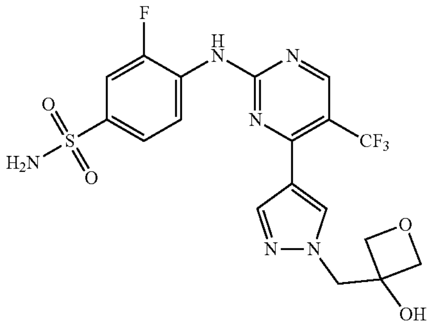

To a mixture of Intermediate 44 (140 mg, 444 µmol) and 4-bromo-3-fluorobenzenesulfonamide (112 mg, 444 µmol) in dioxane (5 mL) was added $Pd_2(dba)_3$ (40.6 mg, 44.4 µmol), t-BuXPhos (18.8 mg, 44.4 µmol) and KOAc (130 mg, 1.33 mmol), then stirred at 100° C. for 4 h under $N_2$. LCMS indicated completion of the reaction. The reaction mixture was purified by Prep-HPLC (Basic conditions) to give the title compound (30.1 mg, 13% yield) as a white solid. MS (ES+) $C_{18}H_{16}F_4N_6O_4S$ requires: 488, found: 489 $[M+H]^+$. $^1H$ NMR (400 MHz, DMSO) δ 10.10 (s, 1H), 8.78 (s, 1H), 8.26 (s, 1H), 8.02 (t, J=8.0 Hz, 1H), 7.98 (s, 1H), 7.71 (s, 1H), 7.68 (s, 1H), 7.45 (s, 2H), 6.22 (s, 1H), 4.60-4.57 (m, 2H), 4.53 (s, 2H), 4.45-4.44 (m, 2H).

Example 42. 4-((5-ethyl-4-(1-(2-hydroxy-2-methylpropyl)-1H-pyrazol-4-yl)pyrimidin-2-yl)amino)-3-fluorobenzenesulfonamide Step 1. Synthesis of 1-(4-(2-chloro-5-ethylpyrimidin-4-yl)-1H-pyrazol-1-yl)-2-methylpropan-2-ol (Intermediate 45)

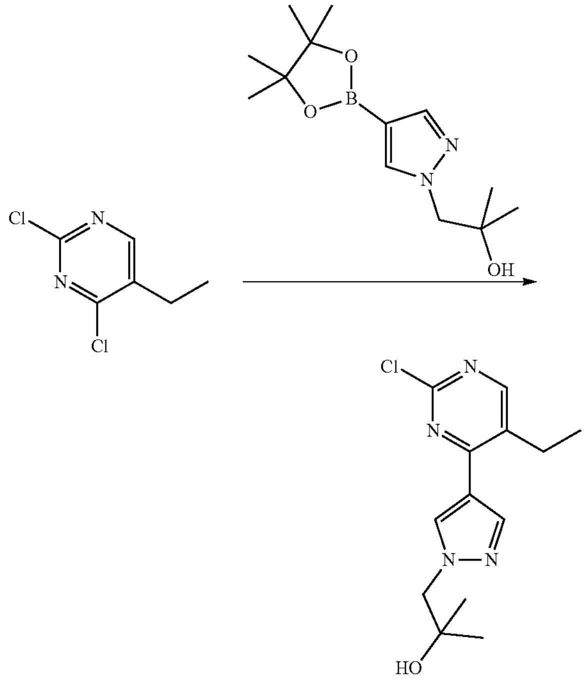

Intermediate 45

A mixture of 2-methyl-1-(4-(4,4,5,5-tetramethyl-1,3,2-dioxaborolan-2-yl)-1H-pyrazol-1-yl)propan-2-ol (270 mg, 1.01 mmol), 2,4-dichloro-5-ethylpyrimidine (357 mg, 2.02 mmol), $Na_2CO_3$ (136 mg, 1.29 mmol), Pd(dppf)$Cl_2$ (37.0 mg, 50.5 μmol) in dioxane (12 mL) and $H_2O$ (3 mL) was stirred at 90° C. overnight under $N_2$. LCMS indicated completion of the reaction. The reaction mixture was concentrated and the residue was purified by flash chromatography on silica gel eluting with PE/EA (1/1) to afford the title compound (150 mg, 53% yield) as a yellow solid. MS (ES+) $C_{13}H_{17}ClN_4O$ requires: 280, found: 281 [M+H].

Step 2. Synthesis of 4-((5-ethyl-4-(1-(2-hydroxy-2-methylpropyl)-1H-pyrazol-4-yl)pyrimidin-2-yl)amino)-3-fluorobenzenesulfonamide (Example 42)

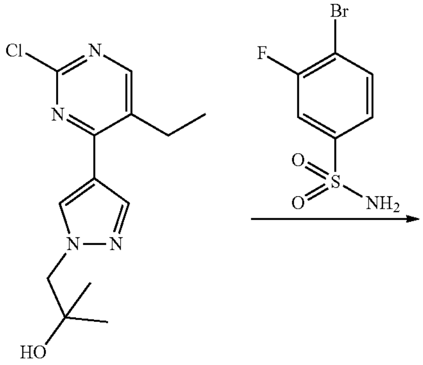

Intermediate 45

-continued

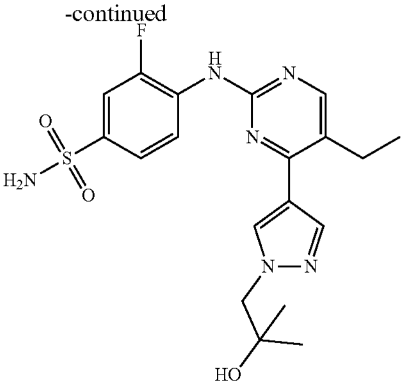

A mixture of Intermediate 45 (120 mg, 427 μmol), 4-amino-3-fluorobenzene-1-sulfonamide (97.3 mg, 512 μmol), TsOH (73.5 mg, 427 μmol) in IPA (10 mL) was stirred at 90° C. for 3 d. LCMS indicated completion of the reaction. The reaction mixture was purified by Prep-HPLC (Acidic conditions) to give the title compound (24.3 mg, 13% yield) as a white solid. MS (ES+) $C_{19}H_{23}FN_6O_3S$ requires: 434, found: 435 $[M+H]^+$. $^1H$ NMR (400 MHz, DMSO) δ 9.16 (s, 1H), 8.37-8.28 (m, 3H), 8.02 (s, 1H), 7.65-7.60 (m, 2H), 7.35 (s, 2H), 4.78 (s, 1H), 4.12 (s, 2H), 2.75 (q, J=7.2 Hz, 2H), 1.23-1.16 (m, 4H), 1.10 (s, 6H).

Example 43. 3-fluoro-4-((4-(1-(oxetan-3-yl)-1H-pyrazol-4-yl)-5-(trifluoromethyl)pyrimidin-2-yl)amino)benzenesulfonamide Step 1. Synthesis of 4-(1-(oxetan-3-yl)-1H-pyrazol-4-yl)-5-(trifluoromethyl)pyrimidin-2-amine (Intermediate 46)

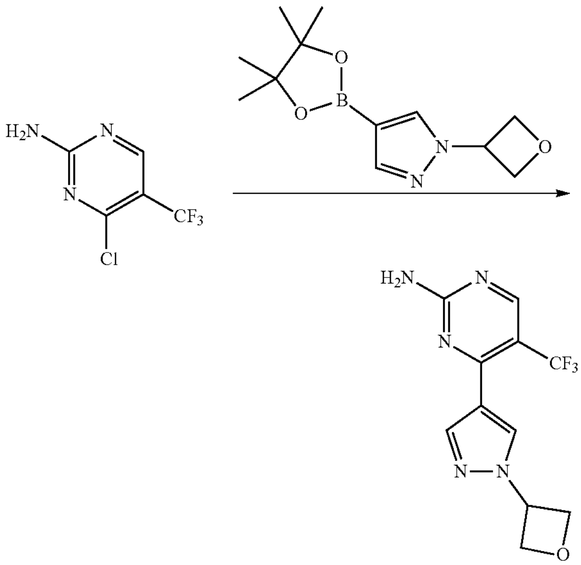

Intermediate 46

The title compound was obtained as a yellow solid, 200 mg, 69% yield, from 4-chloro-5-(trifluoromethyl)pyrimidin-2-amine and 1-(oxetan-3-yl)-4-(4,4,5,5-tetramethyl-1,3,2-dioxaborolan-2-yl)-1H-pyrazole following a similar procedure to that described in Example 3, step 1. MS (ES+) $C_{11}H_{10}F_3N_5O$ requires: 285, found: 286 $[M+H]^+$.

Step 2. Synthesis of 3-fluoro-4-((4-(1-(oxetan-3-yl)-1H-pyrazol-4-yl)-5-(trifluoromethyl)pyrimidin-2-yl)amino)benzenesulfonamide (Example 43)

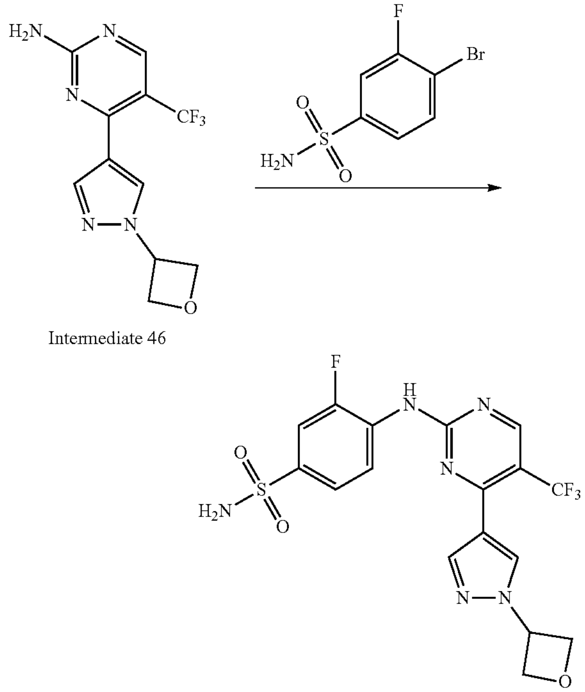

Intermediate 46

To a solution of Intermediate 46 (150 mg, 525 μmol), 4-bromo-3-fluorobenzene-1-sulfonamide (199 mg, 787 μmol), potassium acetate (154 mg, 1.57 mmol), BrettPhos Pd G4 (80.6 mg, 52.5 μmol) in dioxane (3 mL) was stirred at 90° C. overnight under $N_2$. LCMS indicated completion of the reaction. The reaction mixture was purified by Prep-HPLC (Basic conditions) to give the title compound (110.4 mg, 45% yield) as a white solid. MS (ES+) $C_{17}H_{14}F_4N_6O_3S$ requires: 458, found: 459 $[M+H]^+$. $^1H$ NMR (400 MHz, DMSO) δ 10.11 (s, 1H), 8.79 (s, 1H), 8.36 (s, 1H), 8.11 (s, 1H), 8.02 (t, J=8.0 Hz, 1H), 7.71-7.67 (m, 2H), 7.45 (s, 2H), 5.80-5.75 (m, 1H), 4.96-4.89 (m, 4H).

Example 44. 3-chloro-4-((5-fluoro-4-(1-(2-hydroxy-2-methylpropyl)-1H-pyrazol-4-yl)pyrimidin-2-yl)amino)benzenesulfonamide

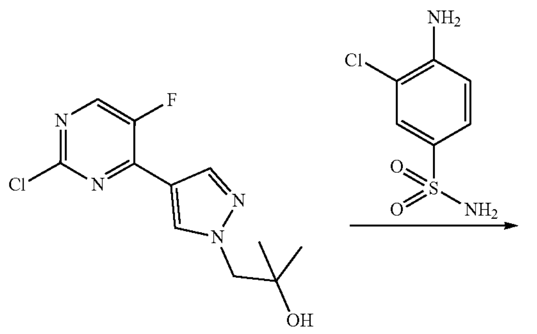

Intermediate 21

-continued

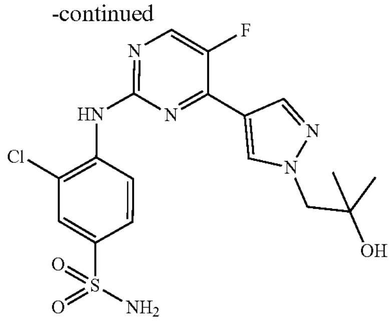

A mixture of Intermediate 21 (80 mg, 296 μmol), 4-amino-3-chlorobenzenesulfonamide (61 mg, 296 μmol), KOAc (87 mg, 888 μmol), tBuXPhos (12.5 mg, 29.6 μmol) and $Pd_2(dba)_3$ (27.1 mg, 29.6 μmol) in dioxane (2 mL) was stirred at 90° C. for 16 h under $N_2$. LCMS indicated completion of the reaction. The reaction mixture was purified by Prep-HPLC (Basic conditions) to give the title compound (11.8 mg, 9% yield) as a white solid. MS (ES+) $C_{17}H_{18}ClFN_6O_3S$ requires: 440, found: 441 $[M+H]^+$. $^1H$-NMR (400 MHz, DMSO-$d_6$) δ ppm 8.90 (s, 1H), 8.57 (d, J=2.8 Hz, 1H), 8.36 (s, 1H), 8.28 (d, J=8.8 Hz, 1H), 8.08 (s, 1H), 7.90 (s, 1H), 7.80 (dd, J=8.8 Hz, 2.4 Hz, 1H), 7.39 (s, 2H), 4.80 (s, 1H), 4.15 (s, 2H), 1.10 (s, 6H).

Example 45. 5-fluoro-4-((4-(1-(2-hydroxy-2-methylpropyl)-1H-pyrazol-4-yl)-5-(trifluoromethyl)pyrimidin-2-yl)amino)-2-methylbenzenesulfonamide

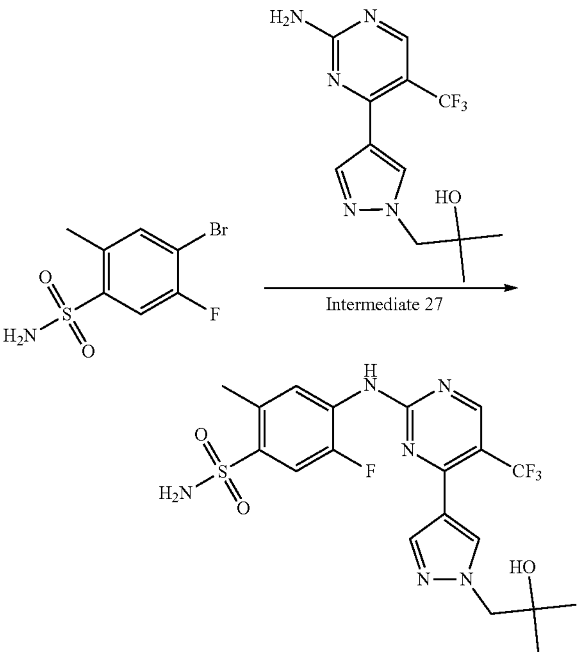

A mixture of 4-bromo-5-fluoro-2-methylbenzenesulfonamide (225 mg, 839 μmol), 1-(4-(2-amino-5-(trifluoromethyl)pyrimidin-4-yl)-1H-pyrazol-1-yl)-2-methylpropan-2-ol (Intermediate 27, 252 mg, 839 μmol), BrettPhos Pd G4 (100 mg, 1.01 mmol) and potassium acetate (245 mg, 2.51 mmol) in dioxane (5 mL) was stirred at 100° C. overnight under $N_2$. The reaction mixture was cooled to RT and concentrated to give a residue which was purified by flash column chromatography on silica gel eluting with PE/EA (1/4) and then Prep-HPLC (basic conditions) to give the title product (102 mg, 25% yield), as a white solid. MS (ES+) $C_{19}H_{20}F_4N_6O_3S$ requires: 488, found: 489 $[M+H]^+$. $^1$H-NMR (400 MHz, DMSO-$d_6$) δ ppm 10.04 (s, 1H), 8.77 (s, 1H), 8.25 (s, 1H), 7.94 (s, 1H), 7.84 (d, J=7.6 Hz, 1H), 7.67 (d, J=11.2 Hz, 1H), 7.49 (s, 2H), 4.79 (s, 1H), 4.12 (s, 2H), 2.58 (s, 3H), 1.09 (s, 6H).

Example 46. 4-((5-fluoro-4-(1-(2-hydroxy-2-methylpropyl)-1H-pyrazol-4-yl)pyrimidin-2-yl)amino)-3-methoxybenzenesulfonamide

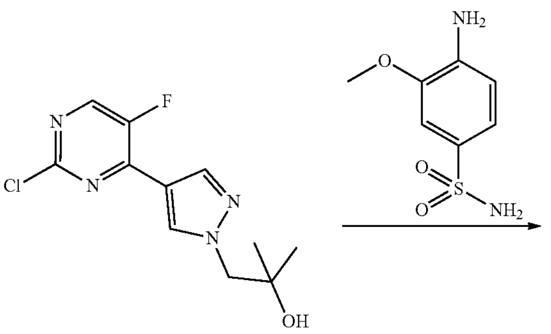

Intermediate 21

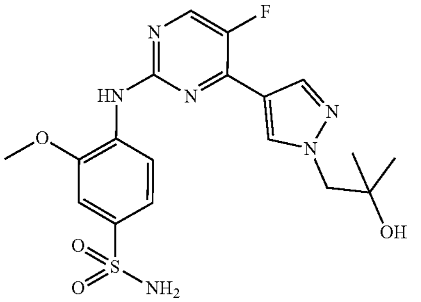

To a mixture of Intermediate 21 (100 mg, 369 μmol) and 4-amino-3-methoxybenzenesulfonamide (74.6 mg, 369 μmol) in dioxane (5 mL) was added $Pd_2(dba)_3$ (33.7 mg, 36.8 μmol), t-BuXPhos (15.6 mg, 36.7 μmol) and KOAc (107 mg, 1.10 mmol), then stirred at 100° C. for 4 h under $N_2$. LCMS indicated completion of the reaction. The reaction mixture was purified by Prep-HPLC (Basic conditions) to give the title compound (2.0 mg, 1% yield) as a white solid. MS (ES+) $C_{18}H_{21}FN_6O_4S$ requires: 436, found: 437 $[M+H]^+$. $^1$H-NMR (400 MHz, DMSO-$d_6$) δ ppm 8.59 (d, J=2.8 Hz, 1H), 8.48 (d, J=8.4 Hz, 1H), 8.41 (s, 1H), 8.25 (s, 1H), 8.14 (s, 1H), 7.50 (dd, J=8.4 Hz, 2.8 Hz, 11H), 7.46 (s, 1H), 7.23 (s, 2H), 4.80 (s, 1H), 4.16 (s, 2H), 3.96 (s, 3H), 1.10 (s, 6H).

Example 47. 3-fluoro-4-((4-(1-(tetrahydro-2H-pyran-4-yl)-1H-pyrazol-4-yl)-5-(trifluoromethyl)pyrimidin-2-yl)amino)benzenesulfonamide Step 1. Synthesis of 4-(1-(tetrahydro-2H-pyran-4-yl)-1H-pyrazol-4-yl)-5-(trifluoromethyl)pyrimidin-2-amine (Intermediate 47)

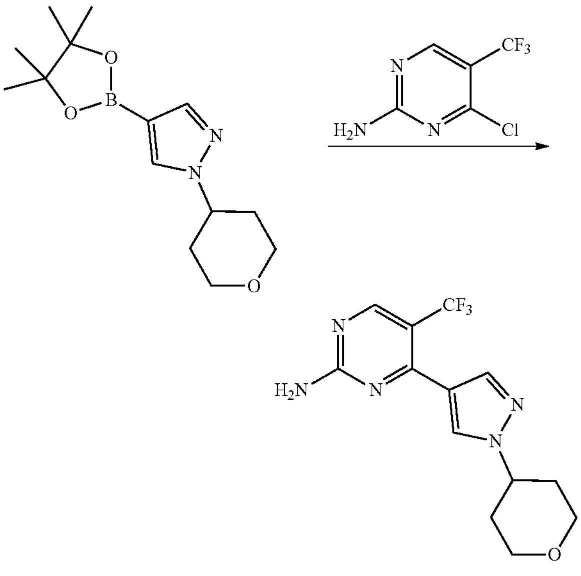

Intermediate 47

A mixture of 1-(tetrahydro-2H-pyran-4-yl)-4-(4,4,5,5-tetramethyl-1,3,2-dioxaborolan-2-yl)-1H-pyrazole (400 mg, 1.43 mmol), 4-chloro-5-(trifluoromethyl)pyrimidin-2-amine (422 mg, 2.14 mmol), $Na_2CO_3$ (454 mg, 4.29 mmol) and Pd(dppf)$Cl_2$ (104 mg, 143 μmol) in dioxane (10 mL) and $H_2O$ (1 mL) was stirred at 80° C. for 2 h under $N_2$. LCMS indicated completion of the reaction. The reaction mixture was concentrated and the residue was purified by flash chromatography on silica gel eluting with EA/PE (1/4) to afford the title compound (324 mg, 72% yield) as a yellow solid. MS (ES+) C13H14F3$N_5$O requires: 313, found: 314 $[M+H]^+$.

Step 2. Synthesis of 3-fluoro-4-((4-(1-(tetrahydro-2H-pyran-4-yl)-1H-pyrazol-4-yl)-5-(trifluoromethyl)pyrimidin-2-yl)amino)benzenesulfonamide (Example 47)

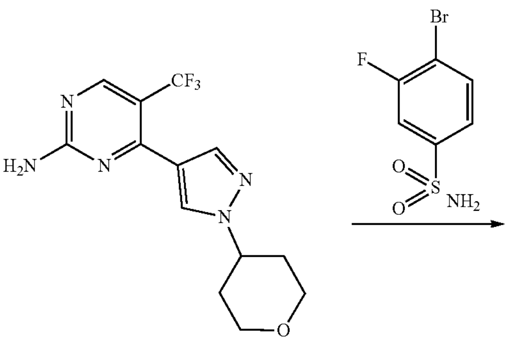

Intermediate 47

-continued

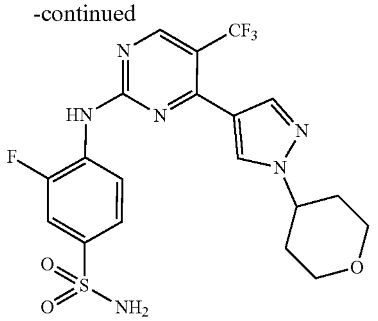

To a mixture of Intermediate 47 (324 mg, 1.03 mmol) and 4-bromo-3-fluorobenzenesulfonamide (312 mg, 1.23 mmol) in dioxane (10 mL) was added KOAc (202 mg, 2.06 mmol) and BrettPhos Pd G4 (25 mg), then stirred at 90° C. for 16 h under $N_2$. LCMS indicated completion of the reaction. The reaction mixture was purified by Prep-HPLC (Basic conditions) to give the title compound (197.6 mg, 39% yield) as a white solid. MS (ES+) $C_{19}H_{18}F_4N_6O_3$ requires: 486, found: 487 $[M+H]^+$. $^1$H-NMR (400 MHz, DMSO-$d_6$) δ ppm 10.07 (br. s., 1H), 8.77 (s, 1H), 8.29 (s, 1H), 8.05-7.98 (m, 2H), 7.70-7.66 (m, 2H), 7.45 (br. s., 2H), 4.59-4.55 (m, 1H), 3.99-3.96 (m, 2H), 3.50-3.43 (m, 2H), 2.01-1.95 (m, 4H).

Biological Example 1. Biochemical CDK Inhibition Assays

Inhibitory effects of the compounds of the disclosure were measured in biochemical assays that measure the enzymatic phosphorylation activity of CDK enzyme in complex of Cyclin proteins phosphorylates 7.5 micromolar fluorescently labelled peptide substrate, 5-FAM-QSPKKG-CONH2, (FL-Peptide 18, Perkin Elmer, 760362) in the presence of adenosine-5'-triphosphate (ATP) and varying concentrations of the test compound in 100 mM 2-[4-(2-hydroxyethyl)piperazin-1-yl] ethanesulfonic acid (HEPES), pH 7.5, 10 mM $MgCl_2$, 0.015% Brij-35, 1 mM dithiothreitol (DTT), 1.0% dimehylsulfoxide (DMSO). Assays were performed at 1.0 mM ATP or at ATP Km of the CDK enzymes in complex with Cyclin proteins. Reactions proceeded until between 10% to 20% total peptides were phosphorylated at room temperature (25° C.) and were terminated with 35 mM 2,2',2'',2'''-(ethane-1,2-diyldinitrilo)tetraacetic acid (EDTA). Product was detected using the Caliper mobility shift detection method where the phosphorylated peptide (product) and substrate were electrophoretically separated and measured. Percent activity was plotted against log concentration of compound and points to generate an apparent $IC_{50}$. The following CDK enzymes in complex with different cyclin proteins were used in these assays:

CDK1/Cyclin B1, GST-tag (BPS, 40454), 1.5 nM used in the assay

CDK2/Cyclin E (Eurofins, 14-475), 1.25 nM used in the assays

Biological assay data of the test compounds are provided in Table 1 below. For inhibitory activity against CDK2/Cyclin E mutant, the following designations are used: ≤10 nM=A; >10-20 nM=B; >20-30 nM=C; >30-100 nM=D and >100=E. For inhibition CDK1/Cyclin B1, GST-tag: ≥500 nM=A; <100-500 nM=B; <100 nM=C.

TABLE 1

Tabularized Data:

| no. | CDK2/ cyclin E1 IC50 (nM) | CDK1/ cyclin B1 IC50 (nM) |
|---|---|---|
| 1 | A | B |
| 2 | A | B |
| 3 | A | C |
| 4 | A | C |
| 5 | A | C |
| 6 | A | C |
| 7 | A | B |
| 8 | A | C |
| 9 | A | B |
| 10 | A | C |
| 11 | A | B |
| 12 | A | B |
| 13 | A | B |
| 14 | A | C |
| 15 | A | B |
| 16 | A | B |
| 17 | A | B |
| 18 | A | C |
| 19 | A | B |
| 20 | A | B |
| 21 | A | B |
| 22 | A | B |
| 23 | A | B |
| 24 | A | B |
| 25 | A | B |
| 26 | A | B |
| 27 | A | B |
| 28 | A | B |
| 29 | A | A |
| 30 | A | B |
| 31 | A | B |
| 32 | B | A |
| 33 | B | A |
| 34 | B | B |
| 35 | B | A |
| 36 | B | A |
| 37 | B | B |
| 38 | B | A |
| 39 | B | A |
| 40 | B | A |
| 41 | B | A |
| 42 | C | A |
| 43 | C | A |
| 44 | C | A |
| 45 | C | A |
| 46 | D | A |
| 47 | A | A |

The invention claimed is:

1. A compound of Formula I (I)

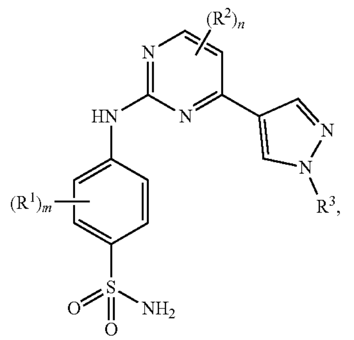

or a pharmaceutically acceptable salt thereof, wherein each $R^1$ is independently selected from the group consisting of halo, OH, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 halo;

each $R^2$ is independently selected from the group consisting of halo, OH, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 halo;

$R^3$ is $C_1$-$C_6$alkyl optionally substituted with 1 or 2 groups each independently selected from the group consisting of halo, OH, $C_3$-$C_6$cycloalkyl, and 3 to 6-membered heterocyclyl, wherein the $C_3$-$C_6$cycloalkyl is optionally substituted with OH, wherein the 3 to 6-membered heterocyclyl has 1 to 4 ring heteroatoms each independently selected from the group consisting of O, S, N, and $NR^a$ and then is optionally substituted on a ring carbon with OH; or $R^3$ is $C_3$-$C_6$cycloalkyl or 3 to 6-membered heterocyclyl, wherein the $C_3$-$C_6$cycloalkyl is optionally substituted with OH or —$CH_2OH$, wherein the 3 to 6-membered heterocyclyl has 1 to 4 ring heteroatoms each independently selected from the group consisting of O, S, N, and $NR^a$ and then is optionally substituted on a ring carbon with OH or —$CH_2OH$;

each $R^a$ is independently H or $C_1$-$C_6$alkyl;

m is selected from the group consisting of 0, 1, 2, 3, and 4, and n is selected from the group consisting of 0, 1, and 2.

2. The compound of claim 1, wherein the compound is of Formula IIA, Formula IIB, Formula IIC, or Formula IID (IIA)

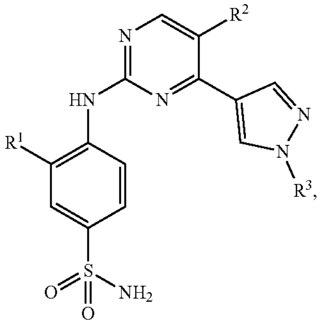

(IIB)

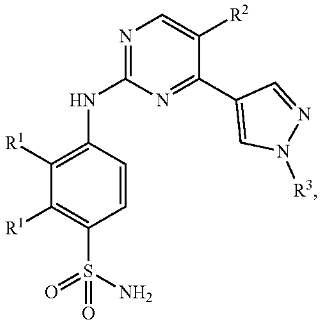

-continued (IIC)

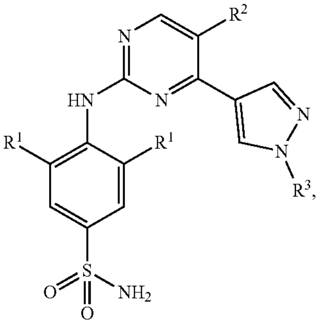

or (IID)

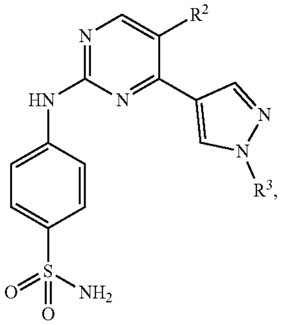

or a pharmaceutically acceptable salt thereof.

3. The compound of claim 1, wherein each $R^1$ is independently selected from the group consisting of halo, methyl, and methoxy.

4. The compound of claim 1, wherein each $R^2$ is independently selected from the group consisting of halo, CN, methyl, and ethyl, wherein the methyl and ethyl are each optionally substituted with 1 to 3 halo.

5. The compound of claim 1, wherein $R^3$ is $C_1$-$C_5$alkyl optionally substituted with 1 or 2 groups each independently selected from the group consisting of halo, OH, cyclopropyl and oxetanyl, wherein the cyclopropyl and oxetanyl are each optionally substituted with OH.

6. The compound of claim 1, wherein $R^3$ is $C_1$-$C_5$alkyl substituted with OH.

7. The compound of claim 1, wherein each $R^1$ is methyl, each $R^2$ is independently selected from the group consisting of halo, methyl, and $CF_3$, and $R^3$ is $C_1$-$C_6$alkyl substituted with OH.

8. The compound of claim 1, wherein each $R^1$ is halo, each $R^2$ is independently selected from the group consisting of halo, CN, methyl, ethyl, and $CF_3$, and $R^3$ is $C_1$-$C_6$alkyl substituted with OH.

9. A compound selected from the group consisting of:

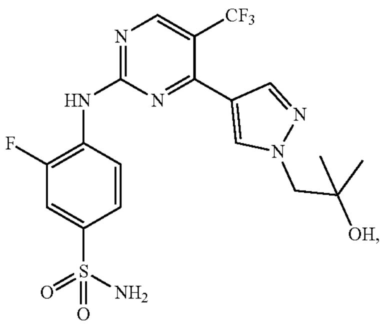

-continued
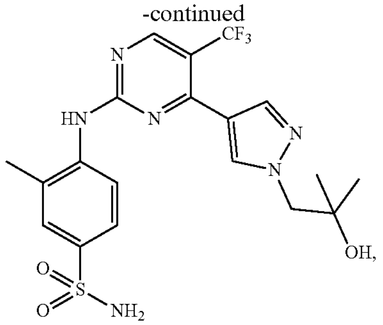
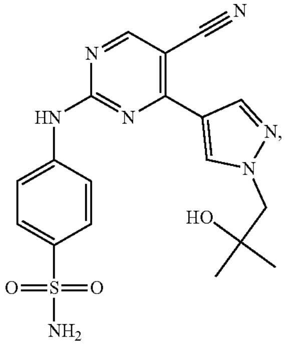
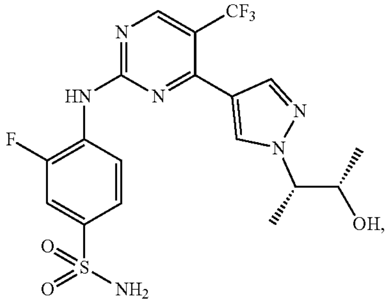
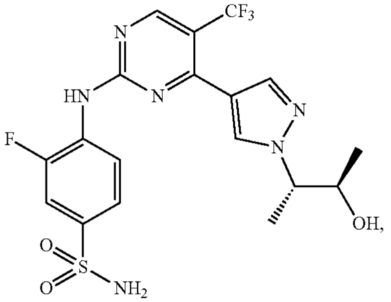
and
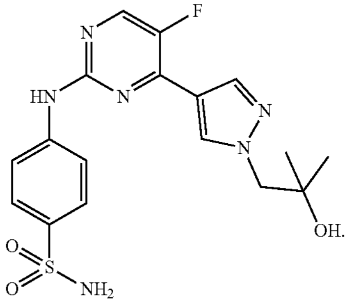
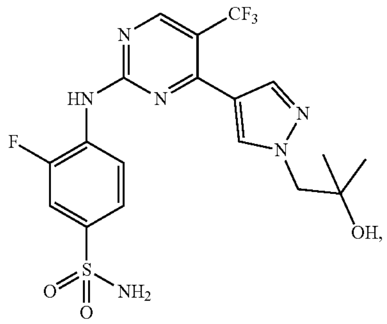
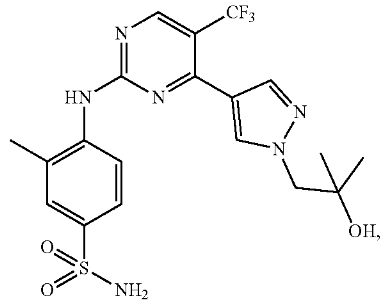
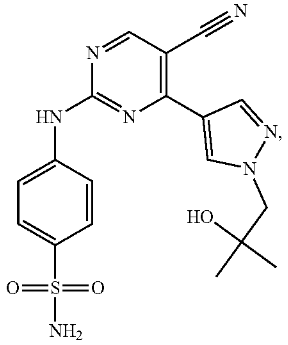
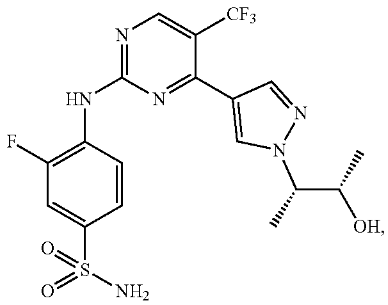
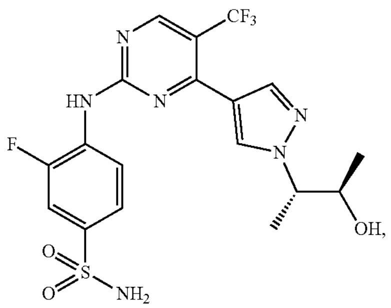
and
10. A pharmaceutically acceptable salt of a compound selected from the group consisting of:

-continued

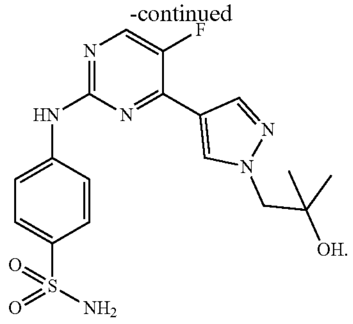

11. A pharmaceutical composition comprising a pharmaceutically acceptable carrier and the compound of claim 1, or a pharmaceutically acceptable salt thereof.

12. A pharmaceutical composition comprising a pharmaceutically acceptable carrier and the compound of claim 9, or a pharmaceutically acceptable salt thereof.

13. A method of treating a cancer in a subject in need thereof, comprising administering to the subject an effective amount of the compound of claim 1, or a pharmaceutically acceptable salt thereof.

14. The method of claim 13, wherein the cancer is breast cancer.

15. A method of treating a subject suffering from, or at risk of developing, a solid tumor cancer, comprising administering to the subject a therapeutically effective amount of a compound of claim 1, or a pharmaceutically acceptable salt thereof.

16. The method of claim 15, wherein the solid tumor cancer is at least one of: uterine cancer, endometrial cancer, breast cancer, ovarian cancer, stomach cancer, gastric cancer, colorectal cancer, pancreatic cancer, kidney cancer, head and neck cancer, liver cancer, prostate cancer, skin cancer, lymphoma, sarcoma, esophageal cancer, bladder cancer, lung cancer, cholangiocarcinoma, adrenocortical carcinoma, or mesothelioma.

17. A method of treating a cancer in a subject in need thereof, comprising administering to the subject an effective amount of the compound of claim 9, or a pharmaceutically acceptable salt thereof.

18. The method of claim 17, wherein the cancer is breast cancer.

19. A method of treating a subject suffering from, or at risk of developing, a solid tumor cancer, comprising administering to the subject a therapeutically effective amount of a compound of claim 9, or a pharmaceutically acceptable salt thereof.

20. The method of claim 19, wherein the solid tumor cancer is at least one of: uterine cancer, endometrial cancer, breast cancer, ovarian cancer, stomach cancer, gastric cancer, colorectal cancer, pancreatic cancer, kidney cancer, head and neck cancer, liver cancer, prostate cancer, skin cancer, lymphoma, sarcoma, esophageal cancer, bladder cancer, lung cancer, cholangiocarcinoma, adrenocortical carcinoma, or mesothelioma.

* * * * *